US006916982B2

(12) United States Patent
Loewe et al.

(10) Patent No.: US 6,916,982 B2
(45) Date of Patent: Jul. 12, 2005

(54) SYNTHESIS OF PERYLENE-PORPHYRIN BUILDING BLOCKS AND POLYMERS THEREOF FOR THE PRODUCTION OF LIGHT-HARVESTING ARRAYS

(75) Inventors: Robert S. Loewe, Morrisville, NC (US); Kin-ya Tomizaki, Raleigh, NC (US); Jonathan S. Lindsey, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 10/164,474

(22) Filed: Jun. 6, 2002

(65) Prior Publication Data

US 2003/0075216 A1 Apr. 24, 2003

Related U.S. Application Data

(63) Continuation-in-part of application No. 09/621,797, filed on Jul. 21, 2000, now Pat. No. 6,420,648.

(51) Int. Cl.[7] .................. H01L 31/0256; C07D 221/18; C07D 311/00
(52) U.S. Cl. ..................... 136/263; 136/252; 136/256; 257/40; 257/431; 429/111; 252/501.1; 546/37; 546/38; 549/232; 540/145
(58) Field of Search ........................ 136/263, 252, 136/256; 257/40, 431; 429/111; 252/501.1; 546/38, 37; 549/232; 540/145

(56) References Cited

U.S. PATENT DOCUMENTS

| 5,539,100 | A | | 7/1996 | Wasielewski et al. |
|---|---|---|---|---|
| 5,808,073 | A | * | 9/1998 | Bohm et al. ................ 546/39 |
| 6,407,330 | B1 | * | 6/2002 | Lindsey et al. ............ 136/263 |
| 6,420,648 | B1 | * | 7/2002 | Lindsey ..................... 136/263 |
| 6,441,174 | B1 | * | 8/2002 | Hendi ......................... 546/37 |
| 6,464,902 | B1 | * | 10/2002 | Gaynor et al. .............. 252/600 |
| 6,559,374 | B2 | * | 5/2003 | Lindsey et al. ............ 136/263 |
| 6,596,935 | B2 | * | 7/2003 | Lindsey et al. ............ 136/263 |
| 6,603,070 | B2 | * | 8/2003 | Lindsey et al. ............ 136/263 |
| 2002/0185173 | A1 | * | 12/2002 | Lindsey et al. ............ 136/263 |
| 2003/0111108 | A1 | * | 6/2003 | Lindsey et al. ............ 136/263 |
| 2004/0254383 | A1 | * | 12/2004 | Yu et al. ..................... 548/402 |

FOREIGN PATENT DOCUMENTS

| JP | 6-252379 A | * | 9/1994 |
|---|---|---|---|
| JP | 9-18039 | * | 1/1997 |
| WO | WO 02/08230 | | 1/2002 |

OTHER PUBLICATIONS

Schneider et al, "Hybrid Materials Doped with Covalently Bound Perylene Dyes through the Sol–Gel Process," Chem. Mater., vol. 12, pp. 352–362, Feb. 4, 2000.*

(Continued)

Primary Examiner—Alan Diamond
(74) Attorney, Agent, or Firm—Myers Bigel Sibley & Sajovec, PA

(57) ABSTRACT

The present invention provides methods, compounds, and compositions for the synthesis of light harvesting arrays, such arrays comprising: (a) a first substrate comprising a first electrode; and (b) a layer of light harvesting rods electrically coupled to said first electrode, each of said light harvesting rods comprising a polymer of Formula I:

$$X^1\!-\!(X^{m+1})_m \qquad (I)$$

wherein m is at least 1; $X^1$ is a charge separation group, and $X^2$ through $X^{m+1}$ are chromophores. At least one of $X^2$ through $X^{m+1}$ has at least one perylene group coupled thereto.

81 Claims, 4 Drawing Sheets

OTHER PUBLICATIONS

Hayes et al, "Ultrafast Photoswitched Charge Transmission through the Bridge Molecule in a Donor–Bridge–Acceptor System," J. Am. Chem. Soc., vol. 122, pp. 5563–5567, May 23, 2000.*

Miller et al, "A Tightly Coupled Linear Array of Perylene, Bis(Porphyrin), and Phthalocyanine Units that Functions as a Photoinduced Energy–Transfer Cascade," J. Org. Chem., vol. 65, pp. 6634–6649, Sep. 2, 2000.*

Tomizaki et al, "Synthesis and photophysical Properties of Light–Harvesting Arrays Comprised of a Porphyrin Bearing Multiple Perylene–Monoimide Accessory Pigments," J. Org. Chem., vol. 67, pp. 6519–6534, Aug. 14, 2002.*

Prathapan, "Synthesis and excited–state photodynamics of perylene–porphyrin dyads. 1. Parallel energy and charge transfer via a diphenylethyne linker," J. Phys. Chem. B, 105(34), PP. 8237–8248, Jul. 31, 2001.*

Yang et al, "Synthesis and excited–state photodynamics in perylene–porphyrin dyads. 2. Effects of porphyrin metalation state on the energy–transfer, charge–transfer, and deactivation channels," J. Phys. Chem. B, 105, pp. 8249–8258, Aug. 2, 2001.*

An abstract for Loewe et al, "Synthesis of perylene–porphyrin building blocks and rod–like oligomers for light–harvesting applications," J. Mater. Chem., 12(12), pp. 3438–3451, published Nov. 29, 2002.*

Hayes, Ryan T., et al., *Ultrafast Photoswitched Charge Transmission through the Bridge Molecule in a Donor-Bridge–Acceptor System, J. Am. Chem. Soc.*, vol. 122, pp. 5563–5567 May 23, 2000.

Li, Geirong, et al., *Design, Synthesis, and Photodynamics of Light–Harvesting Arrays Comprised of a Porphyrin and One, Two, or Eight Boron–Dipyrrin Accessory Pigments, Journal of the American Chemical Society*, vol. 120, No. 39, pp. 10001–10017 Sep. 19, 1998.

Miller, Mark A., et al., *A Tightly Coupled Linear Array of Perylene, Bis(Porphyrin), and Phthalocyanine Units that Functions as a Photoinduced Energy–Transfer Cascade, The Journal of Organic Chemistry*, vol. 65, No. 20, pp. 6634–6649 Sep. 2, 2000.

* cited by examiner

SYNTHESIS OF PERYLENE-PORPHYRIN BUILDING BLOCKS AND POLYMERS THEREOF FOR THE PRODUCTION OF LIGHT-HARVESTING ARRAYS

RELATED APPLICATIONS

This application is a continuation-in-part of commonly owned, U.S. patent application Ser. No. 09/621,797 Filed 21 Jul. 2000, now U.S. Pat. No. 6,420,648, the disclosure of which is incorporated by reference herein in its entirety.

STATEMENT OF GOVERNMENT SUPPORT

This invention was made with US Government support from the National Science Foundation (grant number CHE-9988142) and the Department of Energy (grant number DE-FG02-96ER14632). The Government has certain rights to this invention.

FIELD OF THE INVENTION

The present invention concerns substituted porphyrinic macrocycles, compositions containing the same, light harvesting rods produced from the polymerization thereof and compositions containing such rods, light harvesting arrays produced from such light harvesting rods, and solar cells produced from such light harvesting rods.

BACKGROUND OF THE INVENTION

Light-harvesting rods that absorb intensely across the visible spectrum and funnel the resulting excited-state energy to one end of the rod may find use in molecular-based solar cells (Loewe, R. S. et al., *J. Mater. Chem.* 2002, 12, 1530–1552). A number of general challenges must be met to achieve effective light-harvesting rods of this type, including (1) spectral matching of the absorption with the incident light, (2) appropriate electronic coupling of the pigments, and (3) solubility of the rods and precursors to the rods. The approach we have employed has focused on covalently linked arrays of porphyrins wherein the linker joining the porphyrins provides weak electronic coupling between the porphyrins. Weak coupling refers to the close similarity of the respective absorption spectra (associated with the first excited singlet state) and electrochemical potentials of the component parts and those of the components upon incorporation in the dyad or oligomer. Weak coupling enables rational design based on knowledge of the properties of the component building blocks (Holten, D. et al., *Acc. Chem. Res.* 2002, 35, 57–69). Despite the weak coupling, energy transfer in a porphyrin-based light-harvesting array can be exceptionally fast and efficient (del Rosario Benites, M. et al., *J. Mater. Chem.* 2002, 12, 65–80).

The synthesis of linear multiporphyrin rods has been pursued by methods employing the stepwise incorporation of porphyrin units, by polymerization methods, and by combinations of the two approaches. The stepwise methods generally have afforded arrays comprised of eight or fewer porphyrins along the axis of the rod (Loewe, R. S. et al., *J. Mater. Chem.* 2002, 12, 1530–1552; del Rosario Benites, M. et al., *J. Mater. Chem.* 2002, 12, 65–80; Burrell, A. K. et al., *Chem. Rev.* 2001, 101, 2751–2796). The polymerization methods have afforded a variety of architectures, including pendant (Aota, H. et al., *Chem. Lett.* 1994, 2043–2046), cofacial (Shimidzu, T. *Synth. Met.* 1996, 81, 235–241), or backbone polymers (Anderson, H. L. *Chem. Commun.* 1999, 2323–2330; Yamamoto, T. et al., *Macromolecules* 2000, 33, 5988–5994; Scamporrino, E. and Vitalini, D. *Macromolecules* 1992, 25, 1625–1632; Maruyama, H. et al., *Synth. Met.* 1998, 96, 141–149; Jiang, B. et al., *Chem. Commun.* 1998, 213–214; Jiang, B. and Jones, W. J. Jr. *Macromolecules* 1997, 30, 213–214; Jiang, B. et al., *Chem. Mater.* 1997, 9, 2031–2034; Ferri, A. et al., *J. Chem. Soc., Dalton Trans.* 1998, 4063–4069). Osuka has employed the combined synthetic approach to prepare linear meso,meso-linked porphyrins containing up to 128 porphyrins (Aratani, N. et al., *Angew. Chem. Int. Ed. Engl.* 2000, 39, 1458–1462; Aratani, N. and Osuka, A. *Macromol. Rapid Commun.* 2001, 22, 725–740). The meso,meso-linked porphyrins are very tightly coupled electronically but also present a rare example of a highly soluble long linear polymer of porphyrins (Nakano, A. et al., *Chem. Eur. J.* 2000, 6, 3254–3271). Regardless of synthetic method, the use of porphyrins in light-harvesting rods typically presents two problems: poor solubility and limited spectral coverage across the solar spectrum.

Poor solubility limits the ability to handle the porphyrin arrays and also crimps the length of rods that can be created. One approach to ameliorate the poor solubility of multiporphyrin arrays has been to suppress cofacial aggregation of the porphyrins by incorporating bulky groups at the meso-positions of the porphyrins, such as 3,5-di-tert-butyl phenyl groups (Crossley, M. J. and Burn, P. L. *J. Chem. Soc., Chem. Commun.* 1987, 39–40; Tamiaki, H. et al., *Bull. Chem. Soc. Jpn.* 1993, 66, 2633–2637) or 2,6-disubstituted aryl groups (Lindsey, J. S. and Wagner, R. W. *J. Org. Chem.* 1989, 54, 828–836; Wagner, R. W. et al., *Tetrahedron* 1994, 50, 11097–11112; Prathapan, S. et al., *J. Am. Chem. Soc.* 1993, 115, 7519–7520). The latter approach has led to the use of mesityl-substituted porphyrins (e.g., meso-tetramesitylporphyrin, TMP), which generally have greater solubility than phenyl-substituted porphyrins (e.g., meso-tetraphenylporphyrin, TPP). However, our attempts to use mesityl-substituted porphyrin building blocks (e.g., 1) in polymerizations resulted in insoluble oligomeric products. The replacement of the methyl groups in TMP with ethyl groups (2) led to only marginal changes in solubility. Use of very bulky pentafluorobenzyloxy groups led to increased solubility (3, 4) but still the resulting oligomers, obtained by polymerization alone or in the presence of the capping agent 5, were quite insoluble (Scheme 1).

The limited spectral coverage provided by porphyrins across the solar spectrum is an intrinsic property of the porphyrin chromophore. Porphyrins absorb intensely in the near-UV region but absorb poorly across the remainder of the visible spectrum. By contrast, chlorins and bacteriochlorins both absorb strongly in the blue and red regions of the spectrum. The chlorin chromophore (a dihydroporphyrin) and bacteriochlorin chromophore (a tetrahydroporphyrin) form the basis for chlorophyll and bacteriochlorophyll in green plant and bacterial photosynthesis, respectively. Porphyrins have been widely employed in light-harvesting studies (Burrell, A. K. et al., *Chem. Rev.* 2001, 101, 2751–2796) because of the close structural similarity yet greater synthetic tractability of porphyrins versus chlorins or bacteriochlorins. One approach to increase the overall absorption efficiency of light-harvesting systems is to employ accessory pigments. A good accessory pigment for porphyrins would absorb light strongly in the trough (430–540 nm) between the porphyrin Soret (B) and Q-bands, transfer energy efficiently to the porphyrin, not engage in electron-transfer quenching with the photoexcited porphyrin, display good solubility in common organic solvents, and provide compatibility with a modular building block approach (Wagner, R. W. and Lindsey, J. S. *Pure Appl.*

Chem. 1996, 68, 1373–1380; Wagner, R. W. and Lindsey, J. S. *Pure Appl. Chem.* 1998, 70 (8), p. i).

We have previously employed boron-dipyrrin dyes to serve as accessory pigments in porphyrin-based devices, including a molecular photonic wire (Wagner, R. W. and Lindsey, J. S. *J. Am. Chem. Soc.* 1994, 116, 9759–9760), optoelectronic gates (Wagner, R. W. et al., *J. Am. Chem. Soc.* 1996, 118, 3996–3997; Ambroise, A. et al., *Chem. Mater.* 2001, 13, 1023–1034), and light-harvesting arrays (Li, F. et al., *J. Am. Chem. Soc.* 1998, 120, 10001–10017). Although the boron-dipyrrin dyes display many of the desirable attributes mentioned above, these dyes were found to exhibit two excited-state conformers with rather short lifetimes (~15 ps, ~500 ps) (Li, F. et al., *J. Am. Chem. Soc.* 1998, 120, 10001–10017). The presence of two conformers complicated analysis of the excited-state dynamics of the arrays. We also have employed rhodamine dyes (Lindsey, J. S. et al., *Tetrahedron* 1994, 50, 8941–8968) and cyanine dyes (Lindsey, J. S. et al., *Tetrahedron* 1989, 45, 4845–4866). However, both of the latter types of dyes are intrinsically charged, causing severe difficulties in purification. Others have employed carotenoids as accessory pigments (Gust, D. et al., *Acc. Chem. Res.* 2001, 34, 40–48). However, the very short excited-state lifetime (~1 ps) requires the carotenoid to be placed in very close proximity to the porphyrin in order to achieve efficient energy transfer.

We have investigated the use of perylene dyes as accessory pigments for porphyrins in perylene-porphyrin dyads (Miller, M. A. et al., *J. Org. Chem.* 2000, 65, 6634–6649; Prathapan, S. et al., *J. Phys. Chem. B* 2001, 105, 8237–8248; Yang, S. I. et al., *J. Phys. Chem. B* 2001, 105, 8249–8258; Yang, S. I. et al., *J. Mater. Chem.* 2001, 11, 2420–2430). As a general class, perylenes meet the criteria for light absorption in the trough between the porphyrin Soret (B) and Q-bands (Langhals, H. *Chem. Ber.* 1985, 118, 4641–4645) and have the requisite spectral properties for efficient Förster energy transfer (long fluorescence lifetime (Ford, W. E. and Kamat, P. V. *J. Phys. Chem.* 1987, 91, 6373–6380), high fluorescence quantum yield (Langhals, H. *Chem. Ber.* 1985, 118, 4641–4645; Rademacher, A. et al., *Chem. Ber.* 1982, 115, 2927–2934; Ebeid, E. M. et al., *J. Phys. Chem.* 1988, 92, 4565–4568), and respectable overlap of the fluorescence emission bands with the absorption bands of a zinc porphyrin). However, achieving efficient energy transfer without competing or subsequent electron-transfer quenching processes requires selection of the appropriate composition of the perylene, architecture of the linker, and perylene-linker attachment sites. In addition, the types of substituents on the perylene and the overall perylene-porphyrin architecture affect the solubility of the construct.

Accordingly, there remains a need for new compounds having appropriate properties for the synthesis of light harvesting rods and light harvesting arrays, and for the construction of solar cells.

SUMMARY OF THE INVENTION

A first aspect of the present invention is a light harvesting array, comprising: (a) a first substrate comprising a first electrode; and (b) a layer of light harvesting rods electrically coupled to the first electrode, each of the light harvesting rods comprising a polymer of Formula I:

$$X^1\text{---}(X^{m+1})_m \tag{I}$$

wherein:
m is at least 1;
$X^1$ is a charge separation group having an excited-state of energy equal to or lower than that of $X^2$;

$X^2$ through $X^{m+1}$ are chromophores; and
at least one of $X^2$ through $X^{m+1}$ has at least one perylene group coupled thereto.

A second aspect of the present invention is a solar cell, comprising: (a) a light harvesting array as described above, and (b) a second substrate comprising a second electrode, with the first and second substrate being positioned to form a space therebetween, and with at least one of (i) the first substrate and the first electrode and (ii) the second substrate and the second electrode being transparent. Preferably there is also included (c) an electrolyte in the space between the first and second substrates.

A third aspect of the present invention is a composition useful for the manufacture of a light harvesting array, comprising: (a) a non-polar organic solvent; and (b) light harvesting rods solubilized in the organic solvent, the light harvesting rods comprising a polymer of Formula I as described above.

A further aspect of the present invention is a method of making a composition useful for the manufacture of light harvesting arrays as described above, the method comprising the steps of: (a) providing a mixture of a $X^1$ through $X^{m+1}$ as monomers in the organic solvent with an amine and a catalyst; (c) polymerizing the monomers in the mixture to produce a polymer of Formula I; and then (c) separating amine and catalyst from the mixture to provide a mixture having the polymer of Formula I solubilized therein.

A further aspect of the present invention is a compound according to Formula

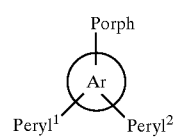

II wherein:
Ar is an aromatic group;
Porph is a porphyrinic macrocycle;
Peryl$^1$ is a first perylene group; and
Peryl$^2$ is a second perylene group.

A still further aspect of the present invention is a compound according to Formula III:

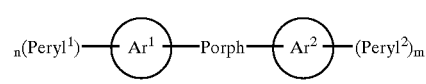

III wherein:
Ar$^1$ is a first aromatic group;
Ar$^2$ is a second aromatic group;
Porph is a porphyrinic macrocycle;
Peryl$^1$ is a perylene group;
Peryl$^2$ is a second perylene group;
m is from 1 to 3; and
n is from 1 to 3.

The present invention is explained in greater detail in the drawings herein and the specification set forth below.

DETAILED DESCRIPTION OF THE PREFERRED EMBODIMENTS

Figure 1:
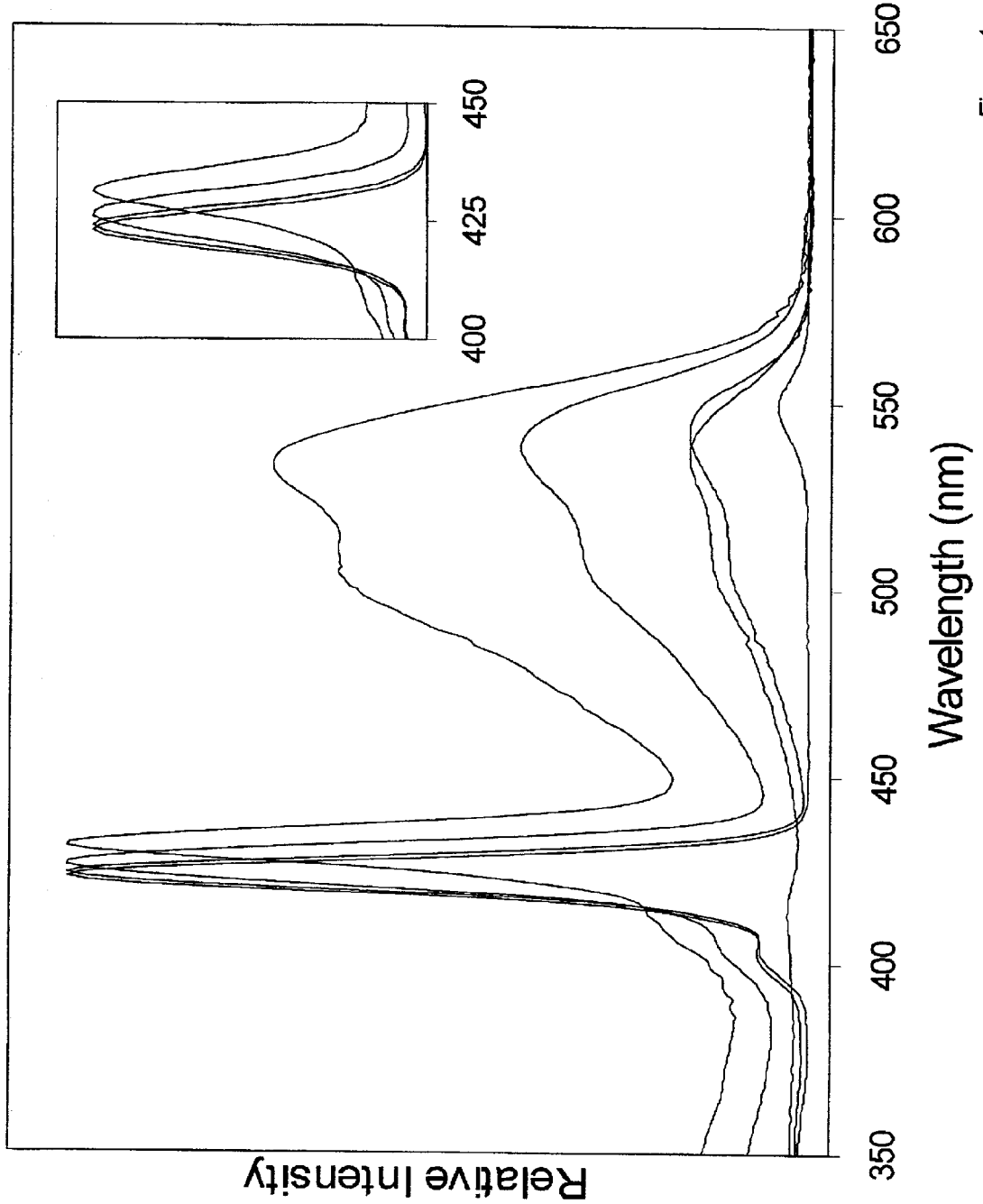
FIG. 1. Absorption spectra at room temperature in toluene of perylene-porphyrin arrays 9–11, porphyrin 17, and perylene PMI-12'. The spectra are identified in order of decreasing intensity at 550 nm as 11, 10, 9, PMI-12', and 17.

Among other things, we here present the synthesis of perylene-porphyrin building blocks and their use in Glaser, Sonogashira, or Suzuki polymerizations. In certain embodiments the building blocks bear synthetic handles (4-ethynylphenyl, 4-iodophenyl, bromo) at the trans (5, 15) meso-positions of a zinc porphyrin, and contain one, two, or four perylene-monoimide dyes attached at the 2- or 3,5- positions of the non-linking meso-aryl rings of the porphyrin. In certain embodiments each perylene bears one (9-position) or three (1, 6, and 9-positions) 4-tert-butylphenoxy substituents and zero or two isopropyl groups on the N-aryl unit for increased solubility. In each case the intervening linker is a diarylethyne unit that bridges the N-imide position of the perylene and the meso-position of the porphyrin. The choice of perylene, linker, and site of attachment to the perylene has emerged from a systematic study of a number of perylene-porphyrin constructs. In certain embodiments, the perylene-porphyrin building blocks were prepared using two approaches: (1) Sonogashira coupling of an ethynyl $A_3B$-porphyrin and a bromoperylene, or (2) reaction of a perylene-dipyrromethane with an aldehyde yielding a trans-$A_2B_2$-porphyrin, or with a dipyrromethane-dicarbinol yielding a trans-$AB_2C$-porphyrin or ABCD-porphyrin. Reactions of the building blocks under Glaser, Sonogashira, or Suzuki coupling conditions yielded perylene-porphyrin oligomers joined via 4,4'-diphenylbutadiyne (dpb), 4,4'-diphenylethyne (dpe), or 1,4-phenylene linkers (p), respectively. The tris(4-tert-butylphenoxy)perylene-porphyrin systems afforded soluble oligomers, while the mono-substituted (4-tert-butylphenoxy)perylene-porphyrin system produced insoluble materials. In certain embodiments the combination of perylenes and a porphyrin in a modular building block provides superior spectral coverage and greater solubility than is achieved with the use of porphyrins alone. The soluble perylene-porphyrin arrays generally constitute light-harvesting materials for use in molecular-based solar cells.

I. Definitions

The following terms and phrases are used herein:

A substrate as used herein is preferably a solid material (which may be flexible or rigid) suitable for the attachment of one or more molecules. Substrates can be formed of materials including, but not limited to glass, organic polymers, plastic, silicon, minerals (e.g. quartz), semiconducting materials, ceramics, metals, etc. The substrate may be in any suitable shape, including flat, planar, curved, rod-shaped, etc. The substrate may be inherently conductive and serve itself as an electrode, or an electrode may be formed on or connected to the substrate by any suitable means (e.g., deposition of a gold layer on a conductive oxide layer). Either or both of the substrates in the solar cells may be transparent (that is, wavelengths of light that excite the chromophores can pass through the substrate and corresponding electrode, even if they are visually opaque). In light-harvesting arrays, the substrate and electrode may be of any type. One of the substrates may be opaque with respect to the wavelengths of light that excite the chromophores. One of the substrates may be reflective or provided with a reflective coating so that light that passes through the arrays or rods is reflected back to the arrays or rods.

The term "electrode" refers to any medium capable of transporting charge (e.g. electrons) to and/or from a light harvesting rod. Preferred electrodes are metals, non-metals (e.g., conductive and semiconductive oxides), and conductive organic molecules. The electrodes can be manufactured to virtually any 2-dimensional or 3-dimensional shape.

The term "conductive oxide" as used herein refers to any suitable conductive oxide including binary metal oxides such as tin oxide, indium oxide, titanium oxide, copper oxide, and zinc oxide, or ternary metal oxides such as strontium titanate and barium titanate. Other examples of suitable conductive oxides include but are not limited to indium tin oxide, titanium dioxide, tin oxide, gallium indium oxide, zinc oxide, and zinc indium oxide. The metal oxide semiconductors may be intrinsic or doped, with trace amounts of materials, to control conductivity.

The term "heterocyclic ligand" as used herein generally refers to any heterocyclic molecule consisting of carbon atoms containing at least one, and preferably a plurality of, hetero atoms (e.g., N, O, S, Se, Te), which hetero atoms may be the same or different. Such heterocyclic ligands are typically macrocycles, particularly tetrapyrrole derivatives such as the phthalocyanines, porphyrins, and porphyrazines.

The term "perylene" as used herein refers to both substituted and unsubstituted perylenes, with substituted perylenes, including compounds substituted 1 or more times with groups such as alkoxy and aryloxy groups (e.g., phenoxy, such as 4-tert-butyl phenoxy) currently preferred.

The term "porphyrinic macrocycle" refers to a porphyrin or porphyrin derivative. Such derivatives include porphyrins with extra rings ortho-fused, or ortho-perifused, to the porphyrin nucleus, porphyrins having a replacement of one or more carbon atoms of the porphyrin ring by an atom of another element (skeletal replacement), derivatives having a replacement of a nitrogen atom of the porphyrin ring by an atom of another element (skeletal replacement of nitrogen), derivatives having substituents other than hydrogen located at the peripheral (meso-, β-) or core atoms of the porphyrin, derivatives with saturation of one or more bonds of the porphyrin (hydroporphyrins, e.g., chlorins, bacteriochlorins, isobacteriochlorins, decahydroporphyrins, corphins, pyrrocorphins, etc.), derivatives obtained by coordination of one or more metals to one or more porphyrin atoms (metalloporphyrins), derivatives having one or more atoms, including pyrrolic and pyrromethenyl units, inserted in the porphyrin ring (expanded porphyrins), derivatives having one or more groups removed from the porphyrin ring (contracted porphyrins, e.g., corrin, corrole) and combinations of the foregoing derivatives (e.g phthalocyanines, porphyrazines, naphthalocyanines, subphthalocyanines, and porphyrin isomers). Preferred porphyrinic macrocycles comprise at least one 5-membered ring.

The term "porphyrin" refers to a cyclic structure typically composed of four pyrrole rings together with four nitrogen atoms and two replaceable hydrogens for which various metal atoms can readily be substituted. A typical porphyrin is hemin.

A "chlorin" is essentially the same as a porphyrin, but differs from a porphyrin in having one partially saturated pyrrole ring. The basic chromophore of chlorophyll, the green pigment of plant photosynthesis, is a chlorin.

A "bacteriochlorin" is essentially the same as a porphyrin, but differs from a porphyrin in having two partially saturated non-adjacent (i.e., trans) pyrrole rings.

An "isobacteriochlorin" is essentially the same as a porphyrin, but differs from a porphyrin in having two partially saturated adjacent (i.e., cis) pyrrole rings.

The terms "sandwich coordination compound" or "sandwich coordination complex" refer to a compound of the formula $L^n M^{n-1}$, where each L is a heterocyclic ligand such as a porphyrinic macrocycle, each M is a metal, n is 2 or more, most preferably 2 or 3, and each metal is positioned between a pair of ligands and bonded to one or more hetero atom (and typically a plurality of hetero atoms, e.g., 2, 3, 4, 5) in each ligand (depending upon the oxidation state of the metal). Thus sandwich coordination compounds are not organometallic compounds such as ferrocene, in which the metal is bonded to carbon atoms. The ligands in the sandwich coordination compound are generally arranged in a stacked orientation (i.e., are generally cofacially oriented and axially aligned with one another, although they may or may not be rotated about that axis with respect to one another). See, e.g., D. Ng and J. Jiang, Sandwich-type heteroleptic phthalocyaninato and porphyrinato metal complexes, *Chemical Society Reviews* 26, 433–442 (1997). Sandwich coordination compounds may be "homoleptic" (wherein all of the ligands L are the same) or "heteroleptic" (wherein at least one ligand L is different from the other ligands therein). Examples include double-decker and triple-decker sandwich coordination compounds.

The term "multiporphyrin array" refers to a discrete number of two or more covalently-linked porphyrinic macrocycles. The multiporphyrin arrays can be linear, cyclic, or branched, but are preferably linear herein. Light harvesting rods herein are preferably multiporphyrin arrays. The light harvesting rods or multiporphyrin arrays may be linear (that is, all porphyrinic macrocycles may be linked in trans) or may contain one or more bends or "kinks" (that is, one or more cis-oriented linkers in a particular porphyrinic macrocycle) Some of the porphyrinic macrocycles may further include additional ligands, particularly porphyrinic macrocycles, to form sandwich coordination compounds as described further below. The rods are optionally but preferably are oriented substantially perpendicularly to either, and most preferably both, of the first and second electrodes.

"Chromophore" means a light-absorbing unit which can be a unit within a molecule or can comprise the entire molecule. Typically a chromophore is a conjugated system (alternating double and single bonds which can include non-bonded electrons but is not restricted to alternating double and single bonds, since mixtures of alternating triple/double and single bonds also constitute chromophores. A double or triple bond alone constitutes a chromophore. Heteroatoms can be included in a chromophore.). Examples of chromophores include the cyclic 18 pi-electron conjugated system that imparts color to porphyrinic pigments, the linear system of alternating double and single bonds in the visual pigment retinal, or the carbonyl group in acetone.

"Charge separation group" and "charge separation unit" refer to molecular entities that upon excitation (by direct absorption or energy transfer from another absorber) displace an electron to another part of the same molecule, or transfer an electron to a different molecule, semiconductor, or metal. The "charge separation group" and "charge separation unit" results in storage of some fraction of the excited state energy upon displacement or transfer of an electron. Typically the "charge separation group" and "charge separation unit" is located at the terminus of a light-harvesting array or rod, from which excited-state energy is received. The "charge separation group" and "charge separation unit" facilitates or causes conversion of the excited-state energy into a separate electron and hole or an electron-hole pair. The electron can be injected into the semiconductor by the "charge separation group" or "charge separation unit". It is feasible that the "charge separation group" and "charge separation unit" could extract an electron from a different molecule or semiconductor, thereby creating a negative charge on the "charge separation group" and "charge separation unit" and a hole in the other molecule or semiconductor. The reaction center of bacterial photosynthesis is a premier example of a "charge separation group" or "charge separation unit". Synthetic porphyrin-quinone or porphyrin-buckyball molecules also function to absorb light and utilize the resulting energy to separate charge.

The term "substituent" as used in the formulas herein, particularly designated by S or $S^n$ where n is an integer, in a preferred embodiment refer to electron-rich or electron-deficient groups (subunits) that can be used to adjust the redox potential(s) of the subject compound. Preferred substituents include, but are not limited to, H, aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, amido, and carbamoyl. In preferred embodiments, a substituted aryl group is attached to a porphyrin or a porphyrinic macrocycle, and the substituents on the aryl group are selected from the group consisting of aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, amido, and carbamoyl. Additional substituents include, but are not limited to, 4-chlorophenyl, 4-trifluoromethylphenyl, and 4-methoxyphenyl. Preferred substituents provide a redox potential range of less than about 5 volts, preferably less than about 2 volts, more preferably less than about 1 volt.

The term "aryl" refers to a compound whose molecules have the ring structure characteristic of benzene, naphthalene, phenanthrene, anthracene, etc. (i.e., either the 6-carbon ring of benzene or the condensed 6-carbon rings of the other aromatic derivatives). For example, an aryl group may be phenyl ($C_6H_5$) or naphthyl ($C_{10}H_7$). It is recognized that the aryl group, while acting as substituent can itself have additional substituents (e.g. the substituents provided for $S^n$ in the various formulas herein).

The term "alkyl" refers to a paraffinic hydrocarbon group which may be derived from an alkane by dropping one hydrogen from the formula. Examples are methyl ($CH_3$—), ethyl ($C_2H_5$—), propyl ($CH_3CH_2CH_2$—), isopropyl (($CH_3$)$_2$CH—).

The term "halogen" refers to one of the electronegative elements of group VIIA of the periodic table (fluorine, chlorine, bromine, iodine, astatine).

The term "perfluoroalkyl" refers to an alkyl group where every hydrogen atom is replaced with a fluorine atom.

The term "perfluoroaryl" refers to an aryl group where every hydrogen atom is replaced with a fluorine atom.

The term "pyridyl" refers to an aryl group where one CR unit is replaced with a nitrogen atom.

The term "sulfoxyl" refers to a group of composition RS(O)— where R is some alkyl, aryl, cycloalkyl, perfluoroalkyl, or perfluoroaryl group. Examples include, but are not limited to methylsulfoxyl, phenylsulfoxyl, etc.

The term "sulfonyl" refers to a group of composition $RSO_2$— where R is some alkyl, aryl, cycloalkyl, perfluoroalkyl, or perfluoroaryl group. Examples include, but are not limited to methylsulfonyl, phenylsulfonyl, p-toluenesulfonyl, etc.

The term "carbamoyl" refers to the group of composition $R^1(R^2)NC(O)$— where $R^1$ and $R^2$ are H or some alkyl, aryl, cycloalkyl, perfluoroalkyl, or perfluoroaryl group. Examples include, but are not limited to N-ethylcarbamoyl, N,N-dimethylcarbamoyl, etc.

The term "amido" refers to the group of composition $R^1CON(R^2)$— where $R^1$ and $R^2$ are H or some alkyl, aryl, cycloalkyl, perfluoroalkyl, or perfluoroaryl group. Examples include, but are not limited to acetamido, N-ethylbenzamido, etc.

The term "acyl" refers to an organic acid group in which the —OH of the carboxyl group is replaced by some other substituent (RCO—). Examples include, but are not limited to acetyl, benzoyl, etc.

In preferred embodiments, when a metal is designated by "M" or "$M^n$", where n is an integer, it is recognized that the metal may be associated with a counterion.

A linker is a molecule used to couple two different molecules, two subunits of a molecule, or a molecule to a substrate. When all are covalently linked, they form units of a single molecule.

The term "electrically coupled" when used with reference to a light harvesting rod and electrode, or to chromophores, charge separation groups and electrodes, refers to an association between that group or molecule and the coupled group or electrode such that electrons move from the storage medium/molecule to the electrode or from the electrode to the molecule and thereby alter the oxidation state of the storage molecule. Electrical coupling can include direct covalent linkage between the storage medium/molecule and the electrode, indirect covalent coupling (e.g. via a linker), direct or indirect ionic bonding between the storage medium/molecule and the electrode, or other bonding (e.g. hydrophobic bonding). In addition, no actual bonding may be required and the light harvesting rod may simply be contacted with the electrode surface. There also need not necessarily be any contact between the electrode and the light harvesting rod where the electrode is sufficiently close to the light harvesting rod to permit electron tunneling between the medium/molecule and the electrode.

"Excited-state energy" refers to the energy stored in the chromophore in a metastable state following absorption of light (or transfer of energy from an absorber). For an excited singlet (triplet) state, the magnitude of the "excited-state energy" is estimated by the energy of the shortest wavelength fluorescence (phosphorescence) band. The magnitude of the "excited-state energy" is greater than or equal to the energy of the separated electron and hole following charge separation.

Electrolytes used to carry out the present invention may be aqueous or non-aqueous electrolytes, including polymer electrolytes. The electrolyte may comprise or consist of a solid, in which latter case the solar cell can be produced devoid of liquid in the space between the first and second substrates. The electrolyte consists of or comprises a substance that increases the electrical conductivity of a carrier medium. Most electrolytes are salts or ionic compounds. Examples include sodium chloride (table salt), lithium iodide, or potassium bromide in water; tetrabutylammonium hexafluorophosphate or tetraethylammonium perchlorate in acetonitrile or dichloromethane; or an ionic polymer in a gel.

"Mobile charge carriers" refers to an ion, molecule, or other species capable of translating charges (electrons or holes) between the, two electrodes in a solar cell. Examples of mobile charge carriers include, but are not limited to, iodide/triiodide, bromide, tetramethyl-1,4-phenylenediamine, tetraphenyl-1,4-phenylenediamine, p-benzoquinone, $C_{60}$, $C_{70}$, pentacene, tetrathiafulvalene, and methyl viologen.

II. General Overview

A. Arrays and solar cells. As noted above, the present invention provides a light harvesting array, comprising: (a) a first substrate comprising a first electrode; and (b) a layer of light harvesting rods electrically coupled to the first electrode, each of the light harvesting rods comprising a polymer of Formula I:

$$X^1\text{-}(X^{m+1})_m \qquad (I)$$

wherein: m is at least 1 (for example, from 2, 3, or 4 to 49, 74 or 99 or more); $X^1$ is a charge separation group having an excited-state of energy equal to or lower than that of $X^2$ (e.g., a porphyrinic macrocycle, a chlorin, bacteriochlorin or isobacteriochlorin, a double or triple decker sandwich coordination compound); and $X^2$ through $X^{m+1}$ are chromophores (e.g., porphyrinic macrocycles). Where $X^1$ or $X^2$ through $X^{m+1}$ are porphyrinic macrocycles, some or all thereof are preferably meso-linked or beta-linked, and more preferably are trans meso-linked or trans beta-linked, porphyrinic-macrocycles.

Preferably, at least one of $X^2$ through $X^{m+1}$ has at least one perylene group coupled thereto, as discussed further below. More particularly, in some embodiments at least one (e.g., 2, 3, all) of $X^2$ through $X^{m+1}$ has at least two (e.g., 2, 3 or 4) perylene groups coupled thereto. The perylene groups may be different or the same, and are preferably either perylene mono-imide or perylene bis(imide) groups. Perylene mono-imides are currently preferred. Each of the perylene groups may be coupled to $X^2$ through $X^{m+1}$ through the perylene N-imide position, or through the perylene 1, 6, 9, or 11 positions.

In general, $X^1$ through $X^{m+1}$ are preferably selected so that, upon injection of either an electron or hole from $X^1$ into the first electrode, the corresponding hole or electron from $X^1$ is transferred to at least $X^2$. The light harvesting rods are preferably oriented substantially perpendicularly to the first electrode.

The light-harvesting rods are in some embodiments intrinsic rectifiers of excited-state energy and in some embodiments intrinsic rectifiers of holes. In some embodiments, the light harvesting rods are not greater than 500 nanometers in length.

Solar cells of the present invention may be fabricated in accordance with techniques apparent from the disclosure herein and generally comprise (a) a light harvesting array as described above, and (b) a second substrate comprising a second electrode, with the first and second substrate being positioned to form a space therebetween, and with at least one of (i) the first substrate and the first electrode and (ii) the second substrate and the second electrode being transparent. The solar cells preferably include (c) an electrolyte in the space between the first and second substrates. The electrolyte itself may be aqueous or non-aqueous, and in some embodiments a mobile charge carrier may be included in the electrolyte. The electrolyte may be of any suitable material, such as a polymer, and may be of any suitable physical form, such as a liquid or solid. Hence, in some embodiments, the solar cell is devoid of liquid in the space between the first and second substrates. In some embodiments $X^1$ is electrically coupled to the first electrode, and in some embodiments $X^{m+1}$ is electrically coupled to the second electrode.

The solar cells may be electrically coupled to a circuit such as a resistive load (e.g., an electric motor, an amplifier, etc.) to provide any of a variety of electrical devices.

B. Compositions and methods. The present invention further provides compositions useful for the manufacture of light harvesting arrays as described above. The compositions generally comprise (a) a non-polar organic solvent; and (b) a suitable amount (e.g., from 1, 2 or 5 microMolar to 50, 100, 200 or 250 milliMolar or more) of light harvesting rods solubilized in the organic solvent, the light harvesting rods comprising a polymer of Formula I as described above. Any suitable solvent may be employed, including but not limited to tetrahydrofuran, toluene, chloroform, chlorobenzene, xylene, dichloromethane, mesitylene, 1,1,1-trichloroethane, 2-chloronaphthalene, 1,2-dichlorobenzene, 1,1,2,2-tetrachloroethane, and mixtures thereof. Such compositions are generally made by (a) providing a mixture of a $X^1$ through $X^{m+1}$ as monomers in the organic solvent with an amine and a catalyst; (c) polymerizing the monomers in the mixture to produce a polymer of Formula I; and then (c) separating amine and catalyst from the mixture to provide a mixture having the polymer of Formula I solubilized therein. Any suitable amine may be used, including but not limited to triethylamine, tripropylamine, tributylamine, N,N-diisopropylamine, N,N-diisopropylethylamine, pyridine, collidine, etc. Any suitable ource of Pd(0) may be used as a catalyst, including but not limited to $Pd_2(dba)_3$, $Pd(PPh_3)_4$, $Pd(PPh_3)_2Cl_2$, $Pd(OAc)_2$, etc. The reaction may be carried out at any suitable temperature, time and pressure, such as at 0–150° C. at ambient pressure for a time of up to 36 hours, in any suitable atmosphere, preferably a deoxygenated atmosphere achieved by use of an inert atmosphere such as Ar, $N_2$, etc., except for the Glaser reaction, which can be done in air.

C. Compounds. Preferred compounds described herein which may be used as monomers for carrying out the methods described above are, in general, compounds according to Formula II or Formula III:

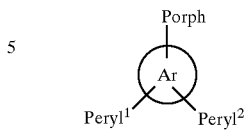

II wherein:
Ar is an aromatic group
Porph is a porphyrinic macrocycle as described above;
$Peryl^1$ is a first perylene group; and
$Peryl^2$ is a second perylene group; and

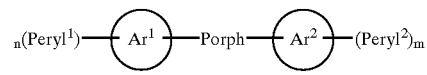

III wherein:
$Ar^1$ is a first aromatic group;
$Ar^2$ is a second aromatic group;
Porph is a porphyrinic macrocycle;
$Peryl^1$ is a perylene group;
$Peryl^2$ is a second perylene group;
m is 1, 2 or 3; and
n is 1, 2 or 3.

Aromatic groups Ar, $Ar^1$ and $Ar^2$ in Formulas II–III above may independently be any suitable aromatic group, such as benzene, thiophene, furan, pyrrole, pyridine, naphthalene, anthracene, phenanthrene, biphenyl, indene, quinoline, pyridazine, pyrimidine, pyrazine, fluorene, etc.

In preferred embodiments, Ar, $Ar^1$ and $Ar^2$ are benzene. Porphyrinic macrocycles may be as described above and perylene groups may be as described above. Where multiple perylene groups are contained on a single molecule those perylene groups may be the same or different. The perylene groups are, in general, preferably perylene mono-imides or perylene bis(mides) and are preferably coupled to the aromatic groups by or at the perylene N-imide position, or the perylene 1, 6, 9, or 11 positions. Such compounds may be produced in accordance with the techniques described below, or modifications thereof which will be apparent to those skilled in the art based upon the disclosure herein.

In particular embodiments of Formula II, the porphyrinic macrocycle comprises a porphyrin group that is substituted with Ar at the 5-position, X at the 10-position, Y at the 15-position, and Z at the 20-position. Y is an alkyl or aryl group and X and Z are independently selected substituents such as iodo, bromo, ethynyl, 2-(trimethylsilyl)ethynyl, 4-ethynylphenyl, 4-[2-(trimethylsilyl)ethynyl]phenyl, 4-iodophenyl, 4-bromophenyl, 4,4,5,5-tetramethyl-1,3,2-dioxaborolan-2-yl, or 4-(4,4,5,5-tetramethyl-1,3,2-dioxaborolan-2-yl)phenyl.

A particular group of compounds useful for carrying out the invention described herein are compounds of formula IV:

formula IV

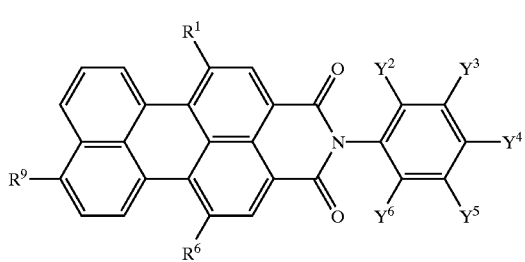

wherein:

$R^1$, $R^6$, and $R^9$ independently selected from the group consisting of H, alkyl, aryl, alkoxy, aryloxy, alkylthio, arylthio, halo, ethynylalkyl, ethynylaryl, dialkylboronate and trialkyltin; and $Y^2$, $Y^3$, $Y^4$, $Y^5$, and $Y^6$ are each independently selected from the group consisting of H, alkyl, aryl, alkoxy, aryloxy, alkylthio, arylthio, halo, ethynylalkyl, ethynylaryl, dialkylboronate, and trialkyltin.

In a particular embodiment of the compounds of formula IV, $Y^2$ and $Y^6$ are H or alkyl, $Y^4$ is halo, ethynyl, dialkylboronate, or trialkyltin; and $Y^3$ and $Y^5$ are H.

In another particular embodiment of the compounds of formula IV, $Y^2$, $Y^4$ and $Y^5$ are H, $Y^3$ is halo, ethynyl, dialkylboronate, or trialkyltin and $Y^6$ is alkyl.

Also useful for carrying out the present invention are compounds of formula V:

formula V

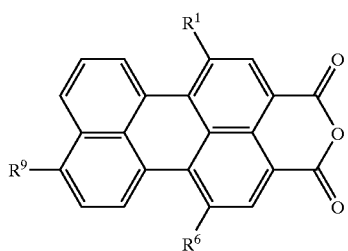

wherein:

$R^1$, $R^6$, and $R^9$ are independently selected from the group consisting of H, alkyl, aryl, alkoxy, aryloxy, alkylthio, arylthio, halo, ethynylalkyl, ethynylaryl, dialkylboronate, and trialkyltin.

A particular group of compounds useful for carrying out the present invention are compounds of formula VI:

VI

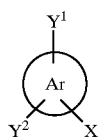

wherein Ar is an aromatic group as described in connection with formula II above, such as benzene $Y^1$ and $Y^2$ are independently selected perylene mono-imide groups; and X is selected from the group consisting of formyl, halo, or 5-dipyrromethane. A particularly preferred embodiment is compounds of formula VIa VIa

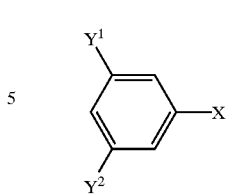

wherein X, $Y^1$ and $Y^2$ are as described above.

III. Detailed Description

In this application, we describe a novel solution to both problems of limited solubility and inadequate spectral coverage. The solution entails the attachment of accessory pigments (perylene dyes) to groups at the porphyrin perimeter such that the resulting accessory pigment-porphyrin architecture is soluble. This work is described in the following four sections:

In Part A, we describe the synthesis of perylene building blocks.

In Part B, we describe the synthesis of multiperylene-porphyrin arrays using the building blocks from Part A in order to assess the effects of clustering multiple perylenes around the porphyrin.

In Part C, we use the best multiperylene-porphyrin motif identified in Part B to prepare multiperylene-porphyrin building blocks.

In Part D, we employ the building blocks from Part C in polymerizations to make linear rods.

In Part E, we describe refined syntheses of perylene building blocks suitable for scale-up.

Part A. We employed perylene-monoimide and perylene-bis(imide) dyes (Prathapan, S. et al., *J. Phys. Chem. B* 2001, 105, 8237–8248; Yang, S. I. et al., *J. Phys. Chem. B* 2001, 105, 8249–8258; Yang, S. I. et al., *J. Mater. Chem.*, 2001, 11, 2420–2430; Miller, M. A. et al., *J. Org. Chem.* 2000, 65, 6634–6649) as accessory pigments for porphyrins. The benchmark perylene-monoimide and perylene-bis(imide) dyes are shown in Scheme 2. Both types of perylene dyes have strong absorption ($\epsilon_{\lambda max}$~50,000 M$^{-1}$ cm$^{-1}$) between the porphyrin Soret and Q bands. Introduction of bulky groups at the N-aryl moieties is necessary to achieve solubility in organic solvents, which is typically achieved by use of four tert-butyl groups (PDI-1) (Langhals, H. *Nachr. Chem. Tech. Lab.* 1980, 28, 716–718) or four isopropyl groups (PDI-2) (Quante, H. and Müllen, K. *Angew. Chem.* 1995, 107, 1487–1489). The absorption and emission characteristics of the perylene dyes are little affected by the presence of solubilizing substituents at the imide position because of the nodes present at the imide nitrogen in both the HOMO and LUMO (Langhals, H. et al., *Spectrochim. Acta* 1988, 44A, 1189–1193; Adachi, M. et al., *J. Phys. Chem.* 1995, 99, 14240–14246). The widely studied perylene-bis (imide) dye PDI-1, perylene-monoimide dye PMI-1, and their derivatives have found use as light absorbers, energy-transfer participants, and charge carriers.

Scheme 1
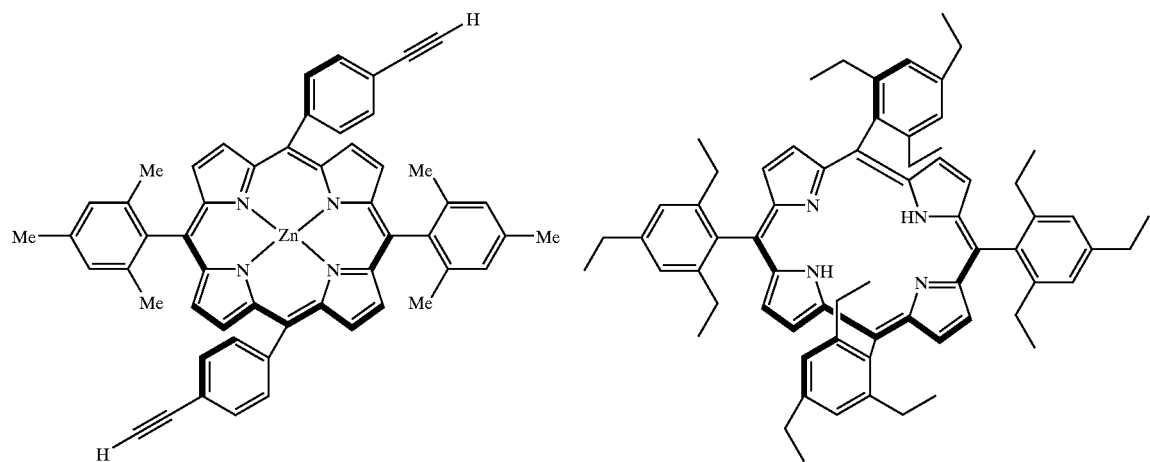
1      2
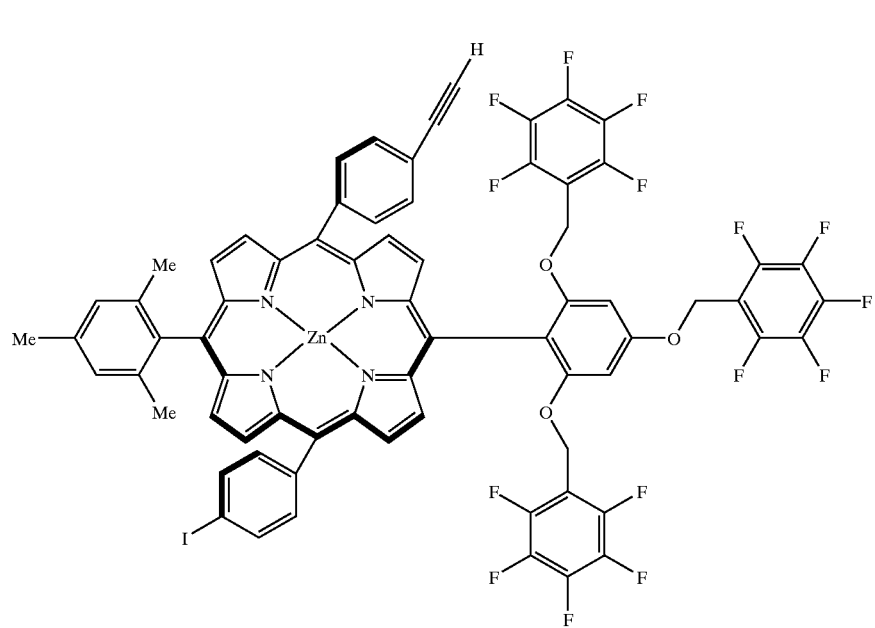
3

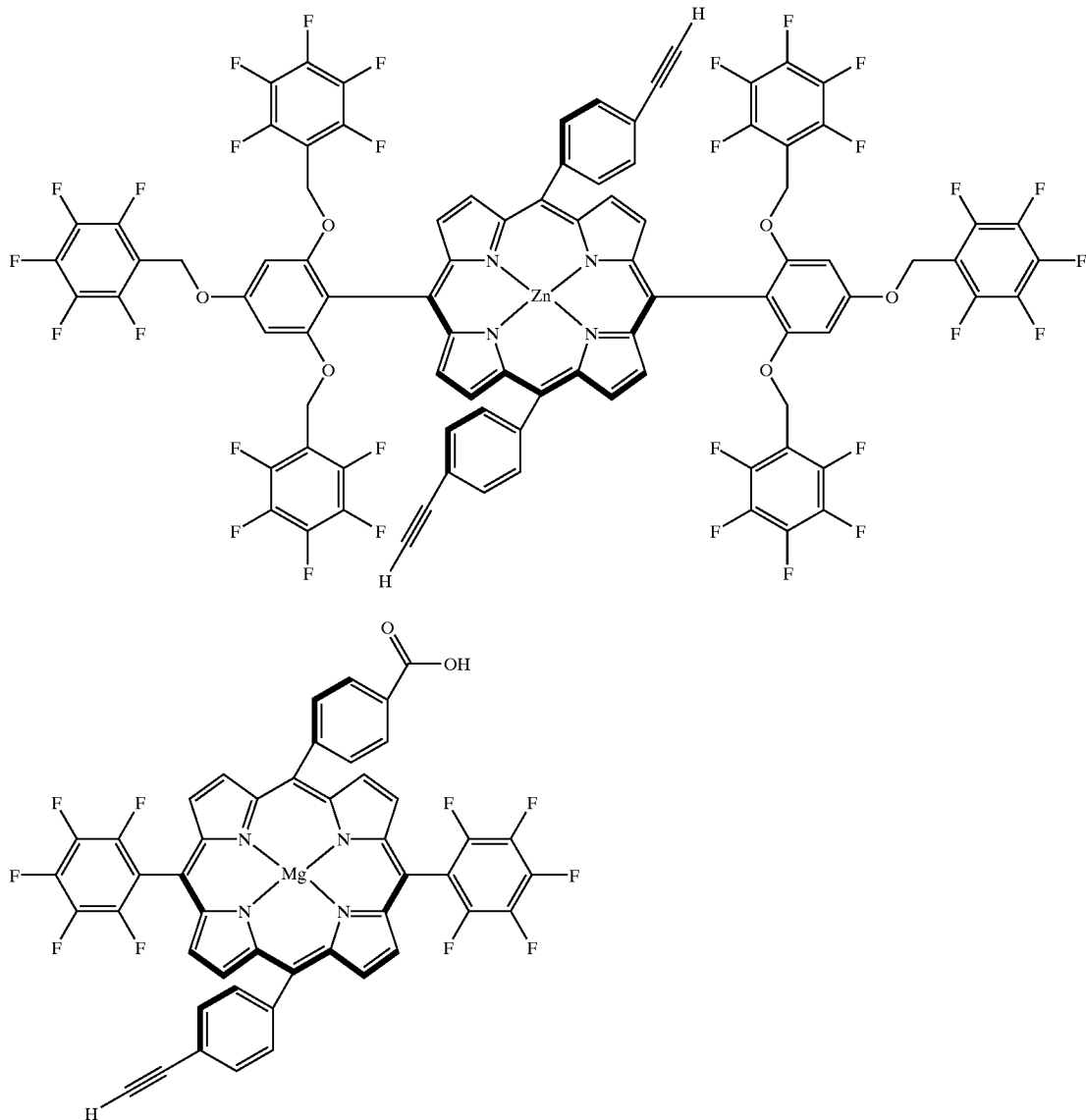

The preparation of covalently linked perylene-porphyrin dyads requires the synthesis of suitable perylene building blocks. Scheme 2 displays perylene-monoimide and perylene-bis(imide) building blocks that have been used previously. The choice of perylene building block can profoundly affect the properties of the resulting perylene-porphyrin dyads. For example, the perylene-bis(imide) building block PDI-3 produces perylene-porphyrin dyads that are joined at the N-aryl position, resulting in relatively weak through-bond electronic communication between the perylene and the porphyrin (Prathapan, S. et al., *J. Phys. Chem. B* 2001, 105, 8237–8248; Yang, S. I. et al., *J. Phys. Chem. B* 2001, 105, 8249–8258). On the other hand, perylene-monoimide building blocks (e.g., PMI-3, PMI-4) give rise to dyads that are linked at the 9-position of the perylene, yielding more extensive electronic coupling (Yang, S. I. et al., *J. Mater. Chem.*, 2001, 11, 2420–2430). In addition to altering the extent of electronic communication, these different types of linkages also change the center-to-center distance between perylene and porphyrin. Other perylene building blocks such as PMI-5 and PMA have been used as intermediates in the syntheses of all-optical molecular switches (Gosztola, D. et al., *J. Am. Chem. Soc.* 1998, 120, 5118–5119; Hayes, R. T. et al., *J. Am. Chem. Soc.* 2000, 122, 5563–5567). The presence of phenoxy substituents around the perylene core alters the electrochemical potentials of the perylene building block. Still other perylene building blocks have been prepared as intermediates in the synthesis of other chromophores. For example, the perylene building block PMI-6 was used in the synthesis of near-IR absorbing quaterrylene dyes (Quante, H. and Müllen, K. *Angew. Chem.* 1995, 107, 1487–1489), while the perylene building block PDI-4 has been used as a precursor to a family of coronene dyes (Rohr, U. et al., *Angew. Chem. Int. Ed.* 1998, 37, 1434–1437).

We have previously prepared and studied several perylene-porphyrin dyads through the use of perylene-monoimide or perylene-bis(imide) building blocks (Prathapan, S. et al., *J. Phys. Chem. B* 2001, 105, 8237–8248; Yang, S. I. et al., *J. Mater. Chem.*, 2001, 11, 2420–2430). Scheme 3 displays two such dyads. PMI-ep-Zn incorporates a perylene-monoimide dye joined at the 9-position of the perylene via an ethynylphenyl linker. PDI-pep-Zn consists of a perylene-bis(imide) dye joined at the N-imide position via a diphenylethyne (pep) linker (Yang, S. 1. et al., *J. Mater. Chem.*, 2001, 11, 2420–2430).

Scheme 2

(A) Perylene benchmarks

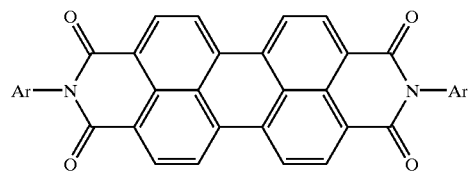

PDI-1

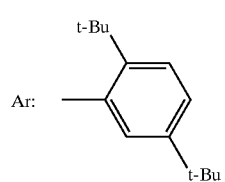

PDI-2

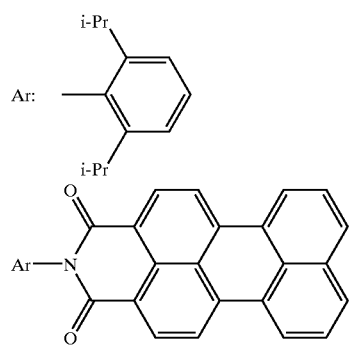

PMI-1

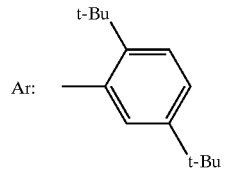

PMI-2

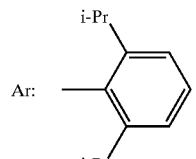

(B) Perylene building blocks

PDI-3

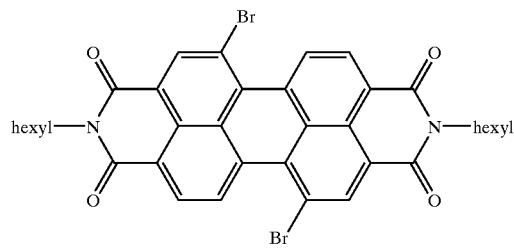

PDI-4

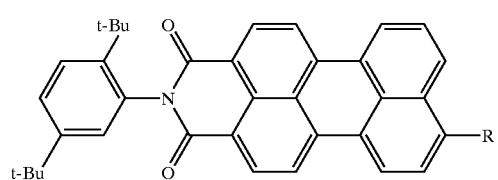

PMI-3; R = Br
PMI-4; R = ———≡———H

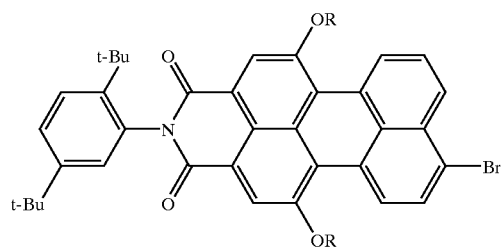

PMI-5; R = 4-tert-butylphenyl

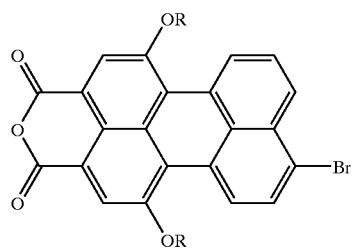

PMA; R = 4-tert-butylphenyl

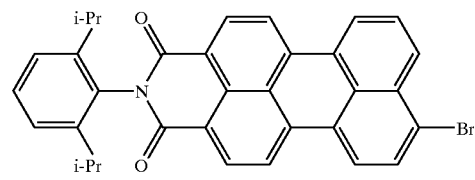

PMI-6

Scheme 3

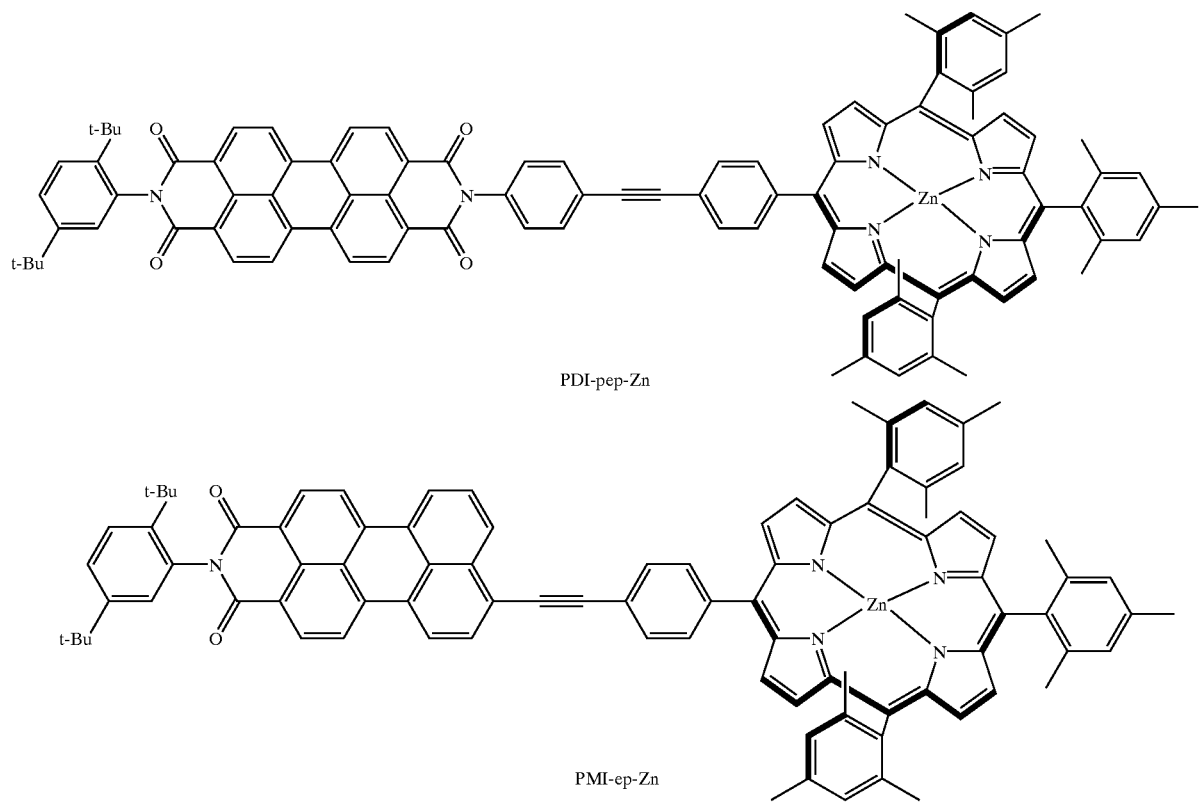

PMI-ep-Zn was found to undergo ultrafast ($k_{ENT}$>(0.5 ps)$^{-1}$) and essentially quantitative energy transfer from the excited perylene-monoimide (PMI*) to the ground-state porphyrin (forming the excited zinc porphyrin, Zn*). In toluene, the properties of the excited porphyrin (lifetime, fluorescence quantum yield, etc.) are basically unperturbed from those of the isolated pigment. Thus, following energy transfer, the excited porphyrin is not quenched by deleterious reactions involving the perylene, such as charge-transfer. However, in acetonitrile ultrafast charge transfer and charge recombination are the dominant photochemical pathways. In contrast, dyad PDI-pep-Zn exhibits electron-transfer quenching reactions in both polar and nonpolar solvents. The photoexcited perylene unit (PDI*) decays very rapidly (lifetimes of 2.5 (toluene) and 2.4 ps (acetonitrile)) by energy transfer to the porphyrin, forming PDI-pep-Zn* in high yield (80% in toluene; 20% in acetonitrile), and hole transfer to the porphyrin, forming PDI⁻-pep-Zn⁺ in lesser yield (20% in toluene; 30% in acetonitrile). In both toluene and acetonitrile, the Zn* excited-state subsequently decays with a lifetime of 0.4 ns primarily by electron transfer to the perylene.

In this section, we present the synthesis of several new perylene building blocks. In each case, the perylene dye is a monoimide derivative, the linker is attached to the 9- or N-imide position, and 0–3 phenoxy groups are incorporated for tailoring solubility and possible alteration of the electrochemical potentials. Perylene-monoimide dyes were chosen over the bis(imide) dyes because the former are less prone to electron-transfer quenching reactions (Yang, S. I. et al., *J. Mater. Chem.*, 2001, 11, 2420–2430). The ethynylphenyl linker at the 9-position is known to provide more extensive electronic communication than the diphenyl-ethyne linker at the N-imide position. We generally felt it was necessary to employ a linker design that would afford diminished through-bond electronic communication, thereby suppressing electron-transfer quenching reactions.

We previously developed a perylene bis(imide) dye (PDI-3) bearing an iodo substituent on the N-imide aryl ring as a convenient synthetic handle for Pd-mediated coupling reactions (Prathapan, S. et al., *J. Phys. Chem. B* 2001, 105, 8237–8248). However, the perylene-monoimide dyes previously available for such reactions have been incorporated in multichromophore architectures via ethynyl linkers at the perylene 9-position. The new perylene building blocks we have developed enable attachment via Pd-mediated coupling reactions at the N-imide aryl ring of the perylene-onoimide dye.

Synthesis of Perylene Building Blocks. Our first approach to prepare a perylene building block bearing a synthetic handle on the N-aryl unit began with 2,5-di-tert-butylaniline. Treatment of 2,5-di-tert-butylaniline with bromine in methanol afforded 4-bromo-2,5-di-tert-butylaniline in 97% yield. A possible isomer, 6-bromo-2,5-di-tert-butylaniline, was not detected. Treatment of 4-bromo-2,5-di-tert-butylaniline with 3,4:9,10-perylenetetracarboxylic dianhydride under the high-temperature conditions for forming the monoimide dye, employing molten imidazole in a sealed tube (Feiler, L. et al., *Liebigs Ann.* 1995, 1229–1244), failed to yield significant quantities of the brominated perylene-monoimide. Instead, the major product recovered was the debrominated analog, PMI-1. The steric hindrance between the bromine atom and the tert-butyl group may be such that thermal bond cleavage is a preferred reaction pathway under these conditions.

Accordingly, we decided to use 2,6-diisopropylaniline as the starting material to alleviate the steric hindrance at the 4-position. Perylene-imide dyes prepared from 2,6-diisopropylaniline exhibit high solubility and also exist in a single isomeric form as opposed to the diastereomers obtained with 2,5-di-tert-butylaniline (Feiler, L. et al., *Liebigs Ann.* 1995, 1229–1244). Treatment of 2,6-diisopropylaniline with bromine in methanol afforded 4-bromo-2,6-diisopropylaniline (6) in 79% yield. Treatment of 6 to the molten-imidazole conditions for forming the perylene monoimide afforded PMI-7 in 46% yield (Scheme 4). Importantly, no debrominated perylene side product was observed. Several other perylene building blocks were prepared from this versatile compound. Bromination of PMI-7 in chlorobenzene cleanly gave the 9-bromo derivative PMI-8 in 86% yield. The ease of this bromination must reflect the substantial electron density at this position in the HOMO of the perylene monoimide. Treatment of PMI-8 with 4-tert-butylphenol and potassium carbonate in refluxing DMF furnished the mono-phenoxy perylene building block PMI-9 in 81% yield. Significantly, no phenoxylation of the N-aryl bromide was detected. The final building block in this series was obtained by ethynylation of the N-aryl bromide. Reaction of PMI-9 and (trimethylsilyl)acetylene using Pd-mediated cross-coupling conditions (Wagner, R. W. et al., *Chem. Mater.* 1999, 11, 2974–2983) afforded perylene PMI-10 in 76% yield. Removal of the trimethylsilyl protecting group with $K_2CO_3$ gave the mono-phenoxy mono-ethyne perylene building block PMI-10' in 93% yield.

The synthesis of a perylene building block bearing three phenoxy groups is outlined in Scheme 5. Treatment of the monobromo perylene building block PMI-7 with excess bromine in refluxing chloroform afforded the tetrabromo perylene derivative PMI-11 in 59% yield. This compound was then treated with 4-tert-butylphenol and potassium carbonate in refluxing DMF for 1 h to furnish the tris(phenoxy), monobromo perylene building block PMI-12 in 68% yield. Like with the synthesis of PMI-9, no phenoxylation of the N-aryl bromide was observed.

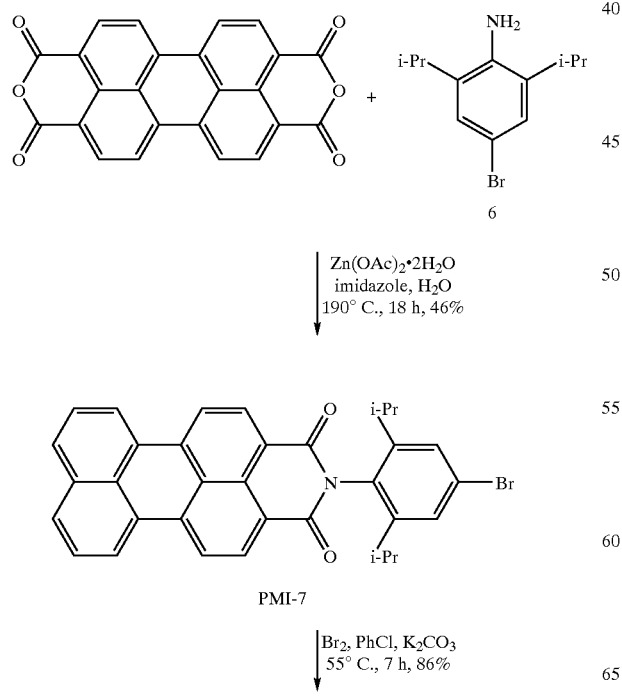

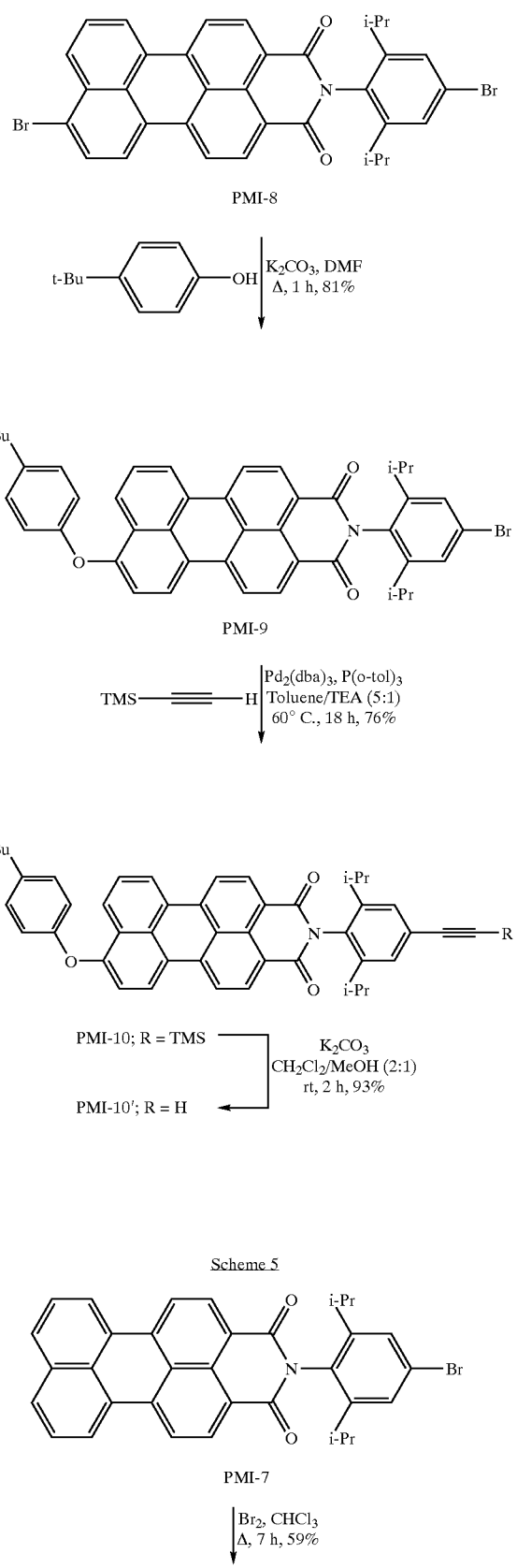

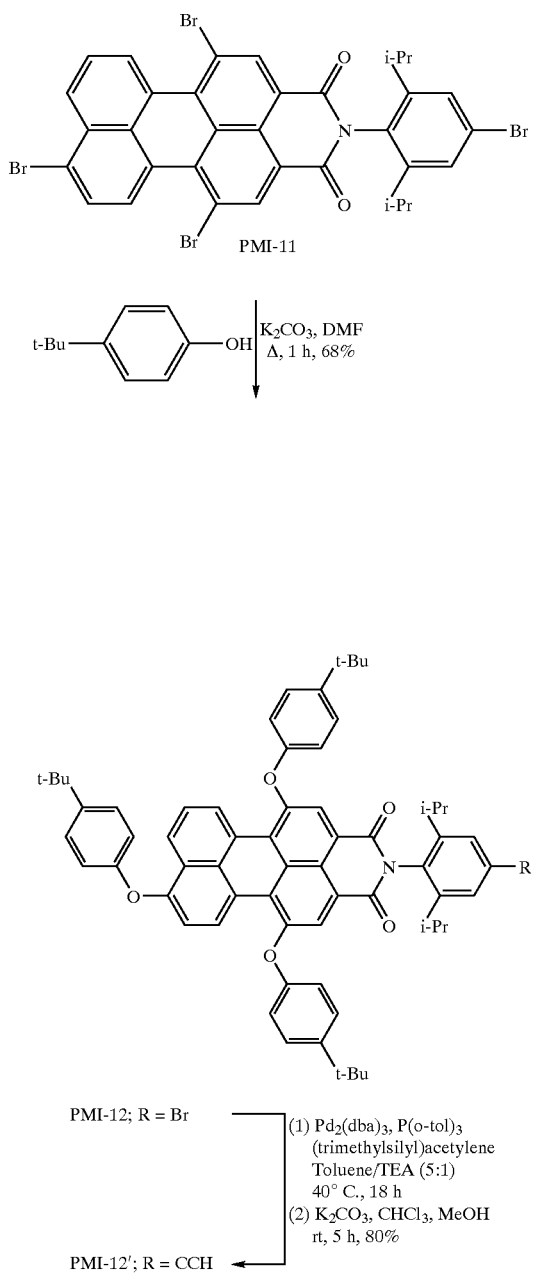

Perylene Benchmark Compounds. Several perylene-monoimide benchmark compounds were also prepared for use in this study. These benchmark compounds were used in electrochemical and photochemical studies and serve as reference compounds. These benchmarks are analogous to those building blocks used in the preparation of the perylene-porphyrin dyads with the exception that they lack the bromo substituent (which could hinder photochemical analysis). Bromoperylene building block PMI-12 was treated with (trimethylsilyl)acetylene under Pd-catalyzed cross-coupling conditions followed by removal of the trimethylsilyl group with $K_2CO_3$ to afford the perylene mono-ethynyl benchmark compound PMI-12' in 80% yield (Scheme 5). The perylene benchmark compound PMI-2 (Boehm, A. and Helfer, W. U.S. Pat. No. 5,808,073) was brominated at the 9-position, affording the known perylene building block, PMI-6 (Quante, H. and Müllen, K. *Angew. Chem.* 1995, 107, 1487–1489). Treatment of PMI-6 with 4-tert-butylphenol and potassium carbonate in refluxing DMF gave a fourth perylene benchmark compound, PMI-13 in 86% yield (Scheme 6). The perylene benchmarks thus comprise PMI-12', PMI-13, and the known compound PMI-2 (Boehm, A.; Helfer, W. U.S. Pat. No. 5,808,073).

Chemical Characterization. All perylene building blocks were analyzed by $^1H$ NMR spectroscopy. The very soluble perylenes PMI-10 and PMI-12 were also analyzed by $^{13}C$ NMR spectroscopy. The presence of the 2,6-diisopropyl groups facilitates NMR characterization due to the absence of regioisomers, which can exist with the 2,5-di-tert-butylphenyl moiety (Feiler, L. et al., *Liebigs Ann.* 1995, 1229–1244). Many of the perylene building blocks gave small but significant changes in the NMR spectra upon analysis at different concentrations in $CDCl_3$, which is likely due to perylene aggregation.

Part B. A major objective is to design soluble perylene-porphyrin building blocks that provide good spectral coverage, undergo energy transfer without competing electron-transfer reactions in non-polar or polar media, and can be elaborated into oligomeric structures. In Part I, perylene-monoimide dyes were prepared that (1) bear one or three 4-tert-butylphenoxy substituents and (2) can be linked to the porphyrin via a diarylethyne linker that bridges the perylene N-imide position and the porphyrin meso-position.

In this section, we present the synthesis and selected physical properties of several multiperylene-porphyrin light-harvesting arrays using the perylene-monoimide building blocks. The systems described contain 2, 4, or 8 perylene-monoimide accessory pigments joined to a zinc porphyrin. In each array, the perylenes are attached to the 2,6- or 3,5-positions of the meso-phenyl ring of the porphyrin via an arylethynylphenyl (aep) linker (Scheme 7). The resulting projection of the perylene out of the plane of the porphyrin should suppress cofacial aggregation of the porphyrins in solution, thereby affording highly soluble light-harvesting arrays. Isopropyl groups on the 2,6-positions of the aryl unit attached to the N-imide site cause the perylene and the N-aryl unit to be essentially perpendicular, thereby enhancing the solubility of the perylene dye. The photochemical properties of the arrays have been surveyed by static absorption and fluorescence measurements to identify suitable multiperylene-porphyrin constructs for further use.

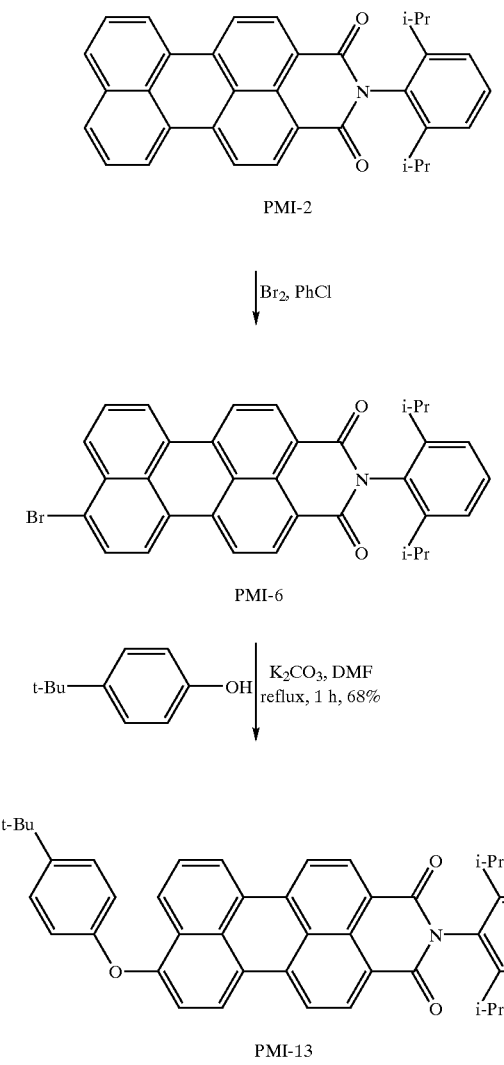
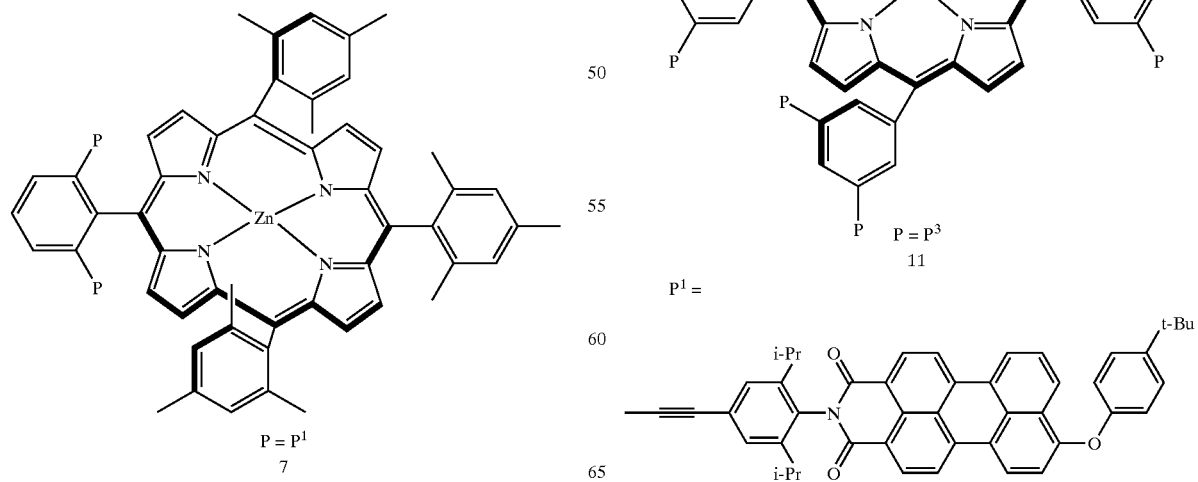

P³ =

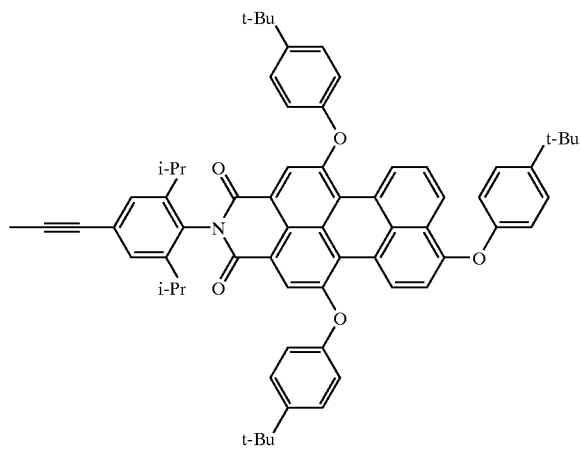

(1) Synthetic Strategies. The preparation of the multiperylene-porphyrin arrays follows one of two general strategies. In approach A, a bis(perylene)aldehyde is prepared by the Sonogashira coupling of a bromo- or ethynylperylene with a diethynyl- or dibromo-benzaldehyde. The resulting bis(perylene)aldehyde can then be used as a starting material in a mixed-aldehyde condensation (forming an $A_3B$-porphyrin), can be reacted with a dipyrromethane (forming a trans-$A_2B_2$-porphyrin), or can be reacted with pyrrole (forming an $A_4$-porphyhrin). In approach B, a mixed-aldehyde condensation affords a diethynyl $A_3B$-porphyrin, or reaction with a dipyrromethane affords a tetraethynyl trans-$A_2B_2$-porphyrin. Sonogashira coupling of the ethynylporphyrin with a suitable bromoperylene affords the perylene-porphyrin light-harvesting array. The two approaches differ only in the order of the Sonogashira and porphyrin-forming reactions. Both approaches have been used to prepare several types of perylene-porphyrin arrays.

(2) Synthesis of Convergent Perylene-Porphyrin Arrays. The positioning of a perylene-monoimide at the 2,6-positions of the meso-aryl ring of the tetraarylporphyrin was quite attractive as a means of covering the face of the porphyrin, thereby suppressing porphyrin-porphyrin aggregation. We decided to employ Approach B in the synthesis of this target perylene-porphyrin array. The Sonogashira coupling of commercially available 2,6-dichlorobenzaldehyde and (trimethylsilyl)acetylene was performed under the conditions developed by Buchwald and Fu (Hundertmark, T. et al., *Org. Lett.* 2000, 12, 1729–1731), which allow for the Sonogashira coupling of aryl bromides at room temperature (Scheme 8). We employed the catalytic system of $Pd(PhCN)_2Cl_2$, CuI, and $P(t-Bu)_3$ in dioxane containing diisopropylamine. The reaction was performed at 70° C. with an excess of (trimethylsilyl)acetylene (1.75 eq per chloride) to overcome the low reactivity of the aryl chlorides. Analysis of the crude reaction mixture by GC revealed no monocoupled product. Purification by filtration through silica, Kugelrohr distillation, and column chromatography afforded 12 in 37% yield.

Scheme 8

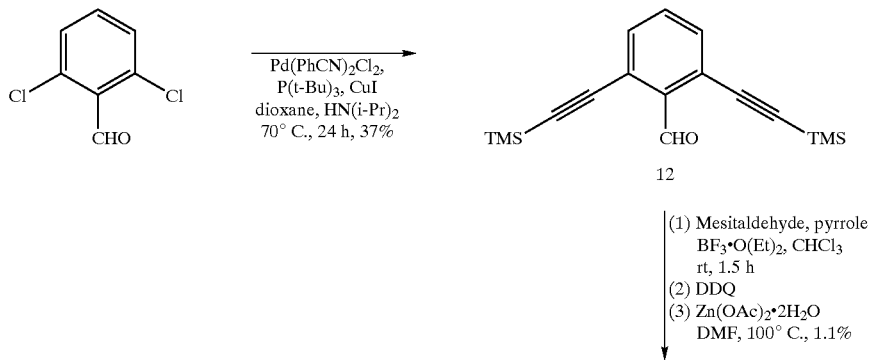

(1) Mesitaldehyde, pyrrole
    $BF_3 \cdot O(Et)_2$, $CHCl_3$
    rt, 1.5 h
(2) DDQ
(3) $Zn(OAc)_2 \cdot 2H_2O$
    DMF, 100° C., 1.1%

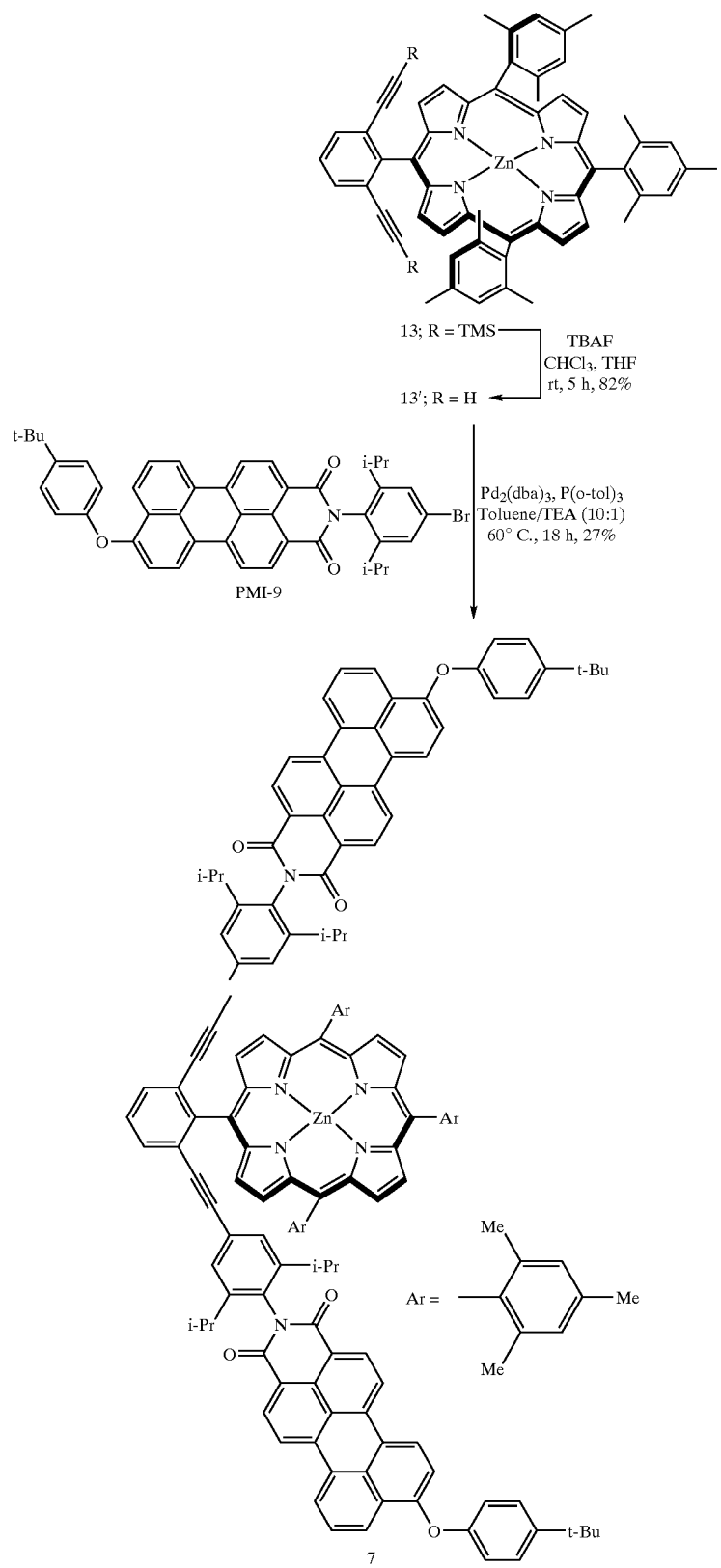

Aldehyde 12, mesitaldehyde, and pyrrole were then subjected to a mixed-aldehyde condensation with $BF_3 \cdot O(Et)_2$-ethanol cocatalysis (Lindsey, J. S. and Wagner, R. W. *J. Org. Chem.* 1989, 54, 828–836) in $CHCl_3$ at room temperature for 1.5 h followed by oxidation with DDQ. The resulting mixture of porphyrins was subjected to the standard conditions for zinc metalation (five equivalents of $Zn(OAc)_2 \cdot 2H_2O$ in $CHCl_3$/MeOH at room temperature) (Lindsey, J. S. et al., *Tetrahedron* 1994, 50, 8941–8968). However, these conditions failed to furnish the zinc chelate. Therefore, the metalation reaction was performed at 100° C. using DMF as solvent. Purification by column chromatography furnished meso-tetramesitylporphyrin as the dominant porphyrin product and the desired porphyrin 13 in only 1.1% yield. The very low yield with 2,6-diethynylbenzaldehyde is in accord with the low yields obtained with other aldehydes bearing large rigid groups at the 2,6-positions such as 2,4,6-triphenylbenzaldehyde (Suslick, K. S. and Fox, M. M. *J. Am. Chem. Soc.* 1983, 105, 3507–3510; Sugimoto, H. et al., *Macromolecules* 1990, 23, 2869–2875), 2,6-bis(trifluoromethyl)benzaldehyde (Lindsey, J. S. and Wagner, R. W. *J. Org. Chem.* 1989, 54, 828–836), 2,6-dibromobenzaldehyde (Collman, J. P. et al., *J. Am. Chem. Soc.* 1990, 112, 2986–2998), or 9-anthraldehyde (Cense, J.-M. and Le Quan, R.-M. *Tetrahedron Lett.* 1979, 3725–3728). Treatment of 13 with TBAF in $CHCl_3$ afforded the 2,6-diethynyl-substituted zinc porphyrin 13' in 82% yield.

The last step in the preparation of perylene-porphyrin 7 employs Sonogashira coupling of 13' and two equivalents of bromo-perylene building block PMI-9. The conditions for this coupling reaction are identical to those developed for the Sonogashira coupling of iodoporphyrins and ethynylporphyrins (Wagner, R. W. et al., *Chem. Mater.* 1999, 11, 2974–2983) with the following modifications: (1) The reaction temperature is 60° C. to facilitate coupling of the less reactive bromo substituent (Loewe, R. S. et al., *J. Mater. Chem.* 2002, 12, 1530–1552); (2) a 10:1 ratio of toluene/TEA is employed; and (3) the reaction is performed at 10 mM perylene. Purification using the three-column procedure (Wagner, R. W. et al., *Chem. Mater.* 1999, 11, 2974–2983) afforded 7 in 27% yield. Proton NMR analysis confirmed that the perylenes project over the face of the porphyrin macrocycle as evidenced by the upfield resonances of the two isopropyl groups and the hydrogens on the aryl group attached to the N-imide position of the perylene. This architecture is designed to suppress cofacial aggregation between porphyrins in solution.

The successful synthesis of the linked array provides a new avenue for preparing facially encumbered porphyrins. Facially encumbered porphyrins have been of central interest for numerous reasons, including (1) introducing catalytic functionalities over the apical site of the central metal; (2) providing receptor binding sites for holding guest molecules over the face of the porphyrin, (3) preventing the cofacial juxtaposition of two porphyrins (e.g., as would occur upon α-oxo dimer formation), and (4) suppressing cofacial aggregation of porphyrins and thereby increasing the solubility of the disk-like porphyrin macrocycle. A versatile approach toward facially encumbered porphyrins employs synthesis of o-aminophenyl substituted porphyrins (i.e., picket-fence porphyrins) followed by derivatization of the amino group with carboxylic acid derivatives. Few other o-functionalities are available that are compact, can be readily derivatized, and afford a stable product.

(3) Synthesis of Divergent Perylene-Porphyrin Arrays. The attachment at the 3,5-positions of the porphyrin meso-aryl ring causes each perylene-monoimide to project away from and out of the plane of the porphyrin.

$A_3B$-Porphyrin Bearing Two Perylenes. A 3,5-bis(perylene)aldehyde was prepared as a precursor for the synthesis of several 3,5-bis(perylene)-porphyrin arrays (approach A). Sonogashira coupling of ethynylperylene PMI-10' and commercially available 3,5-dibromobenzaldehyde (14) afforded perylene-aldehyde 15 in 35% yield (Scheme 9). The coupling reaction was performed in toluene/TEA (10:1) at 60° C. with the perylene at a concentration of 14 mM. Unfortunately, compound 15 exhibited poor solubility and attempts to prepare perylene-porphyrin arrays proved unsuccessful.

Scheme 9

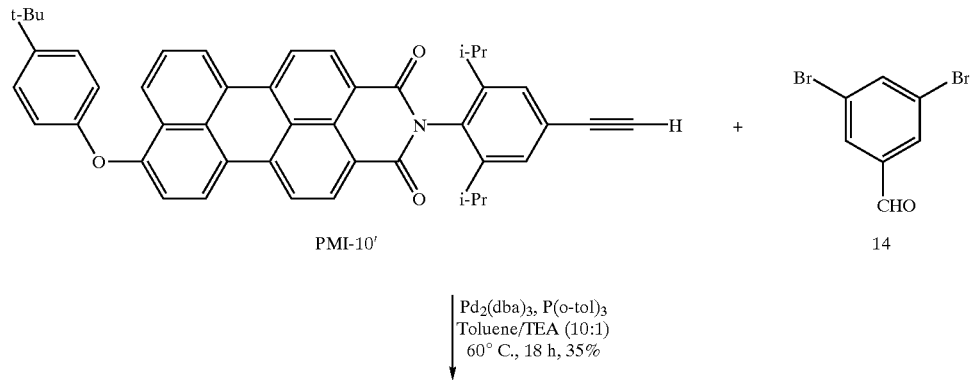

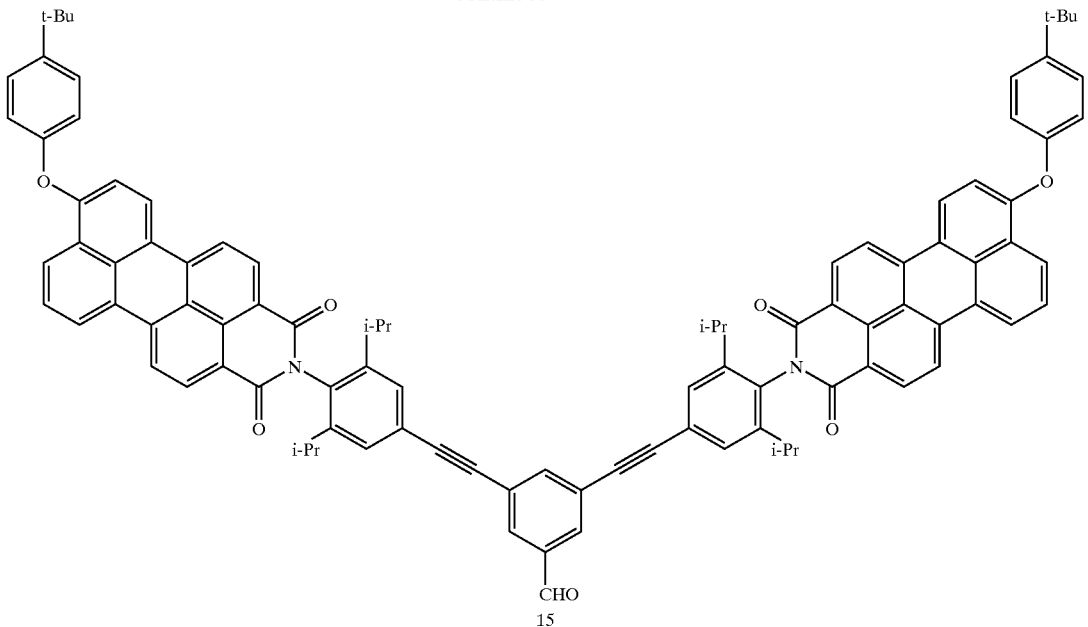

15

Because of the poor solubility of 15, we turned to approach B for preparing 3,5-bis(perylene)porphyrin arrays. The reaction of aldehyde 16, mesitaldehyde, and pyrrole was performed with $BF_3 \cdot O(Et)_2$-ethanol cocatalysis (Lindsey, J. S. and Wagner, R. W. *J. Org. Chem.* 1989, 54, 828–836) in $CHCl_3$ at room temperature following a procedure for a mixed-aldehyde condensation (Scheme 10). Oxidation with DDQ afforded a mixture of porphyrins. Treatment of the partially purified porphyrin mixture with $Zn(OAc)_2 \cdot 2H_2O$ followed by column chromatography afforded the zinc porphyrin building block 17 in 14% yield. The reaction of porphyrin 17 with two equivalents of bromoperylene PMI-9 under Sonogashira coupling conditions afforded the bis(perylene)porphyrin 8 in 13% yield.

A Soluble Bis(perylene)Aldehyde Intermediate. We attempted to prepare a trans-$A_2B_2$-porphyrin array bearing four perylene accessory pigments using approach B. Aldehyde 16 and 5-mesityldipyrromethane were condensed using TFA in $CH_2Cl_2$ at room temperature for 30 min, followed by oxidation with DDQ. However, the expected perylene-porphyrin array could not be purified due to limited solubility in toluene and THF.

Scheme 10

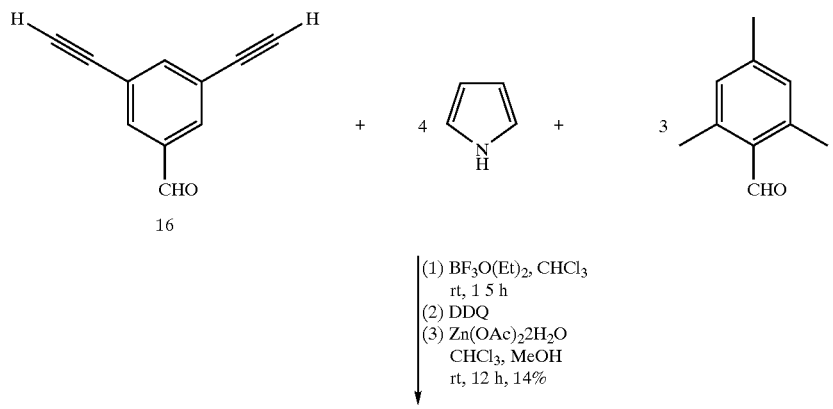

16

(1) $BF_3O(Et)_2$, $CHCl_3$
    rt, 1.5 h
(2) DDQ
(3) $Zn(OAc)_2 \cdot 2H_2O$
    $CHCl_3$, MeOH
    rt, 12 h, 14%

-continued
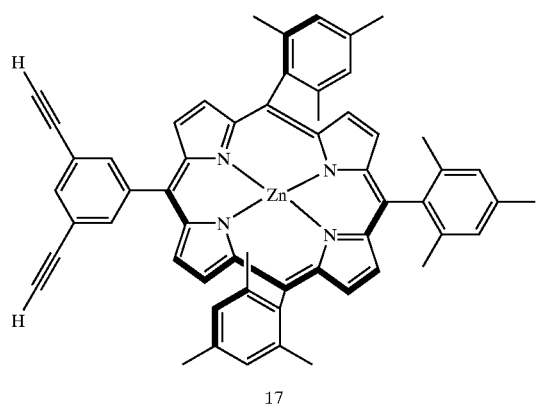
17
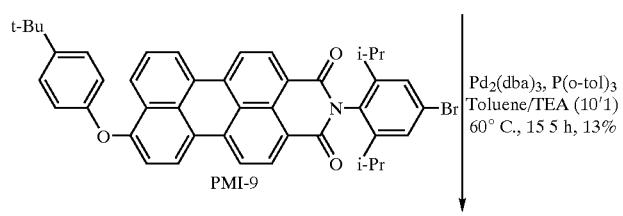
PMI-9
Pd$_2$(dba)$_3$, P(o-tol)$_3$
Toluene/TEA (10′1)
60° C., 15 5 h, 13%
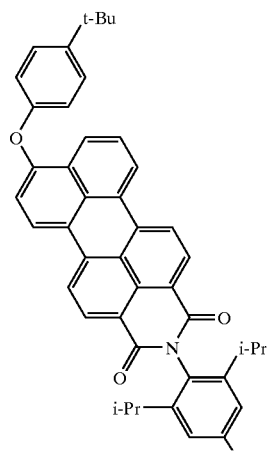
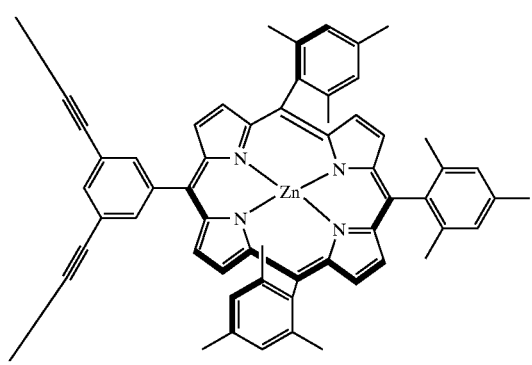

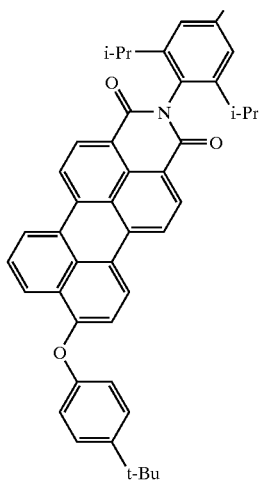

8

The higher solubility of perylenes bearing three aryloxy groups (1-, 6-, and 9-positions) versus only one aryloxy group (9-position) prompted us to employ the tris(aryloxy) perylenes PMI-12 and PMI-12' as precursors to perylene-porphyrin arrays. We explored two Sonogashira routes to a suitable perylene-aldehyde (18) for use in approach A (Scheme 11).

Scheme 11

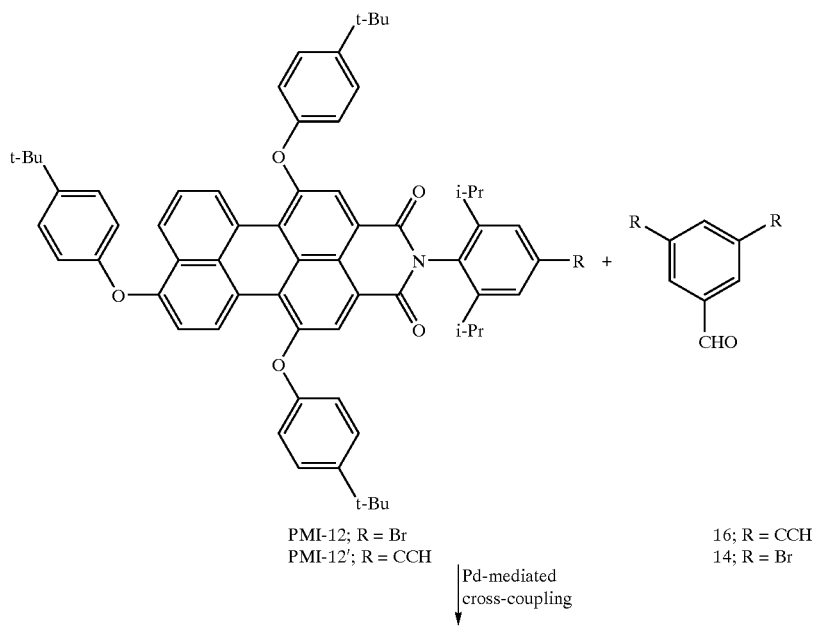

PMI-12; R = Br
PMI-12'; R = CCH

16; R = CCH
14; R = Br

Pd-mediated cross-coupling

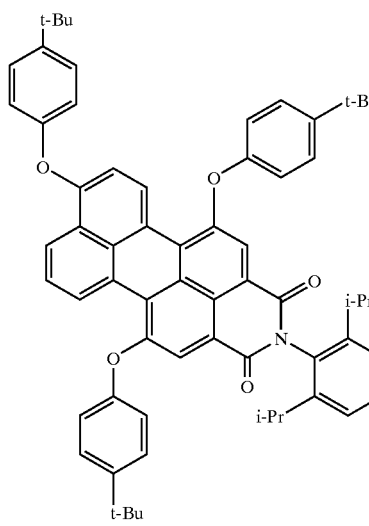
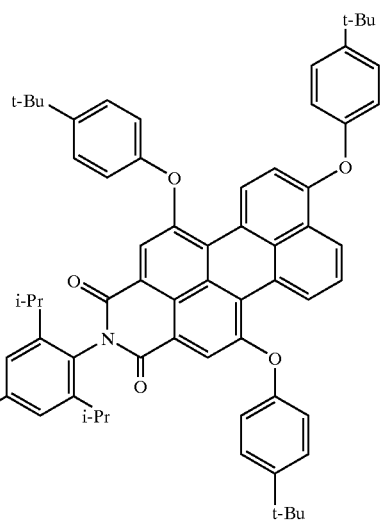
18
(1) Mesitaldehyde, pyrrole
    BF$_3$·O(Et)$_2$, CHCl$_3$
    rt, 1.5 h
(2) DDQ
(3) Zn(OAc)$_2$ 2H$_2$O
    CH$_2$Cl$_2$, MeOH
    rt, 12 h, 18%
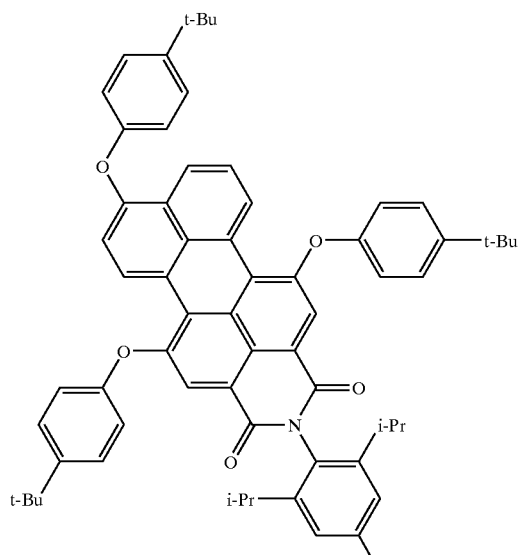

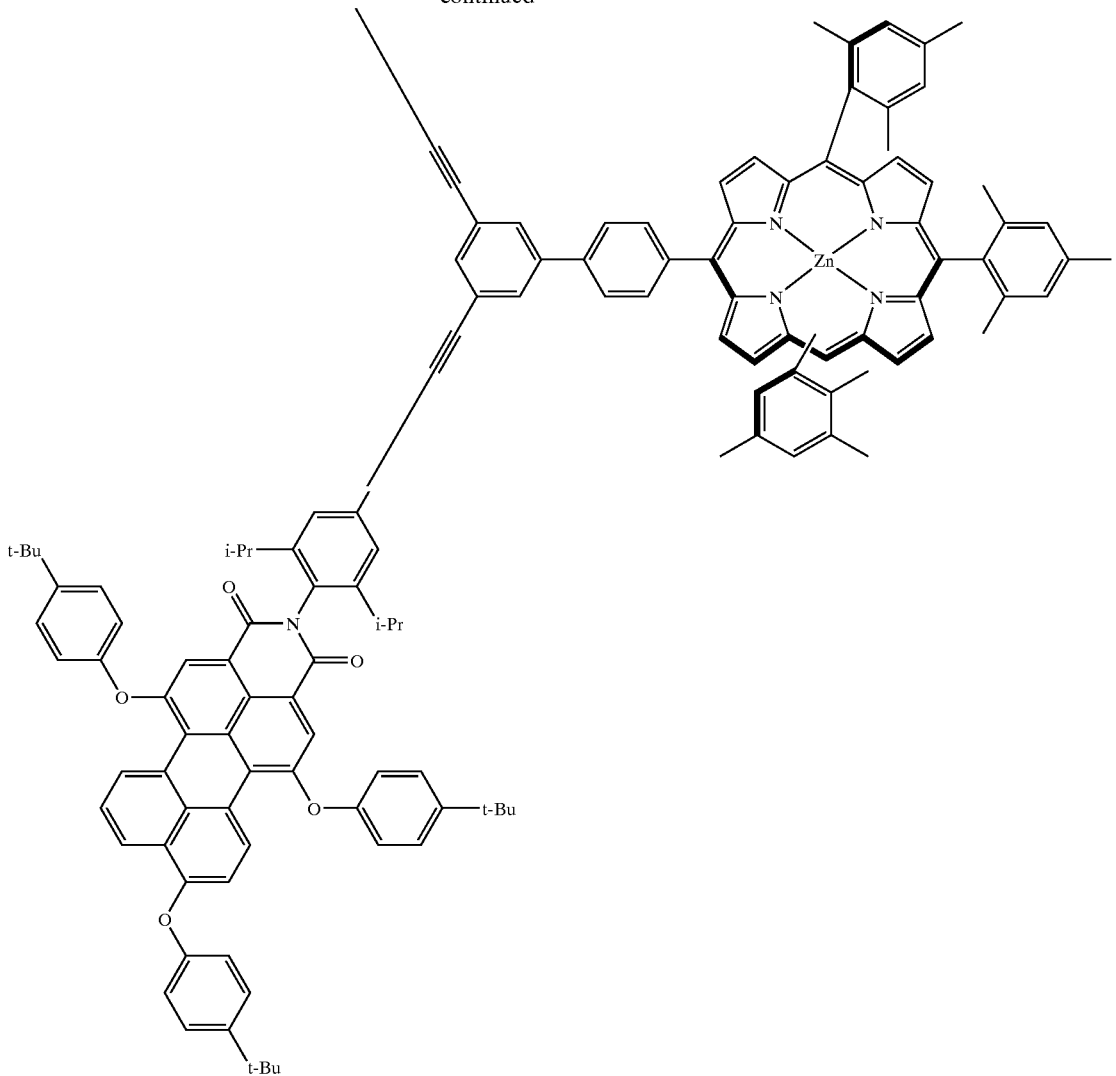

9

The first route employs bromoperylene PMI-12 and 3,5-diethynylbenzaldehyde (16) as the starting materials. The reaction under copper-free conditions, similar to those employed for the Sonogashira coupling of two porphyrins (Wagner, R. W. et al., *Chem. Mater.* 1999, 11, 2974–2983) afforded only a small amount (8.9%) of perylene-aldehyde 18 (entry 1, Table 1). The same reaction in the presence of CuI failed to produce perylene-aldehyde 18 (entry 2). We next examined the reaction with the reverse ethyne/bromo substitution pattern on the perylene and benzaldehyde. The reaction of ethynylperylene PMI-12' and 3,5-dibromobenzaldehyde (14) (2:1 ratio) with CuI cocatalysis afforded 18 in 31% yield (entry 3). A further increase in the amount of perylene PMI-12' (2.4:1 ratio) gave 18 in 66% yield (entry 4). Repetition of this reaction furnished 18 in 83% yield. While of limited scope, the survey of the Sonogashira reaction of perylene PMI-12 or PMI-12' with aldehyde 14 or 16 revealed important reactivity differences between a bromoperylene and an ethynylperylene. Unlike perylene-aldehyde 15, compound 18 proved to be very soluble, thereby enabling subsequent porphyrin-forming reactions.

$A_3B$-Porphyrin Bearing Two Perylenes. An $A_3B$-porphyrin was prepared using a mixed-aldehyde condensation of perylene-aldehyde 18, mesitaldehyde, and pyrrole with $BF_3.O(Et)_2$-ethanol cocatalysis (Lindsey, J. S. and Wagner, R. W. *J. Org. Chem.* 1989, 54, 828–836) in $CHCl_3$ (Scheme 11). Oxidation with DDQ followed by zinc metalation afforded perylene-porphyrin 9 in 18% yield following preparative SEC and one silica gel column. This array contains two perylenes attached at the 3,5-positions of the porphyrin meso-aryl ring.

Trans-$A_2B_2$-Porphyrin Bearing Four Perylenes. The condensation of perylene-aldehyde 18 with 5-mesityldipyrromethane (19) was carried out under conditions [(1) TFA, $CH_2Cl_2$, room temperature, 30 min; (2) DDQ] that proceed without detectable formation of byproducts derived from acidolysis of a dipyrromethane followed by undesired recombination (i.e., scrambling) (Littler, B. J. et al., *J. Org. Chem.* 1999, 64, 2864–2872). Oxidation with DDQ afforded the free base porphyrin. Metalation using $Zn(OAc)_2.2H_2O$ followed by purification afforded perylene-porphyrin 10 in 28% yield (Scheme 12). This array contains four perylenes attached at the 3,5-positions of the trans-porphyrin meso-aryl rings.

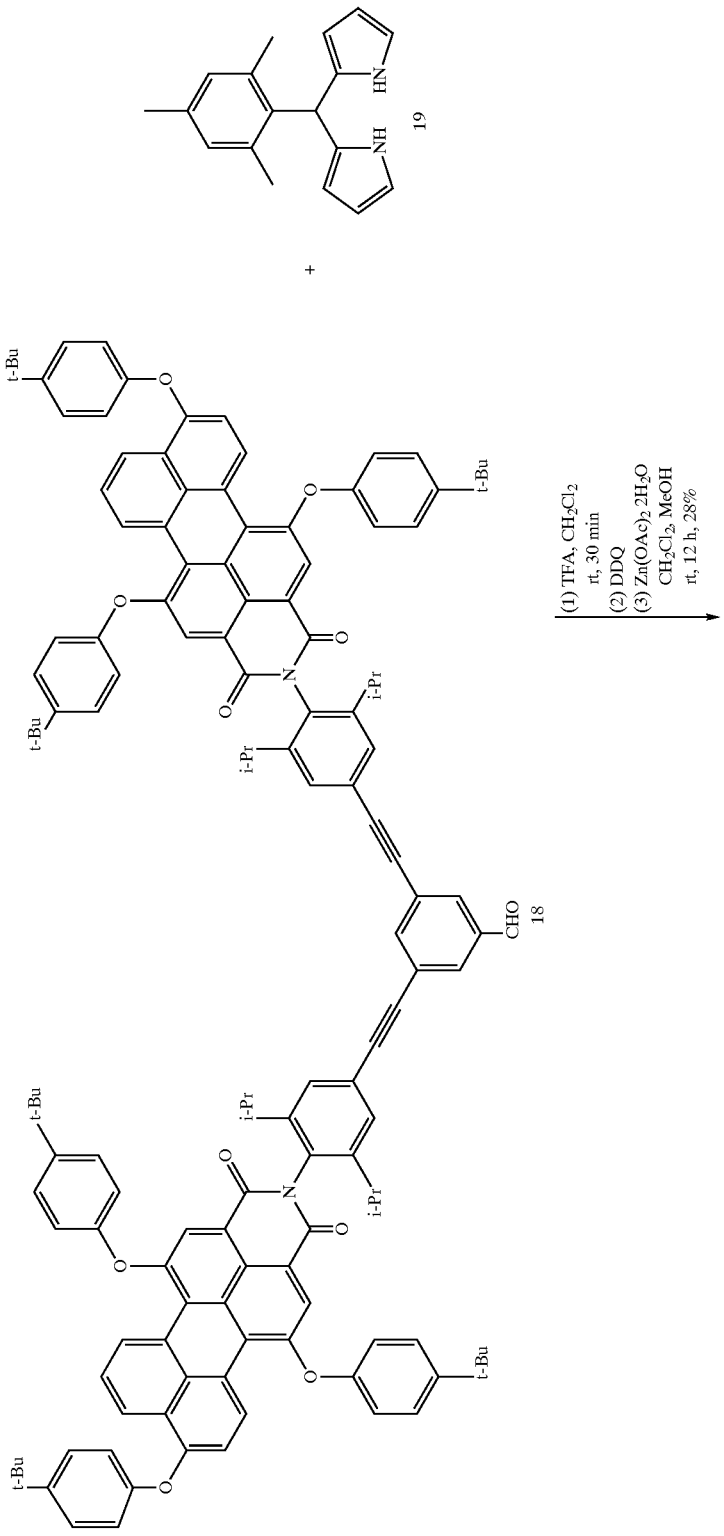

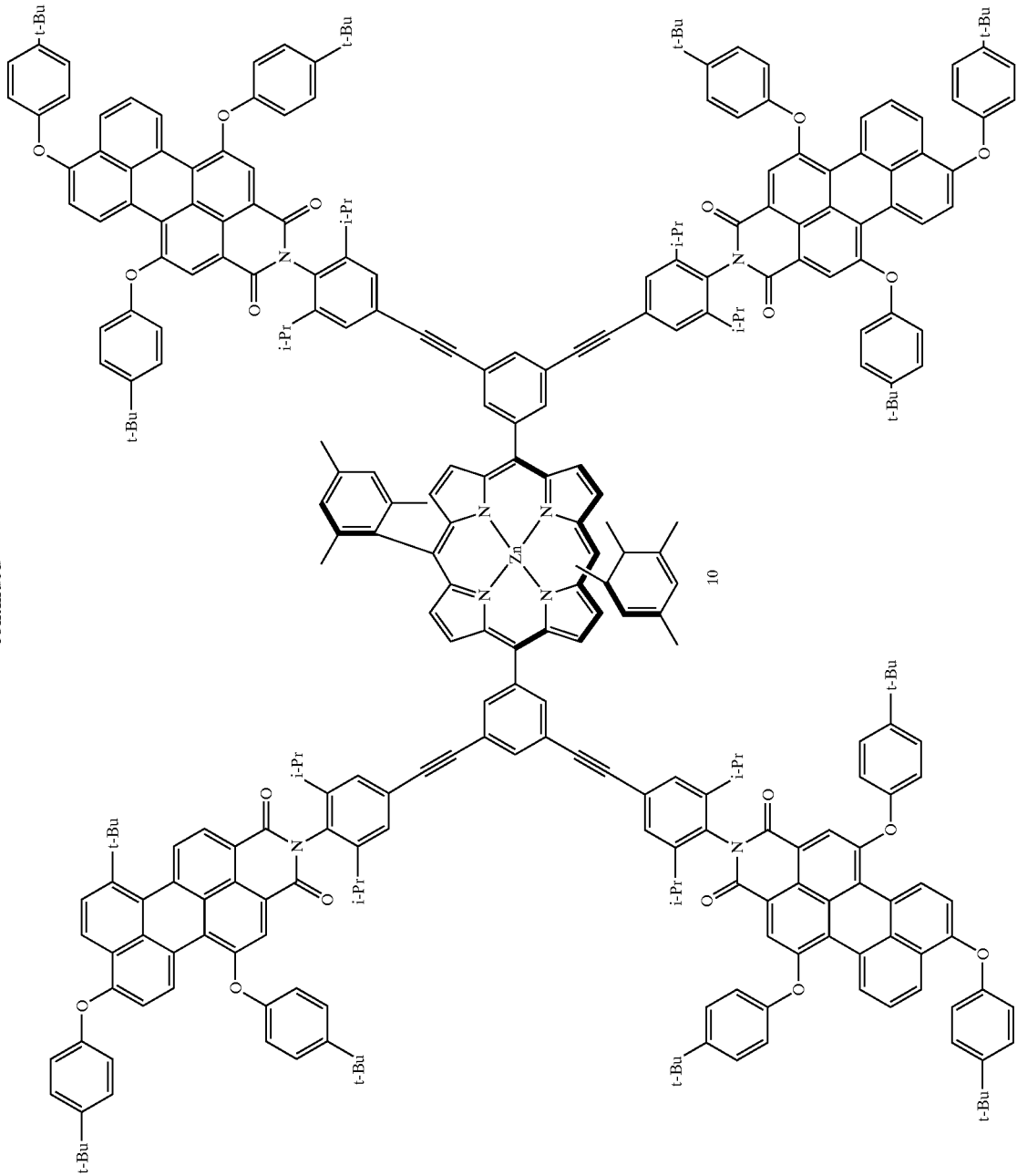

A$_4$-Porphyrin Bearing Eight Perylenes. The condensation of perylene-aldehyde 18 and pyrrole was performed in the presence of BF$_3$.O(Et)$_2$ and NaCl in CH$_2$Cl$_2$ at room temperature for 1 h. The addition of NaCl to the porphyrin-forming reaction has been shown to increase the yield of porphyrin by up to 2-fold in some cases (Li, F. et al., Tetrahedron 1997, 53, 12339–12360; Geier, G. R., III et al., J. Porphyrins Phthalocyanines 2001, 5, 681–690). Oxidation with DDQ followed by zinc insertion afforded perylene-porphyrin 11 in 31% yield. This perylene-porphyrin light-harvesting array contains eight perylene accessory pigments, with exhaustive substitution at the 3,5-positions of each of the four meso-phenyl rings of the porphyrin. The presence of eight perylenes and 24 aryloxy substituents results in a sizable mass (8264 Da) for the array to which the porphyrin makes a minor contribution.

(4) Chemical Characterization. Each perylene-porphyrin array was characterized by analytical size exclusion chromatography (SEC), thin layer chromatography, LD-MS, $^1$H NMR spectroscopy, absorption spectroscopy, and fluorescence emission spectroscopy.

SEC Behavior. Each purified array exhibited a single sharp peak in the analytical SEC chromatogram. In addition to providing evidence for purity, in a few instances evidence also was obtained concerning the relative hydrodynamic volumes of isomeric arrays. For example, perylene-porphyrin arrays 7 and 8 have identical molecular weight yet showed a difference in retention times of 0.23 min. In the 2,6-disubstituted system 7, the perylenes project towards the porphyrin macrocycle, affording a more compact architecture as compared to the 3,5-disubstituted system 8, in which the perylenes project away from the porphyrin macrocycle.

Solubility. High solubility in a variety of solvents is critical for purification, characterization, and photochemical studies. We have found each of the perylene-porphyrin arrays to be sufficiently soluble for routine chemical processing. The highest solubility was noted for arrays 9–11, wherein each perylene bears three 4-tert-butylphenoxy substituents. These arrays are soluble in hexanes/CH$_2$Cl$_2$ (1:1) for preparative chromatography, are soluble in minimal amounts of CDCl$_3$ for NMR spectroscopy, afford 10 mM solutions in toluene, CHCl$_3$, CH$_2$Cl$_2$, or THF, and can be examined spectroscopically in benzonitrile. The high solubility of these perylene-porphyrin model compounds augurs well for the use of these motifs in larger light-harvesting arrays.

(5) Photochemical Characterization of Benchmark Perylene Dyes. The 4-tert-butylphenoxy substituents were introduced as a means of imparting greater solubility to the perylene-porphyrin arrays. The presence of the aryloxy substituents also causes significant changes in the absorption spectrum of the perylene dye. A summary of the absorption, fluorescence, and photophysical properties of these three benchmark perylene-monoimide dyes (PMI-2, PMI-13, and PMI-12' bearing zero, one or three 4-tert-butylphenoxy substituents) is shown in Table 2. The perylene-monoimides display a broad absorption manifold (fwhm ~85 nm) with a modest molar extinction coefficient ($\epsilon_{\lambda max}$ ~35,000 M$^{-1}$ cm$^{-1}$). The unsubstituted perylene-monoimide exhibits absorption bands at 479 and 507 nm due to the (1, 0) and (0, 0) transitions, respectively. The presence of one or three 4-tert-butylphenoxy substituent results in a bathochromic shift of approximately 30 nm and some broadening of the absorption manifold. The fluorescence emission spectra of the three perylene benchmarks shift commensurably, from peak maxima at 530 and 570 nm for PMI-2 to 567 and 611 nm for PMI-13 and 577 and 615 nm for PMI-12'. Thus, the dominant contribution to the spectral shift stems from substitution at the 9-position of the perylene; further substitution of two aryloxy groups at the flanking positions (1-, 6-) of the perylene has less effect on the spectral properties. A further demonstration of the spectral shift caused by substitution at the 9-position is observed in a perylene-monoimide dye bearing two 4-tert-butylphenoxy substituents (at the 1- and 6-positions) and an N-pyrrolidinyl substituent at the 9-position, which has $\lambda_{max}$ =601 nm (Gosztola, D. et al., J. Am. Chem. Soc. 1998, 120, 5118–5119). Perylene-monoimide dyes each bearing four aryloxy substituents (at the 1, 6-, 7-, and 12-positions) have also been prepared but spectral data have not been reported (Holtrup, F. O. et al., Chem. Eur. J. 1997, 3, 219–225).

The presence of solubilizing aryloxy groups does not significantly affect the fluorescence quantum yield of the perylene [$\Phi_f$=0.91, 0.82, and 0.86 for PMI-2, PMI-13, and PMI-12', respectively (Table 2)]. These data demonstrate that the perylene monoimide building blocks employed in this study (bearing one or three aryloxy groups) are suitable accessory pigments for porphyrins.

Absorption Spectroscopy of Perylene-Porphyrin Arrays. FIG. 1 shows the absorption spectra of perylene-porphyrin arrays 9–11, along with the spectra of reference compounds porphyrin 17 and perylene PMI-12'. There are several noteworthy points: (1) A small but systematic bathochromic shift is observed in the Soret band as the number of perylenes is increased, with an overall shift of 8 nm upon going from an unsubstituted porphyrin to a porphyrin bearing eight perylenes. A similar effect was noted in the architecturally similar array bearing eight boron-dipyrrin dyes (Li, F. et al., J. Am. Chem. Soc. 1998, 120, 10001–10017). (2) The absorption due to the perylene in the arrays increases linearly upon going from two to four to eight perylenes (based on the normalized Soret band). (3) The absorption spectrum in the visible region of each perylene-porphyrin array is well approximated by the sum of the spectra of the component parts. This observation is indicative of the relatively weak electronic coupling between the perylenes and porphyrin. The absorption properties of the arrays are summarized in Table 3.

Figure 2:
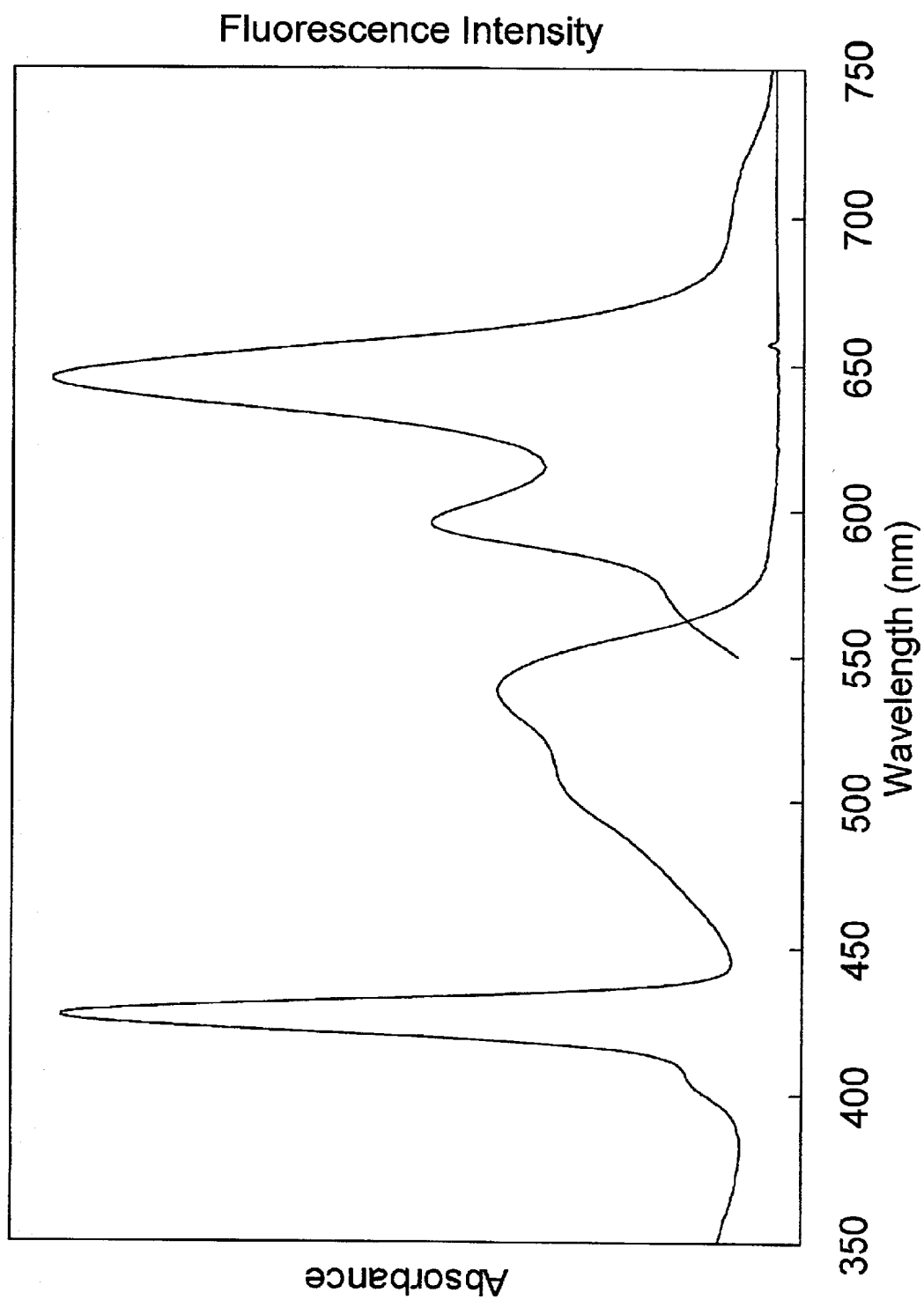
FIG. 2. Absorption spectrum of 10 in toluene at room temperature. The fluorescence spectrum was obtained in toluene at room temperature upon illumination at 540 nm. The fluorescence spectrum shows the efficient energy transfer from perylene to porphyrin.

Fluorescence Spectroscopy of Perylene-Porphyrin Arrays. Each perylene-porphyrin array (7–11) was analyzed by fluorescence emission spectroscopy in toluene at room temperature. Excitation at 490 nm, where the perylene dye absorbs preferentially, resulted in emission characteristic of both the perylene and the zinc porphyrin (600, 650 nm). The yield of emission from the perylene was diminished at least 20-fold from that of the benchmark perylene monomer. These results are consistent with efficient energy transfer ($\Phi_{trans}$>95%). In each case, the observation of a significant level of emission from the perylene and from the porphyrin reflects the fact that the quantum yield of fluorescence ($\Phi_f$) is 0.82 and 0.86 for the benchmark mono-aryloxy-perylene derivative PMI-13 and the tris(aryloxy)perylene derivative PMI-12', respectively, whereas the yield of the zinc porphyrin is only ~0.03–0.05. An example is shown for 10 in FIG. 2. The emission band at 570–580 nm is the residual perylene emission, which occurs as a shoulder on the comparatively intense band of the porphyrin.

The fluorescence yield of the zinc porphyrin in each array also was examined ($\lambda_{exc}$=423 nm) in order to identify any quenching interactions due to the presence of the appended perylene dyes. Quantum yield measurements were performed in both toluene and benzonitrile to garner information as to the photophysical behavior of these systems in nonpolar and polar media, respectively. In toluene, each perylene-porphyrin array showed a fluorescence yield ($\Phi_f$) value comparable to or greater than that of zinc tetraphenylporphyrin (ZnTPP) (Seybold, P. G. and Gouterman, M. *J. Mol. Spectrosc.* 1969, 31, 1–13). In benzonitrile, each array (except 7) also exhibited a fluorescence quantum yield greater than that of ZnTPP. (The fluorescence yields slightly greater than that of ZnTPP are consistently observed for tetraarylporphyrins bearing ethyne substituents. Note that in each array and benchmark porphyrin, the Soret absorption band red-shifts by approximately 8 nm in going from toluene to benzonitrile. The results are summarized in Table 3. Array 7 is unique among the arrays examined in having the perylenes attached at the 2,6-positions (and thus at a closer distance to the porphyrin) rather than the 3,5-positions of the meso-aryl ring of the porphyrin. The distance between the perylene and the porphyrin (center-to-center, from the Zn atom of the porphyrin to the middle of the central benzenoid ring of the perylene) decreases from 17.5 to 11.1 Å in going from the 3- to the 2-position of the meso-aryl ring. The diminished yield of fluorescence from the zinc porphyrin in 7 likely stems from competing electron-transfer processes. Regardless, all array architectures examined are suitable for use as light-harvesting systems in toluene while the arrays with perylenes at the 3,5-positions are suitable in benzonitrile.

Förster Energy-Transfer Calculations. Förster calculations were performed in order to assess the contribution of through-space energy transfer to the observed energy-transfer process. The calculations were performed using PhotochemCAD (Du, H. et al., *Photochem. Photobiol.* 1998, 68, 141–142) for samples in toluene at room temperature. The spectral overlap terms (J values) for ZnTPP and the perylenes PMI-2, PMI-13, and PMI-12' are $J=7.0\times10^{-14}$, $5.1\times10^{-14}$, and $4.5\times10^{-14}$ cm$^6$/mmol, respectively. The slight decline in J value across this series reflects the bathochromic shift of the emission spectrum of the perylene dye upon substitution with aryloxy substituents, and resulting diminished overlap with the Q(1, 0) transition of the zinc porphyrin at 550 nm. The calculations are performed assuming the value for the orientation term $K^2 \geq 1.0$. The assessment of the orientation term is based on the assumptions that (1) the transition dipole moment lies along the long axis of the perylene whereas the zinc porphyrin is a planar oscillator, (2) the linker provides a fixed distance of separation. In practice, the center-to-center distance can be altered by bending (Bothner-By, A. A. et al., *J. Phys. Chem.* 1996, 100, 17551–17557) of the arylethynylphenyl linker and torsion about the bond between the porphyrin meso-carbon and the linker phenyl unit. Such factors limit the accuracy of the calculations. For each perylene-porphyrin combination (monoaryloxy-perylene at the porphyrin 2-aryl position, 7; monoaryloxy-perylene at the porphyrin 3-aryl position, 8; tris(aryloxy)perylene at the porphyrin 3-aryl position, 9–11), the yield of through-space energy transfer is calculated to be >99.5%. Table 4 displays energy-transfer rates and efficiencies for several arrays.

(6) Effective Accessory Pigments. The perylene dyes examined herein appear to be ideal for use as accessory pigments with porphyrins. The perylene dyes provide the following attributes: (1) absorption in the trough between the porphyrin B and Q bands; (2) efficient energy transfer to the porphyrin; (3) absence of competing electron-transfer quenching processes with the photoexcited porphyrin in polar or non-polar solvents; (4) long excited-state lifetime, high fluorescence yield, and very low yield of intersystem crossing; (5) compatibility with a building block synthesis; (6) amenability to use in architectures with multiple accessory pigments; and (7) high solubility and non-polar nature affording facile purification. Very few classes of dyes meet this set of criteria (Wagner, R. W. and Lindsey, J. S. *Pure Appl. Chem.* 1996, 68, 1373–1380; Wagner, R. W.; Lindsey, J. S. *Pure Appl. Chem.* 1998, 70 (8), p. i). For example, xanthenes or cyanine dyes provide superior laser dyes and/or biolabels but are difficult to purify given their intrinsic charge. Carotenoids absorb strongly but have an exquisitely short excited-state lifetime requiring very close proximity to the porphyrin for efficient energy transfer. Boron-dipyrrin dyes have two excited-state conformers with short lifetimes, cause quenching of the photoexcited porphyrin in polar solvents, and in addition, present purification challenges upon incorporation in multi-pigment arrays due to their intrinsic polarity. The perylene-monoimides provide about 2.5-times the integrated absorption ($\epsilon_{\lambda max} \times$fwhm) of that of boron-dipyrrin dyes, which we have used previously for light-harvesting applications. All factors considered, the perylene and linker motifs examined herein are superior to other classes of dyes for use with porphyrins in light-harvesting architectures. In particular, the arrays with tris(aryloxy)perylene-monoimide dyes positioned at the 3,5-positions of one, two, or four aryl rings of the porphyrin have high solubility and unperturbed porphyrin fluorescence in non-polar (toluene) and polar (benzonitrile) solvents. By comparison, the arrays with perylene-monoimide dyes positioned at the 2,6-positions provide a more compact geometry but are synthesized in lower yields and also are less suited for light-harvesting applications in polar media.

Part C. In Part B, we found that perylene-monoimides linked to a porphyrin via an arylethynylphenyl linker were viable accessory pigments with porphyrins. The linker bridges the p-position of the N-aryl ring of the perylene and the meso-position of the porphyrin. For solubility purposes, the perylenes are attached at the 2,6- or 3,5-positions of the porphyrin meso-aryl group, thereby suppressing cofacial aggregation among neighboring porphyrins in solution. In addition, each perylene contains two isopropyl groups on the N-aryl unit and one or three 4-tert-butyloxyphenyl substituents on the perylene perimeter to suppress aggregation of the perylenes. Significantly higher solubility is achieved with the tris(aryloxy)perylene dyes.

In this section we present the synthesis and properties of multiperylene-porphyrin building blocks. The building blocks are designed based on our studies of multiperylene-porphyrin arrays. Each building block contains two synthetic handles in a trans-configuration at the porphyrin meso-positions; the non-linking meso-positions of the porphyrin bear one, two, or four perylene-monoimide dyes. A convergent or divergent architecture results upon incorporation of the perylenes at the 2- or 3,5-positions of the meso-aryl group(s), respectively.

A. trans-AB$_2$C-Porphyrin Bearing One Perylene (Convergent Architecture). The first class of building blocks employs a perylene linked to a porphyrin at the 2-position of one of the meso-aryl rings of the porphyrin. Condensation of o-ethynylbenzaldehyde with excess pyrrole (Littler, B. J. et al., *J. Org. Chem.* 1999, 64, 1391–1396) afforded 5-(2-ethynylphenyl)dipyrromethane (20) in 40% yield after chromatographic workup (Scheme 13). The reaction was catalyzed using 0.1 eq of TFA at room temperature for 10 min. Purification by Kugelrohr distillation was not attempted given the reactive nature of the ethyne group.

Scheme 13

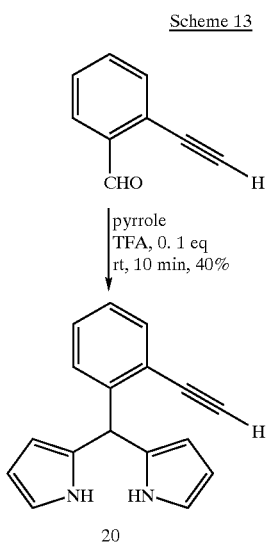

The synthesis of ethynylporphyrin building block 22' was attempted under new conditions (Geier, G. R. III et al., *J. Porphyrins Phthalocyanines* 2001, 5, 810–823) for the dipyrromethane+dipyrromethane-dicarbinol condensation, which employ one of four trivalent Lewis acids [$InCl_3$, $Sc(OTf)_3$, $Yb(OTf)_3$, or $Dy(OTf)_3$] in $CH_2Cl_2$ at room temperature. Compared to TFA catalysis (30 mM in $CH_3CN$ at room temperature) (Rao, P. D. et al., *J. Org. Chem.* 2000, 65, 7323–7344), the new conditions provide increased yields of porphyrin accompanied by a simplified purification procedure. We initially chose $Yb(OTf)_3$ to promote condensation.

Standard reduction of diacyl dipyrromethane 21 with $NaBH_4$ (20 eq) yielded the dipyrromethane-dicarbinol as a foam-like solid. The dicarbinol (2.5 mM) was immediately dissolved in reagent-grade $CH_2Cl_2$ along with dipyrromethane 20 (2.5 mM). A sample of $Yb(OTf)_3$ (3.2 mM) (Geier, G. R. III et al., *J. Porphyrins Phthalocyanines* 2001, 5, 810–823) was then added. Aliquots were removed at 5 and 10 min intervals, treated with DDQ to cause oxidative conversion of the porphyrinogen to the porphyrin, and then analyzed by absorption spectroscopy. A broad and intense peak centered at 489 nm (fwhm ~50 mn) was observed but no Soret peak could be detected. After 15 min, DDQ was added but only traces of porphyrin were detected by TLC.

Attempts to use the standard condensation conditions (30 mM TFA in acetonitrile (Rao, P. D. et al., *J. Org. Chem.* 2000, 65, 7323–7344)) were not successful because the dicarbinol was only sparingly soluble in acetonitrile at 2.5 mM. However, the addition of $CH_2Cl_2$ in small portions to the suspension of dicarbinol in acetonitrile resulted in a homogeneous solution with a 9:1 mixture of acetonitrile/$CH_2Cl_2$. The addition of TFA (26 mM, due to the dilution factor of the additional $CH_2Cl_2$) caused an immediate color change. Aliquots were removed after 1 and 2 min, oxidized with DDQ, and analyzed by absorption spectroscopy. The yield of porphyrin at both timepoints was only 8%. After 3 min, DDQ was added to the reaction. LD-MS analysis did not show the formation of any products due to acidolysis and undesired recombination (i.e., scrambling). The absence of scrambling is important given that the dipyrromethane+dipyrromethane-dicarbinol condensation using TFA in neat $CH_2Cl_2$ affords significant scrambling after 1 min (Rao, P. D. et al., *J. Org. Chem.* 2000, 65, 7323–7344). The solubility of the porphyrin in acetonitrile was poor. After workup, a 23% yield of porphyrin was obtained; nearly three times that calculated by absorption spectroscopy. This discrepancy is likely due to the poor solubility of the porphyrinogen intermediate in the polar reaction medium. The free base porphyrin was then treated with $Zn(OAc)_2 \cdot 2H_2O$ in $CHCl_3$/MeOH to afford the zinc chelate 23' in 98% yield (Scheme 14).

Scheme 14

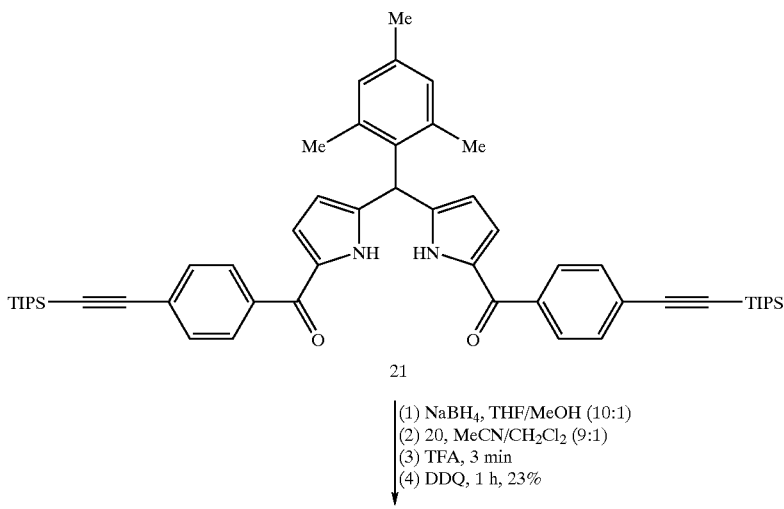

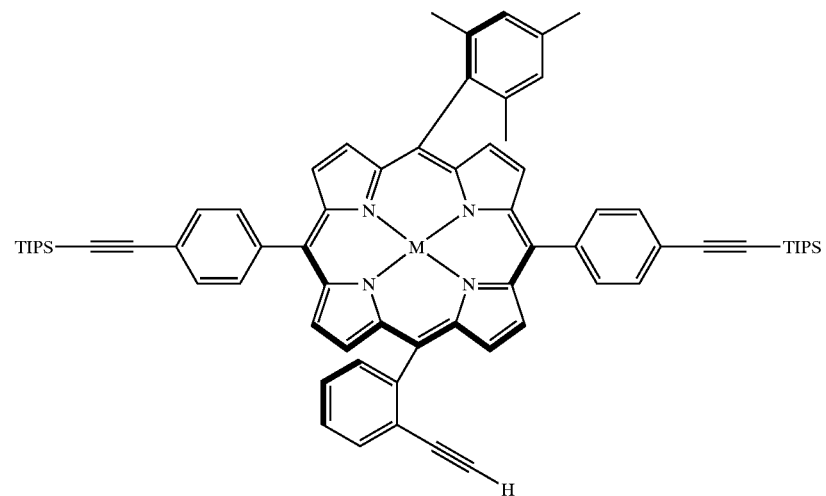
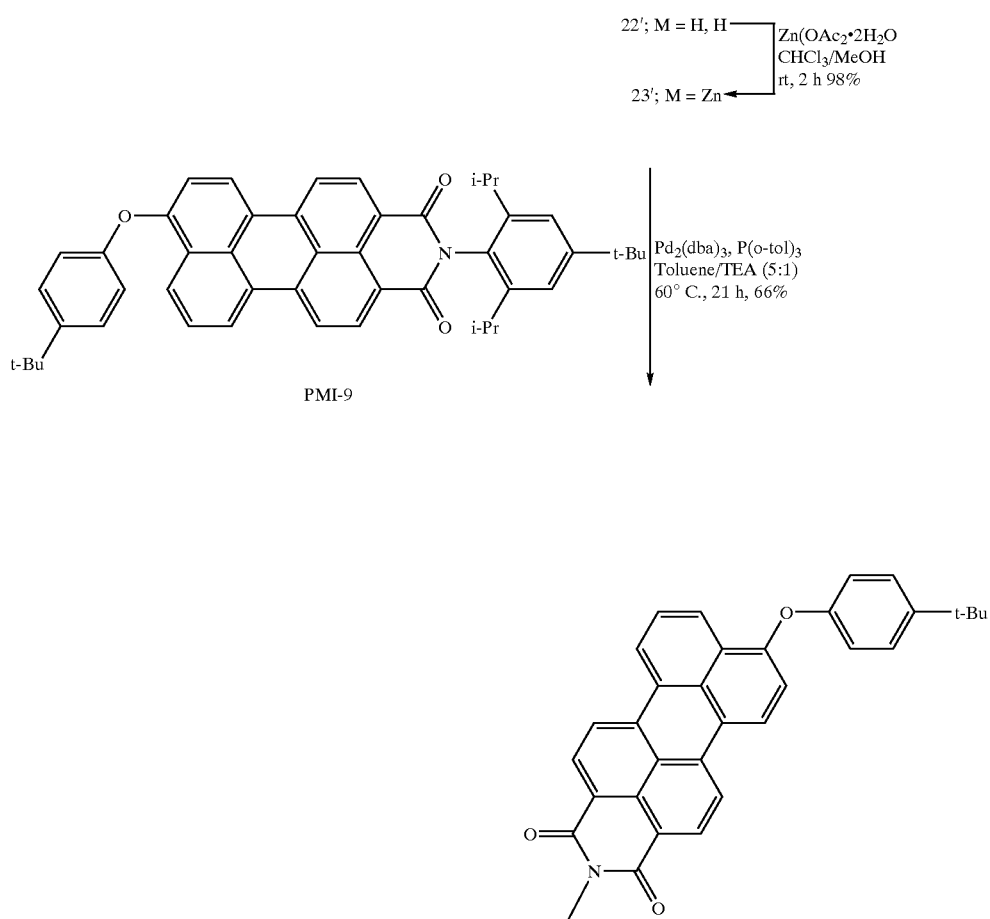

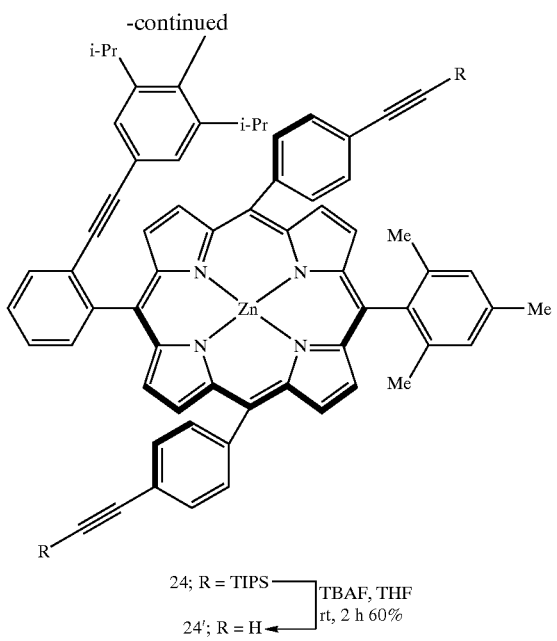

24; R = TIPS
24'; R = H
TBAF, THF
rt, 2 h 60%

Porphyrin 23' and bromoperylene PMI-9 were coupled in a Sonogashira reaction. The reaction was performed at 2.5 mM using Pd$_2$(dba)$_3$/P(o-tol)$_3$ (Wagner, R. W. et al., *Chem. Mater.* 1999, 11, 2974–2983) at 60° C. in toluene/TEA (5:1) for 21 h, conditions similar to those used with bromo- and ethynyl-substituted porphyrins (Loewe, R. S. et al., *J. Mater. Chem.* 2002, 12, 1530–1552). Perylene-porphyrin 24 was obtained in 66% yield. This porphyrin was treated with TBAF in THF at room temperature for 2 h to furnish the perylene-porphyrin building block 24' in 60% yield. This compound proved to be quite soluble in organic solvents. $^1$H NMR spectroscopy revealed upfield resonances of the isopropyl and N-aryl hydrogens of the perylene, as expected given that the perylene projects over the face of the porphyrin macrocycle.

Scheme 15

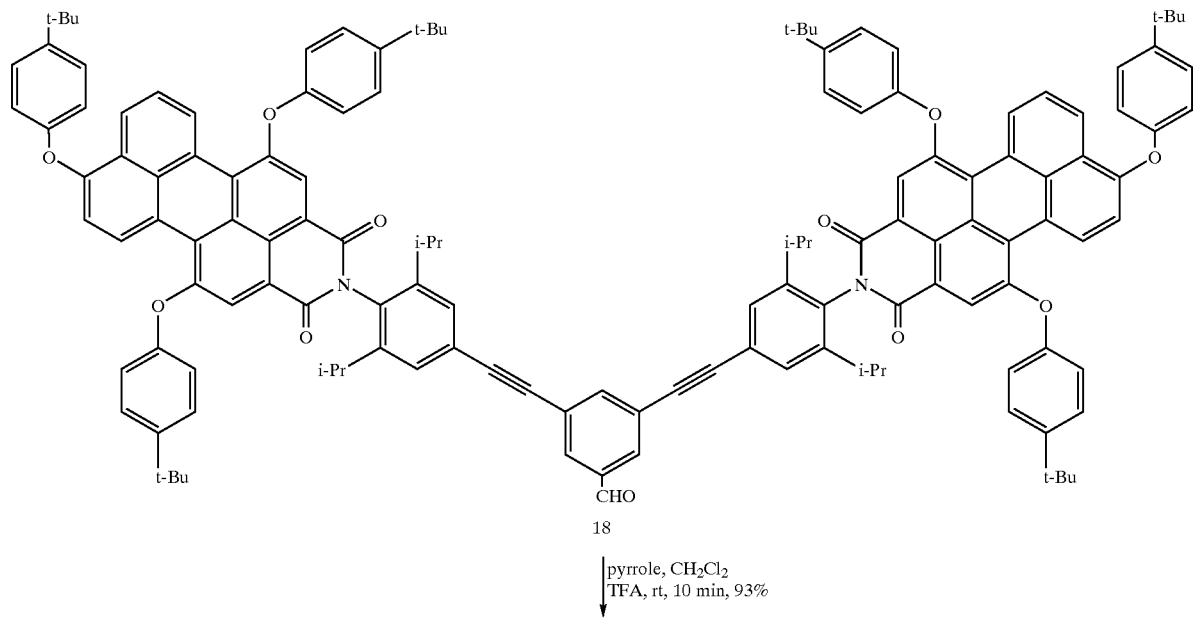

18 pyrrole, CH$_2$Cl$_2$
TFA, rt, 10 min, 93%

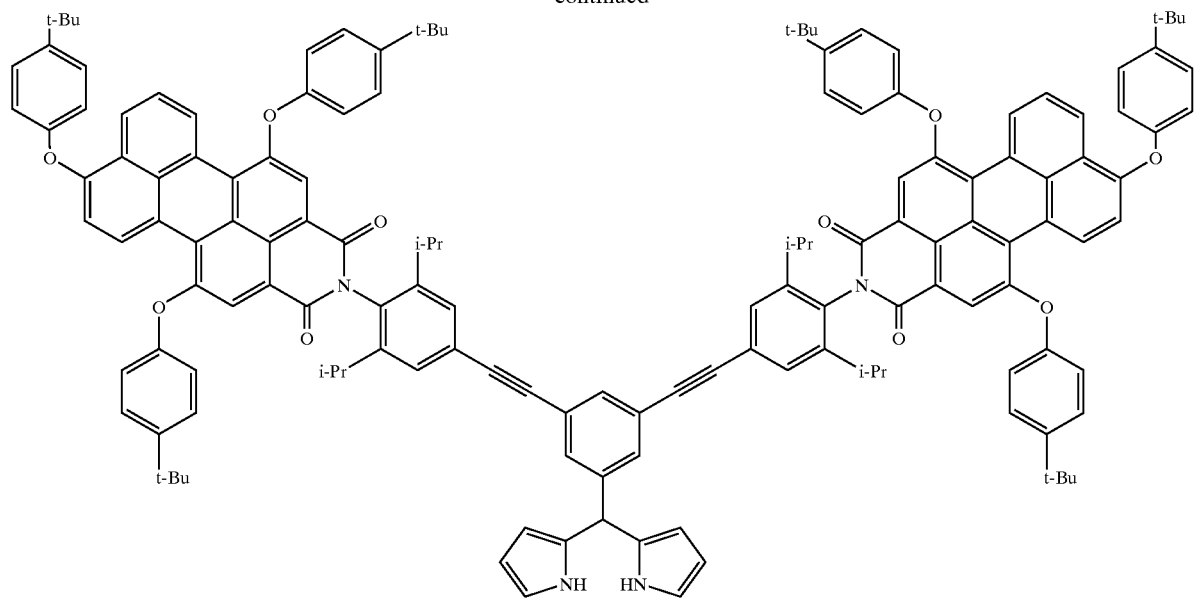

25

Porphyrins Bearing Two Perylenes (Divergent Architecture). The synthesis of a trans-AB$_2$C-porphyrin required the preparation of a bis(perylene)dipyrromethane for condensation with a dipyrromethane-dicarbinol. The perylene-dipyrromethane was prepared by reaction of perylene-aldehyde 18 with an excess of pyrrole (~400 equivalents; 623 mg of 18 in 9.0 mL of pyrrole). A small amount (3.0 mL) of methylene chloride was added to achieve full dissolution of the perylene-aldehyde. Addition of TFA and reaction for 10 min at room temperature afforded perylene-dipyrromethane 25 in 93% yield after chromatographic workup (Scheme 15). Preparation of the trans-AB$_2$C-porphyrin is shown in Scheme 16.

Scheme 16

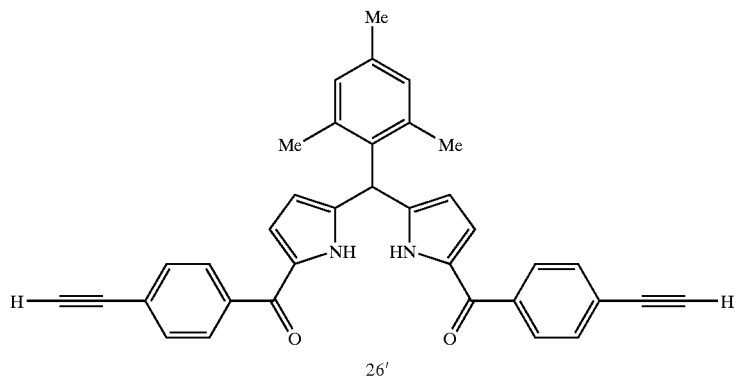

26'

(1) NaBH$_4$, THF/MeOH (10:1)
(2) 25, Yb(OTf)$_3$, CH$_2$Cl$_2$
    rt, 15 min
(3) DDQ
(4) Zn(OAc)$_2$·2H$_2$O
    CHCl$_3$, MeOH
    rt, 2 h, 36%

-continued
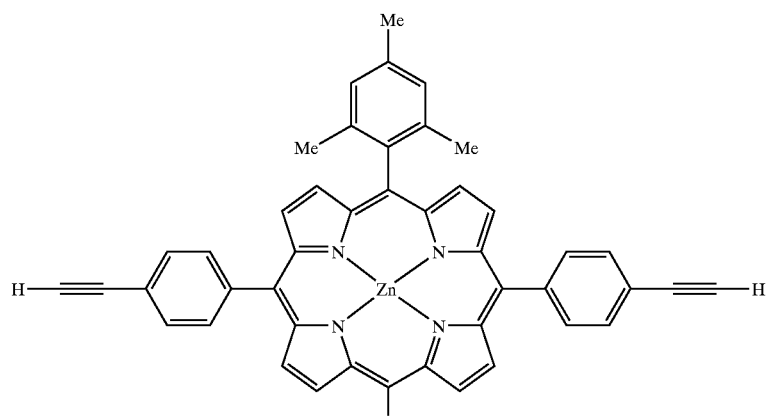
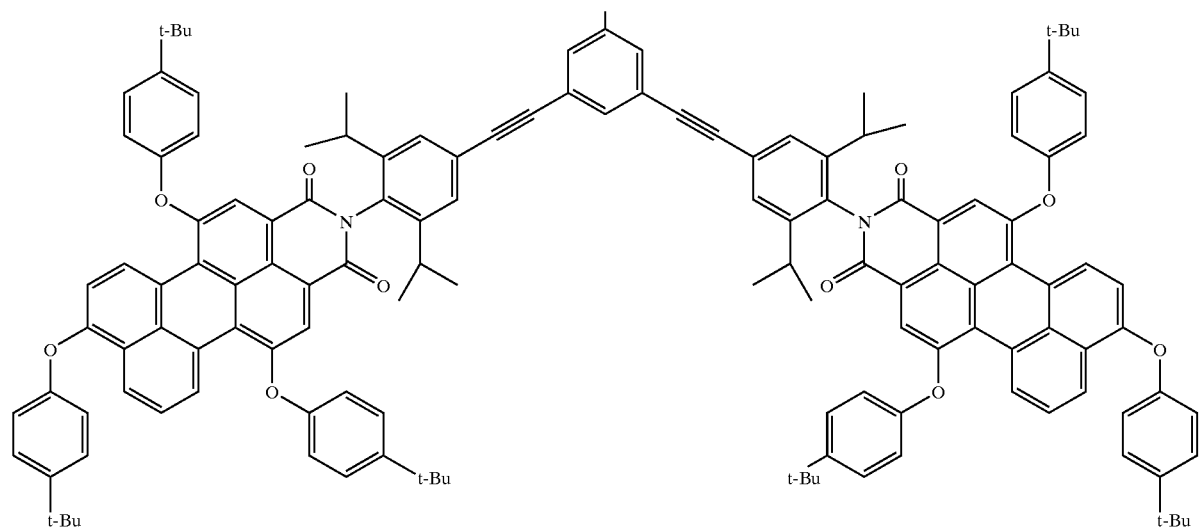
27'
Scheme 17
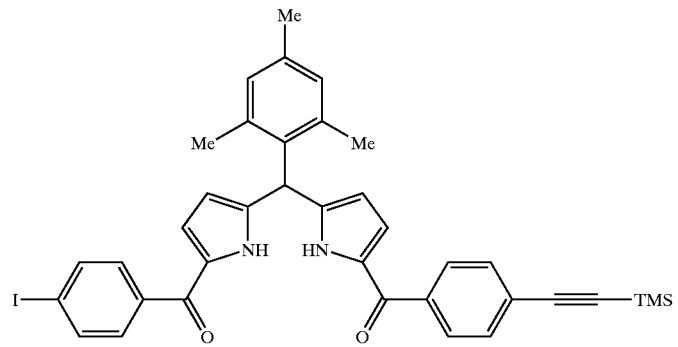
28
TBAF on silica
CHCl₃
rt, 1 h, 97%

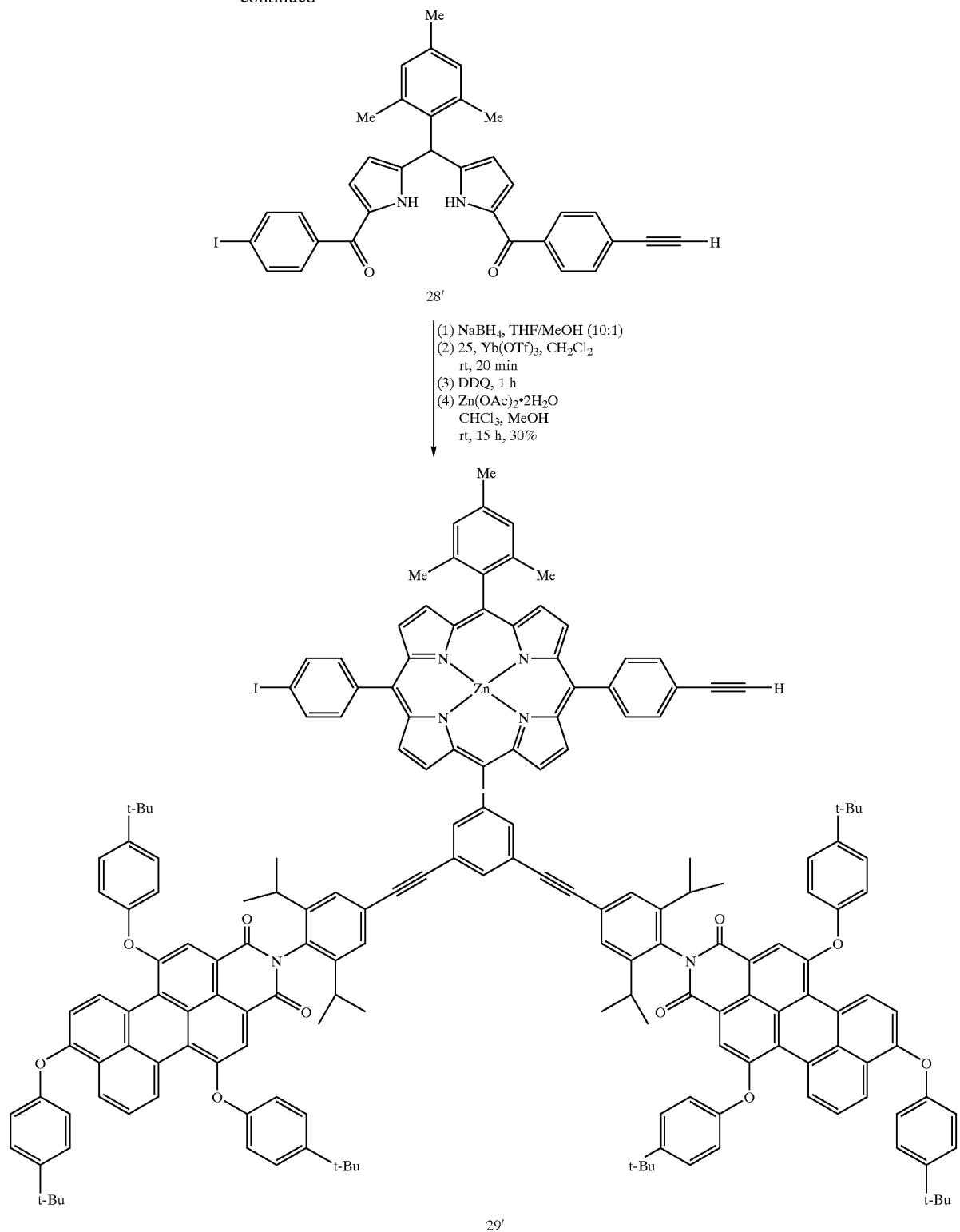

Reduction of diacyl dipyrromethane 26' using excess NaBH$_4$ in THF/MeOH (10:1) afforded the corresponding dipyrromethane-dicarbinol. The dicarbinol was then condensed with perylene-dipyrromethane 25 using Yb(OTf)$_3$ (3.2 mM) (Geier, G. R. III et al., *J. Porphyrins Phthalocyanines* 2001, 5, 810–823) in CH$_2$Cl$_2$. Oxidation with DDQ followed by zinc metalation afforded perylene-porphyrin building block 27' in 36% yield. Perylene-porphyrin 27' bears two ethynylphenyl synthetic handles in a trans-configuration, thereby enabling a Glaser reaction to produce perylene-porphyrin polymers.

An ABCD-porphyrin bearing two perylenes was prepared as shown in Scheme 17. Diacyldipyrromethane 28 (Rao, P. D. et al., *J. Org. Chem.* 2000, 65, 7323–7344) was treated with TBAF on silica (1.0–1.5 mmol F⁻/g resin) to afford diacyldipyrromethane 28' in 97% yield. Reduction of 28' with excess NaBH$_4$ in THF/MeOH (10:1) afforded the dipyrromethane-dicarbinol as a foam-like solid. Condensation of the dicarbinol with perylene-dipyrromethane 21 under identical conditions as described for 27' [Yb(OTf)$_3$ (3.2 mM), CH$_2$Cl$_2$], followed by oxidation with DDQ and metalation with Zn(OAc)$_2$.2H$_2$O furnished porphyrin 29' in 30% yield. We have also prepared 29' in 12% yield directly from the dicarbinol of the TMS-protected diacyl dipyrromethane 28. In this case an additional step, consisting of TMS deprotection of the zinc porphyrin was needed to furnish the porphyrin 29'. The lower overall yield from 28 as compared with that from 28' is due to the low yield of the TMS cleavage from porphyrin 29 and not to the porphyrin-forming reaction. The resulting perylene-porphyrin building block bears one ethynylphenyl and one iodophenyl functional group in a trans architecture, thereby enabling a Sonogashira reaction to prepare a linear perylene-porphyrin polymer.

A. trans-A$_2$B$_2$-Porphyrin Bearing Four Perylenes (Divergent Architecture). A building block bearing a perylene at each of the 3,5-positions of the two non-linking meso-aryl rings of the trans-porphyrin was also prepared. Our initial synthetic approach called for the monoacylation of perylene-dipyrromethane 25 with S-2-pyridyl 4-ethynylbenzothioate (Rao, P. D. et al., *J. Org. Chem.* 2000, 65, 1084–1092) to yield the corresponding perylene-monoacyl dipyrromethane. Reduction of the latter with NaBH$_4$ followed by self-condensation was expected to yield the trans-A$_2$B$_2$-porphyrin. However, treatment of 25 with EtMgBr followed by cooling to –78° C. and reaction with S-2-pyridyl 4-ethynylbenzothioate afforded starting material 25 rather than the desired perylene-monoacyl dipyrromethane. Accordingly, the target perylene-porphyrin building block was prepared as shown in Scheme 18 (Littler, B. J. et al., *J. Org. Chem.* 1999, 64, 2864–2872). Condensation of dipyrromethane 25 and aldehyde 30 (Austin, W. B. et al., *J. Org. Chem.* 1981, 46, 2280–2286) using TFA in CH$_2$Cl$_2$ at room temperature for 1 h followed by oxidation with DDQ afforded the crude porphyrin mixture. These are the conditions typically employed for reaction of a sterically hindered dipyrromethane with an aldehyde. Although sterically unhindered dipyrromethanes (i.e., no o-substituents on the meso-phenyl ring) typically undergo scrambling under these conditions (Littler, B. J. et al., *J. Org. Chem.* 1999, 64, 2864–2872), analysis of the crude reaction mixture by LD-MS showed no detectable scrambling. The crude porphyrin was metalated with Zn(OAc)$_2$.2H$_2$O to furnish the trans-A$_2$B$_2$-porphyrin building block 31' in 23% yield. This building block bears two ethynylphenyl synthetic handles that can be polymerized using the Glaser reaction.

A dibromo porphyrin building block for use in a Suzuki polymerization was synthesized as shown in Scheme 19. Condensation of bis(perylene)aldehyde 18 with dipyrromethane 32 under TFA catalysis, followed by oxidation with DDQ afforded the crude porphyrin. Metalation using Zn(OAc)$_2$.2H$_2$O in CHCl$_3$/MeOH afforded porphyrin 33 in 43% yield. The two free meso-positions of porphyrin 33 were subsequently brominated using NBS in CHCl$_3$/pyridine (DiMagno, S. G. et al., *J. Org. Chem.* 1993, 58, 5983–5993), affording dibromo porphyrin 34 in 72% yield. Significantly, no bromination at the β-position of the porphyrin or at the electron-rich aryloxy rings was observed under these conditions.

Scheme 18

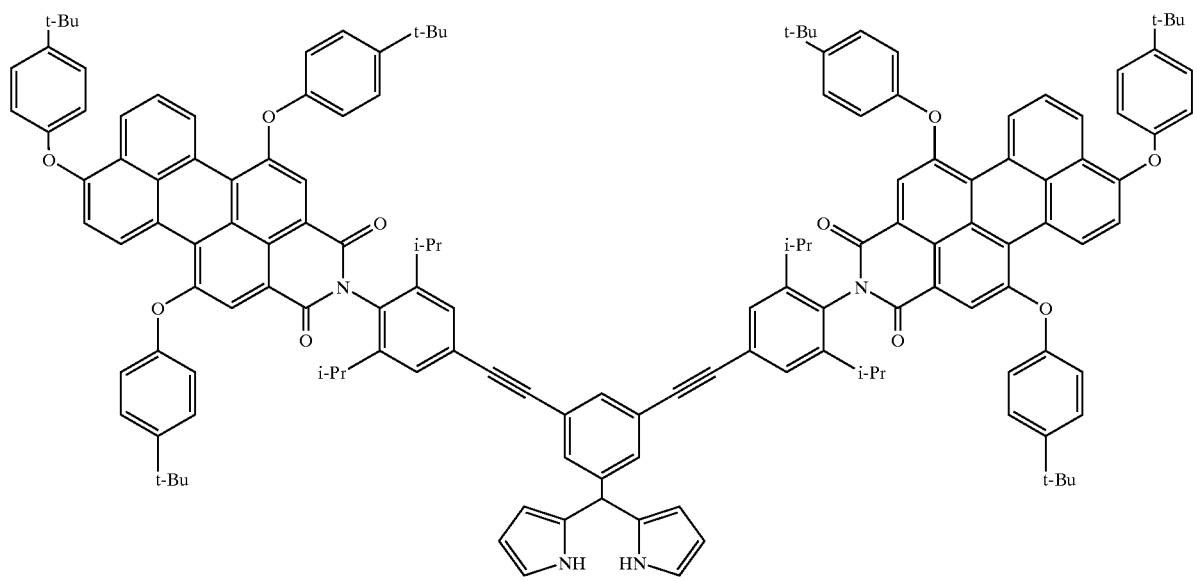

25

-continued
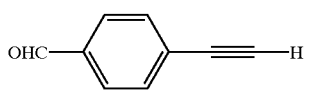
30
(1) TFA, CH$_2$Cl$_2$
    rt, 1 h
(2) DDQ
(3) Zn(OAc)$_2$·2H$_2$O
    CHCl$_3$, MeOH
    rt, 15 h, 23%
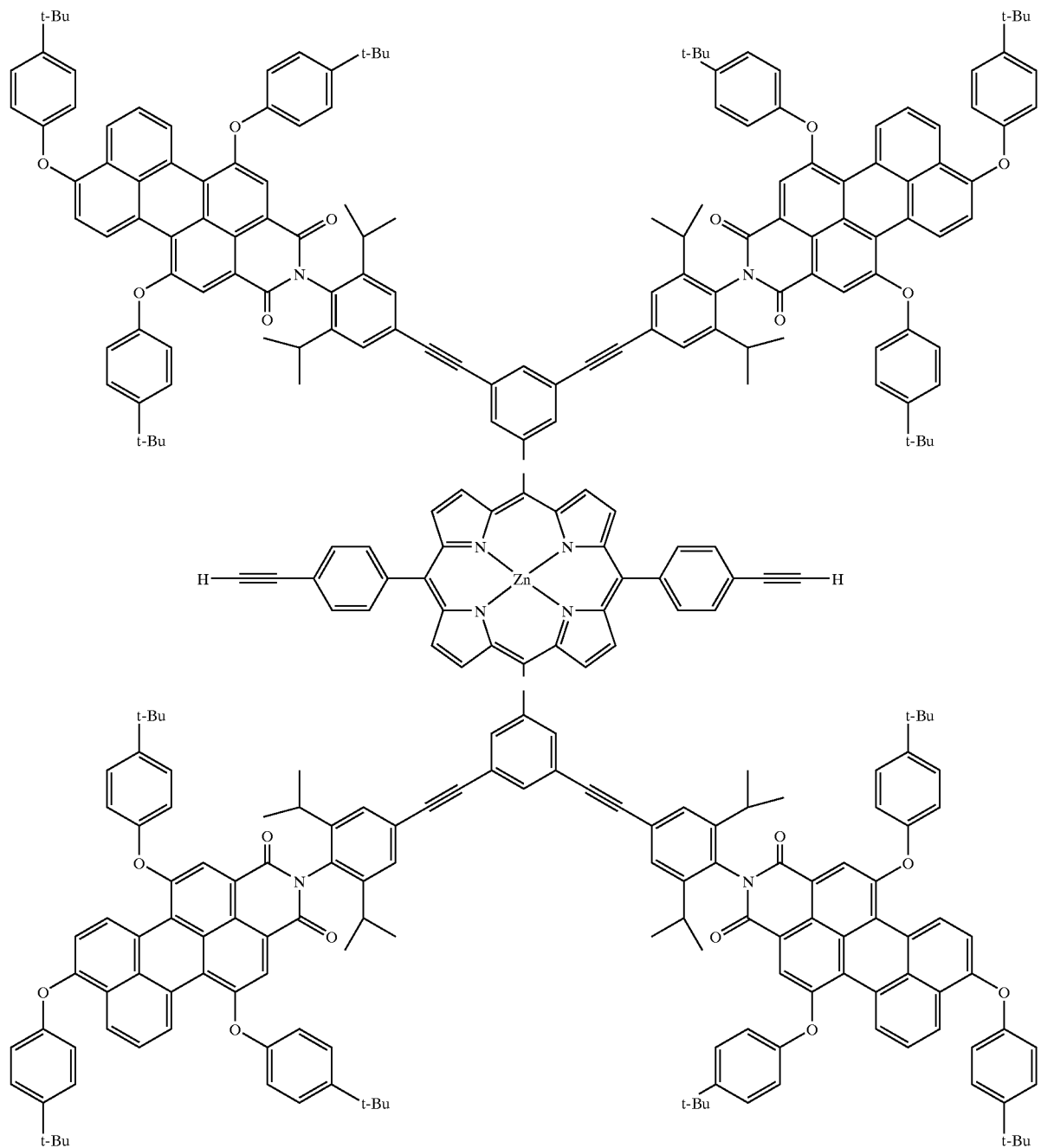
31′

Scheme 19
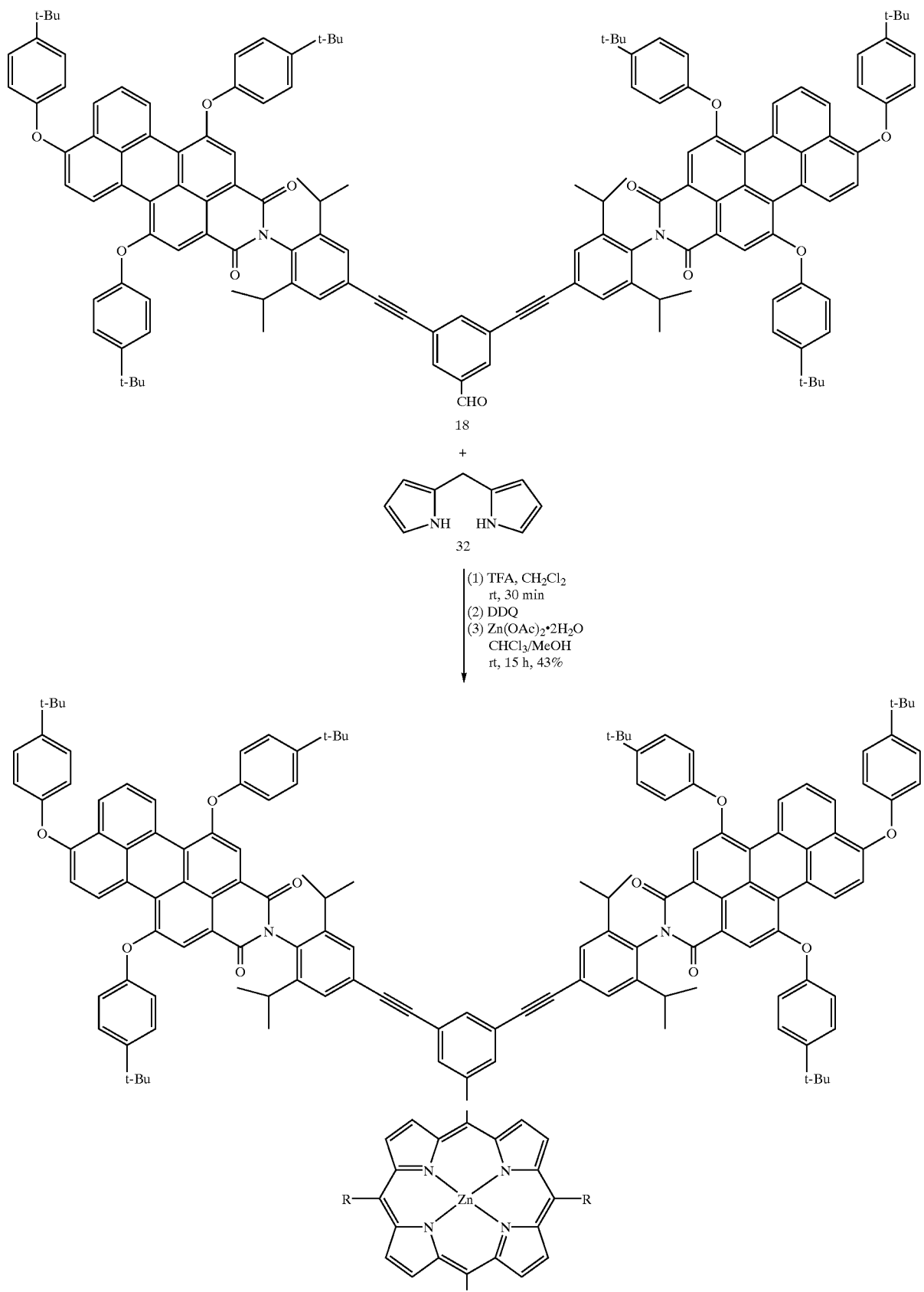

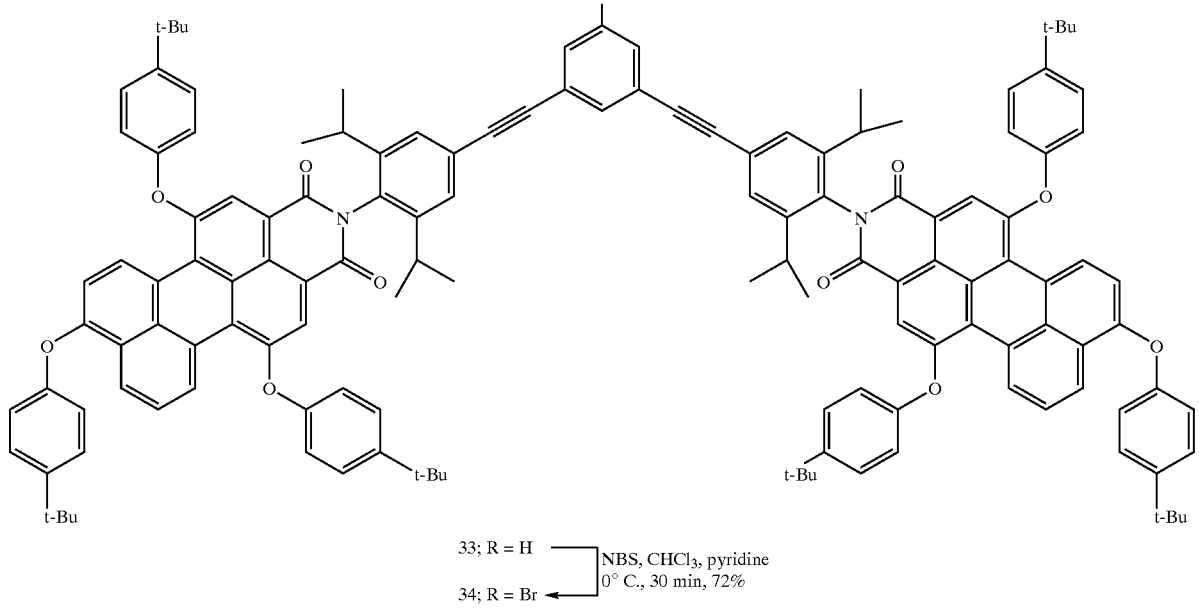

33; R = H
34; R = Br

NBS, CHCl$_3$, pyridine
0° C., 30 min, 72%

Part D. Polymerization of Perylene-Porphyrin Building Blocks. In this section, the multiperylene-porphyrin building blocks prepared in part C were employed in Suzuki, Sonogashira, or Glaser coupling reactions, affording oligomers joined by p-phenylene (p), 4,4'-diphenylethyne (dpe), or 4,4'-diphenylbutadiyne (dpb) linkers, respectively. This work establishes the basis for using light-harvesting rods in molecular-based solar cells. For applications in light-harvesting systems, soluble oligomers comprised of 20–30 porphyrins are ideal. Our goals were to investigate the utility of the building blocks in several different polymerization schemes, including the Glaser, Sonogashira, and Suzuki reactions. The issues we sought to address included the stability of the building blocks to the conditions employed in the coupling reactions, the size of the oligomers that could be readily produced, the solubility of the oligomers, and the absorption and fluorescence properties of the oligomers. A summary of the polymerizations that were carried out is shown in Table 5.

Scheme 20

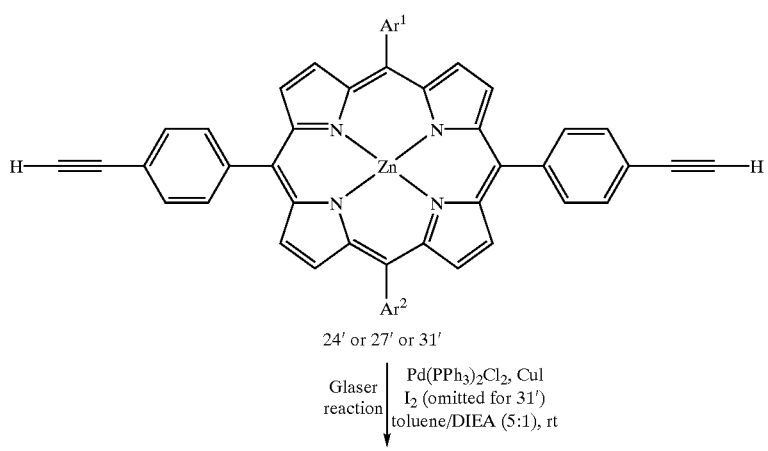

24' or 27' or 31'

Glaser reaction: Pd(PPh$_3$)$_2$Cl$_2$, CuI
I$_2$ (omitted for 31')
toluene/DIEA (5:1), rt -continued

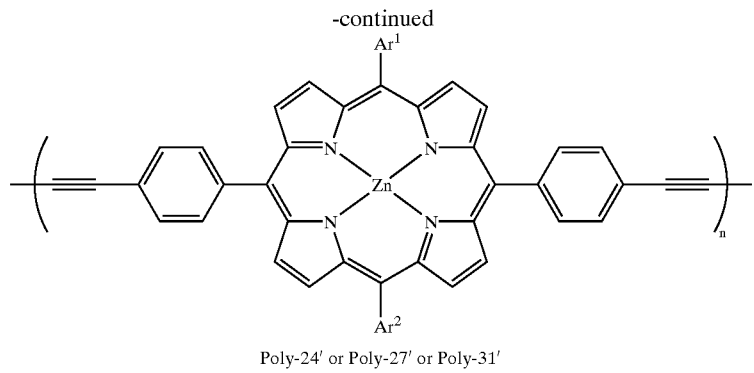

Poly-24' or Poly-27' or Poly-31'

Figure 3:
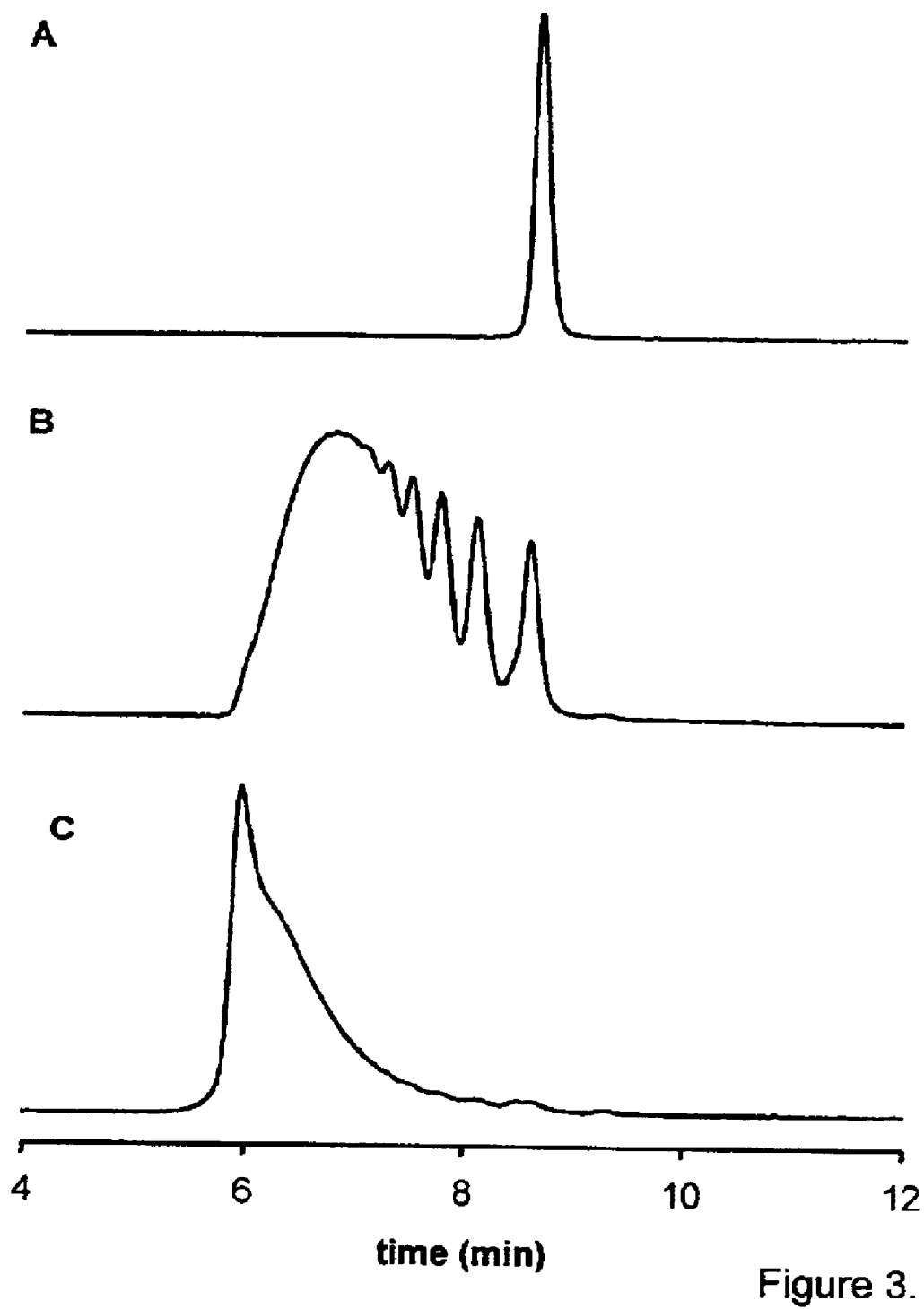
FIG. 3. Analytical SEC traces of the Glaser polymerization of 31' affording the diphenylbutadiyne-linked polymer. Each porphyrin bears two perylenes. (A) Starting porphyrin 31'. (B) Reaction mixture after 10 min. (C) Final reaction mixture after 20 min. Each chromatogram is normalized. Each chromatogram was obtained using a $10^3$ Å column with absorption spectral detection (uncorrected).

Glaser polymerizations were performed with the diethynyl porphyrins 24', 27', and 31' (Scheme 20). In each case, the polymerization was performed at room temperature in the presence of air with the diethynylporphyrin at a concentration of 2.5 mM. The conditions for the Glaser polymerization entailed a Pd-mediated method using $Pd(PPh_3)_2Cl_2$, CuI, and $I_2$ in toluene containing N,N-diisopropylethylamine (Liu, Q. and Burton, D. J. *Tetrahedron Lett.* 1997, 38, 4371–4374). We employed these conditions directly for 24' and 27', but omitted the $I_2$ in the reaction of 31'. We found that the reaction proceeded well in the absence of $I_2$, at least with the dilute solutions and small quantities employed in these experiments. The reaction was followed by analytical SEC. The results are shown in FIG. 3 for the reaction of 31'. Within 10 min of reaction, oligomers of significant length were formed. Resolution of distinct oligomers was observed up to the heptamer stage, after which the chromatographic trace showed a continuum (i.e., unresolved oligomers of increased mass). The reaction was stopped after 20 min. The analytical SEC showed the presence of oligomers estimated to comprise at least 10 porphyrin monomers. In each case, the crude reaction mixture was concentrated to near dryness, then treated with THF. In the case of 24', the product did not dissolve in THF but instead formed a dark film on the walls of the flask. However, the products of the polymerization of 27' and 31' did dissolve in THF. In each of the latter two cases, the product was purified by preparative SEC to remove reagents, affording a tight band that was isolated and concentrated to dryness. The resulting polymer was twice triturated with methanol, centrifuged, and the supernatant was decanted. The same process was then performed with hexanes, affording a purple powder. The polymer was subsequently dissolved in toluene, THF, or $CDCl_3$ and examined by absorption spectroscopy, analytical size exclusion chromatography (SEC) (del Rosario Benites, M. et al., *J. Mater. Chem.* 2002, 12, 65–80), $^1$H NMR spectroscopy, and MALDI-MS. In each case, the MALDI-MS was rather uninformative as a series of molecule ion peaks was not observed. The absorption spectrum showed the presence of the broad perylene absorption and the porphyrin Soret band, which was broadened and split compared with that of the monomer. The analytical SEC trace confirmed the presence of oligomers of substantial size given the rapid elution time of the major peak, and the presence of a series of weak peaks on the low molecular weight side of the major band that could be assigned to oligomers from dimer-hexamer.

Figure 4:
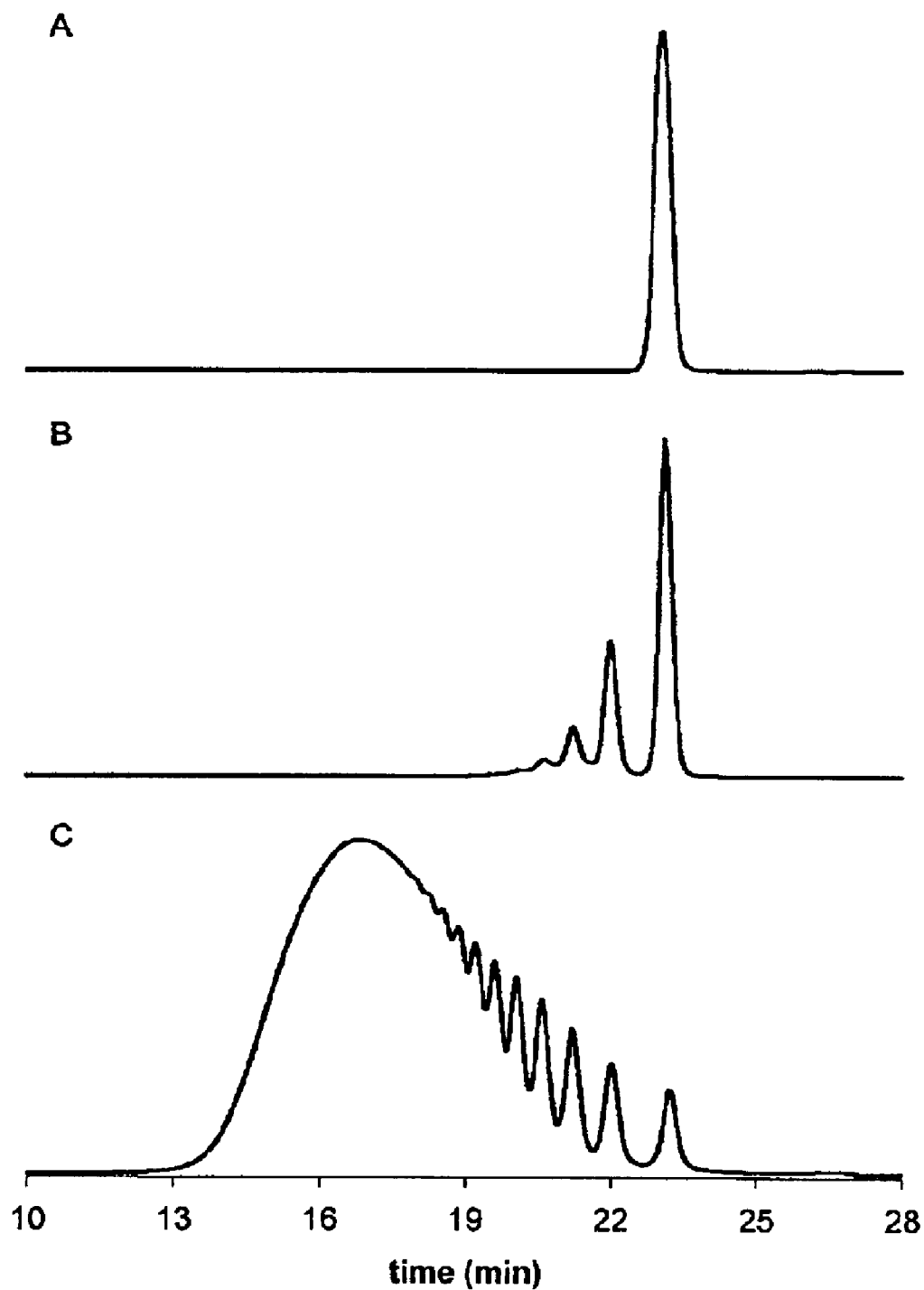
FIG. 4. Analytical SEC traces of the Sonogashira polymerization of 29' affording the diphenylethyne-linked polymer. Each porphyrin bears two perylenes. (A) Starting porphyrin 29'. (B) Reaction mixture after 5 h. (C) Final reaction mixture after 22 h. Each chromatogram is normalized. Each chromatogram was obtained using a $10^3$ Å column and a $10^4$ Å column in series with absorption spectral detection (uncorrected).

A Sonogashira polymerization was carried out on 29' as shown in Scheme 21 using new conditions identified in our laboratory based on model studies of dyad formation. We have previously identified suitable conditions for copper-free Pd-mediated coupling reactions of ethynyl and iodo-substituted porphyrins in dilute solution (Wagner, R. W. et al., *Chem. Mater.* 1999, 11, 2974–2983). The refined conditions, which also are copper-free, employ $Pd_2(dba)_3$ (15 mol %) and $AsPh_3$ (120 mol %) in toluene/triethylamine (5:1) at room temperature with the porphyrin at a concentration of 2.5 mM in an anaerobic atmosphere (Schlenk line). The analytical SEC traces showing the progress of the reaction is displayed in FIG. 4. Resolution of distinct oligomers was observed up to the heptamer stage, after which the chromatographic trace showed a continuum (i.e., unresolved oligomers of increased mass). The crude product was worked up and analyzed in the same manner as described for the products of the Glaser polymerizations of 27' and 31'. The analytical SEC showed the presence of oligomers estimated to comprise at least 10 porphyrin monomers.

The Suzuki polymerization of 34 and 35 is shown in Scheme 22. The reaction was carried out under the conditions employed for Suzuki couplings of porphyrins (Yu, L. and Lindsey, J. S. *Tetrahedron* 2001, 57, 9285–9298). The reaction conditions employ $Pd(PPh_3)_4$ and $K_2CO_3$ (8 equiv) in toluene/DMF (2:1) at 90° C. Under these reaction conditions, only small amounts of oligomers (2–5 units) were detected by analytical SEC, even after prolonged reaction times (48 h). After several hours, analytical SEC showed the presence of additional peaks due to species of apparently smaller size than the starting monomer. Absorption spectral analysis of some of these peaks revealed broad perylene bands with no porphyrin absorption, indicating some decomposition of the monomer under these reaction conditions. Therefore, further Suzuki polymerizations were not attempted.

The solubility of each of the four polymers (Poly-24', Poly-27', Poly-29', Poly-31', Poly-34) prepared was assessed in four typical organic solvents spanning a range of polarity, including toluene, tetrahydrofuran, chloroform, and benzonitrile. Rather than attempting to determine the maximum solubility, we sought to assess an operational solubility for routine handling, including chromatography, characterization, and processing.

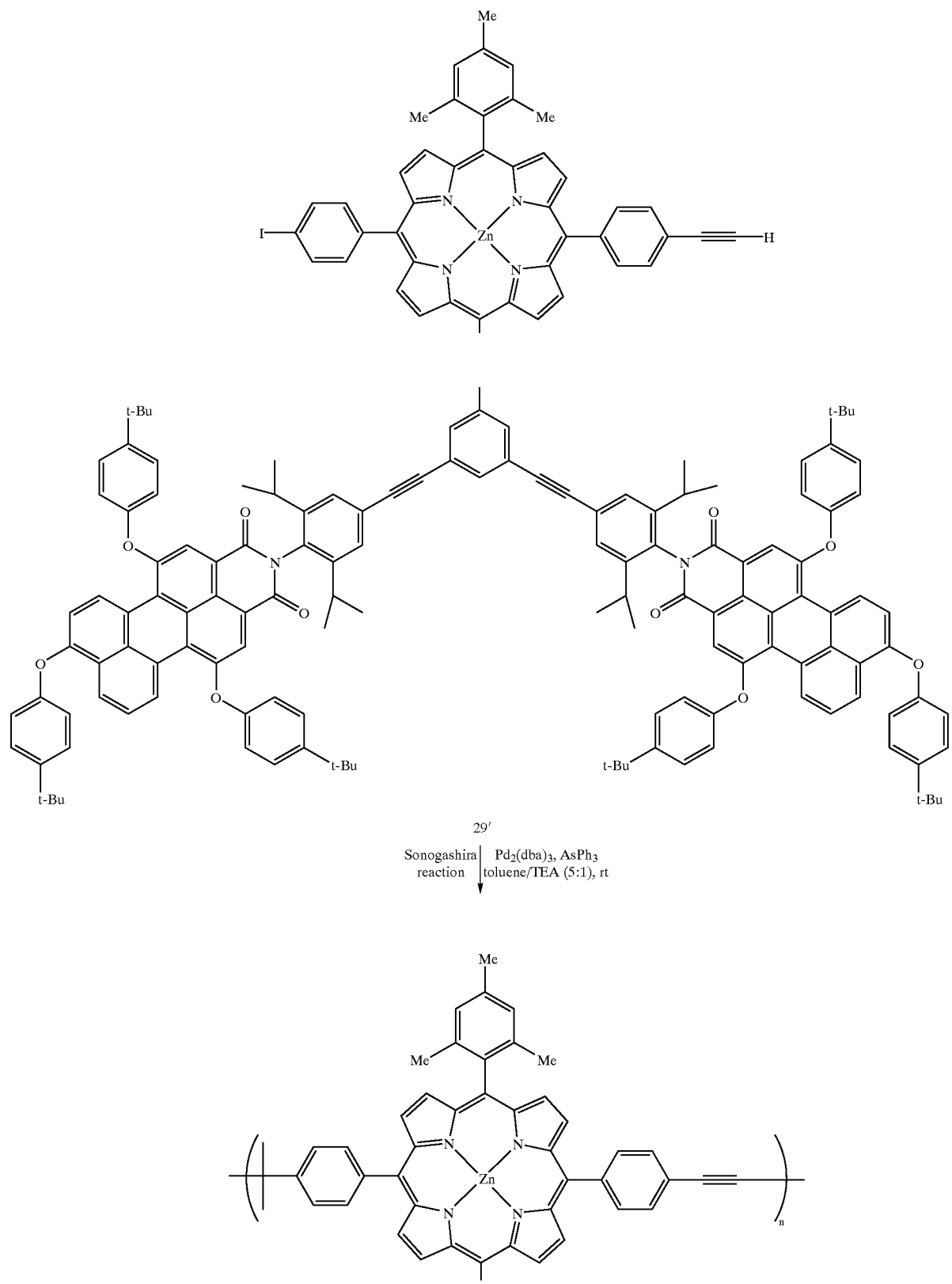

-continued
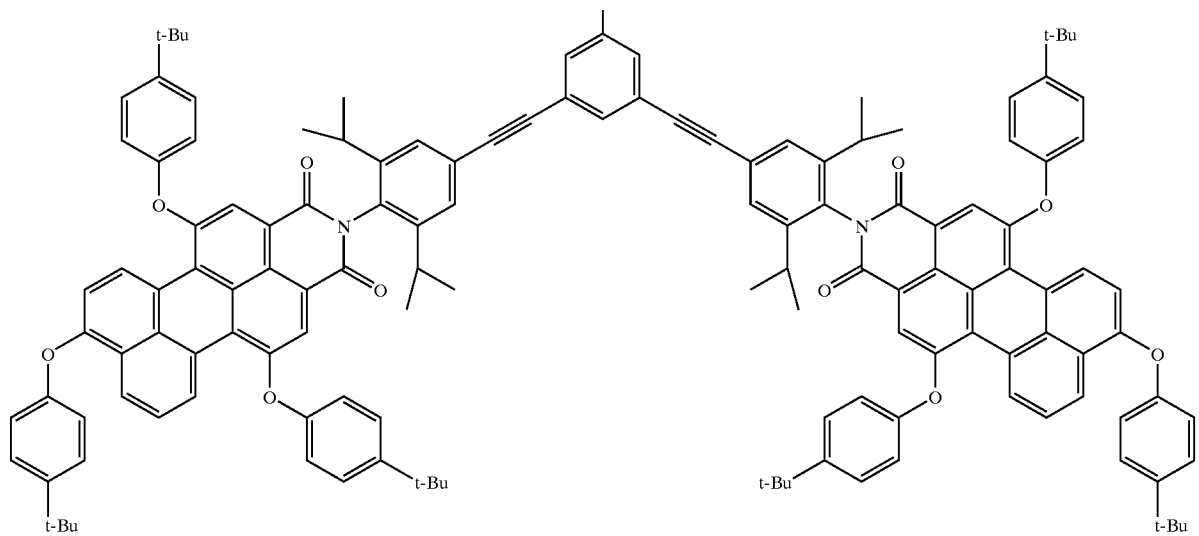
Poly-29'
Scheme 22
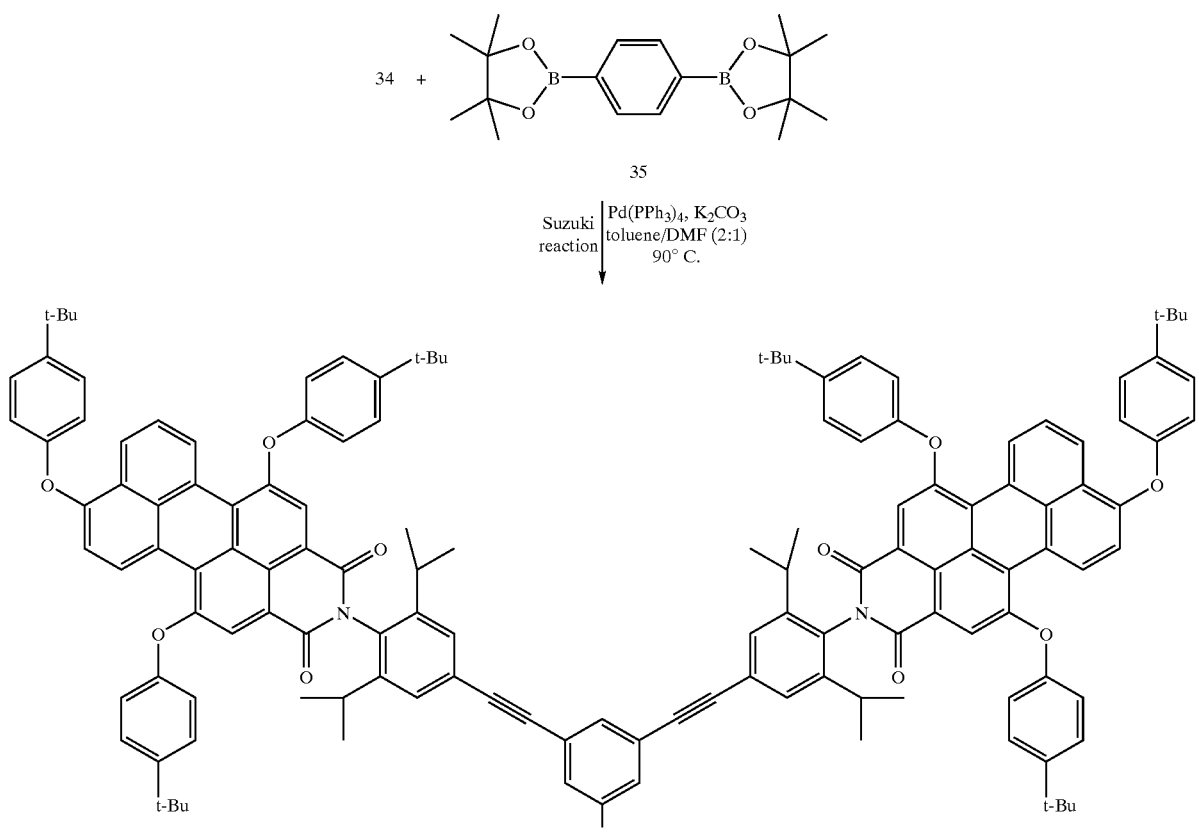
Suzuki reaction: Pd(PPh$_3$)$_4$, K$_2$CO$_3$
toluene/DMF (2:1)
90° C.

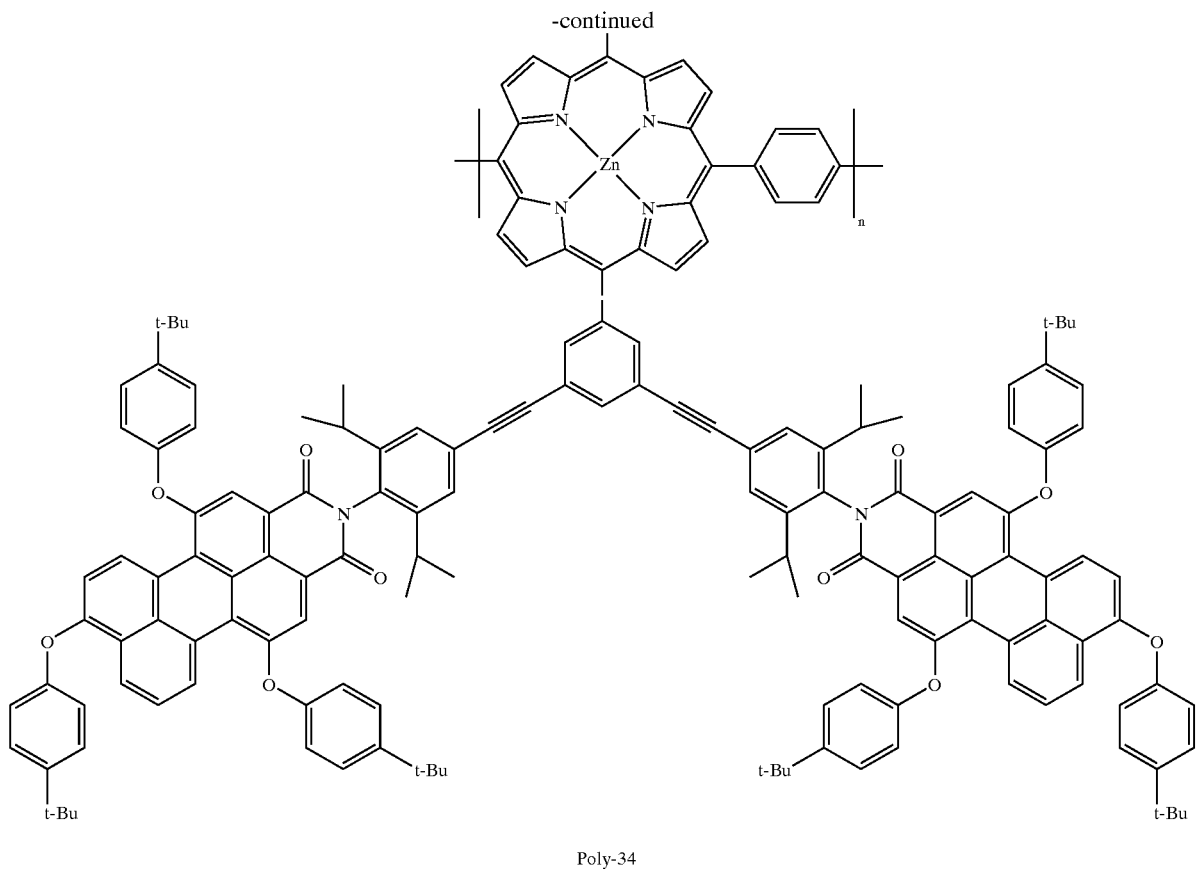

Poly-34

Thus, we elected to determine whether the dry polymer material would dissolve at a concentration of 2.5 mM within one minute upon treatment with a given solvent at room temperature. The resulting samples were examined visually and classified as completely soluble, partially soluble, or insoluble. The results of this survey are shown in Table 6. Poly-27' and poly-31' each were soluble (at 2.5 mM) in toluene, THF, and chloroform, but only partially soluble in benzonitrile. Poly-29' was partially soluble in all four solvents examined. The higher solubility of poly-27' compared to poly-29' (both have two perylenes per porphyrin) may be attributed to the different linkers for each polymer (dpb vs. dpe), respectively, given that the dpb linker provides additional bending about the ethynyl carbons. Poly-31' was the most soluble of the three samples, which is likely due to the presence of four perylenes per porphyrin and to the dpb linker.

Part E. A chief challenge in working with perylene-imide dyes is to overcome their intrinsically low solubility. A widespread approach with perylene-bis(imide) dyes has been to incorporate 2,5-di-tert-butyl (Langhals, H. *Nachr. Chem. Tech. Lab.* 1980, 28, 716–718) or 2,6-diisopropyl (Quante, H. and Muillen, K. *Angew. Chem.* 1995, 107, 1487–1489) substituents on aryl groups located at the N-imide positions. The absorption and emission characteristics of perylene-imide dyes are little affected by the presence of solubilizing substituents at the imide positions because of the nodes present at the imide nitrogen in both the HOMO and LUMO (Langhals, H., et al., *Spectrochim. Acta* 1988, 44A, 1189–1193; Adachi, M. et al., *J. Phys. Chem.* 1995, 99, 14240–14246.). The same tactic of using alkylated N-aryl groups has been carried over to the perylene-monoimide dyes, but additional solubilizing features also have been sought by introducing aryloxy substituents at the perimeter of the perylene (Quante, H. and Muillen, K. *Angew. Chem. Int. Ed. Engl.* 1995, 34, 1323–1325; Holtrup, F. O., et al., *Chem. Eur. J.* 1997, 3, 219–225). The aryloxy substituents cause a bathochromic shift of the absorption and emission spectra.

In the syntheses of perylene mono-imide dyes PMI-7–PMI-12' and in other examples published for perylene mono-imide dyes, the yields were generally acceptable, but a number of reactions employed elaborate chromatography and multiple aqueous/organic extraction schemes for purification. Perylene-monoimide dyes typically can be readily precipitated but crystallize poorly. We have developed routes for the synthesis of a perylene-monoimide dye similar to PMI-12' but lacking the isopropyl groups on the N-aryl unit (39). The synthesis of 39 employs procedures that are rapid and amenable to scale up in lieu of column chromatography and aqueous/organic extraction schemes (see Scheme 23).

Scheme 23

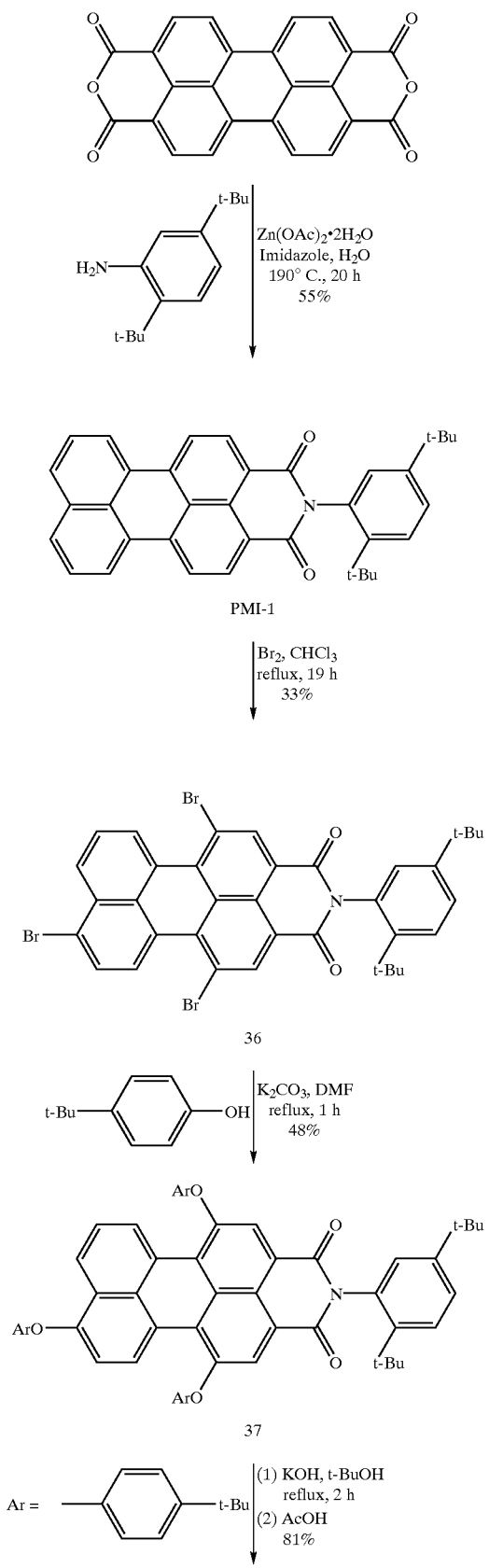

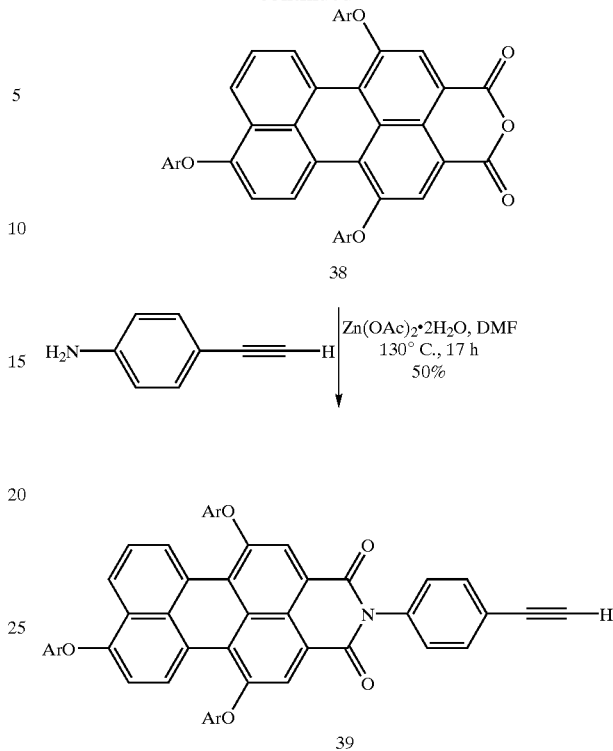

The procedures include selective precipitation followed by filtration, trituration of solids followed by filtration, and vacuum filtration over short silica pads. The approaches described herein provided straightforward access to a key perylene-monoimide building block and may prove applicable in the syntheses of a variety of perylene-imide dyes.

Perylene-3,4:9,10-tetracarboxylic dianhydride is available commercially in large quantities and has been used as the starting point in the synthesis of the mono-imide PMI-1 (Feiler, L., et al., *Liebigs Ann.* 1995, 1229–1244). The latter has been used to prepare the tribromo mono-imide 36 (Quante, H. and Mullen, K. *Angew. Chem. Int. Ed. Engl.* 1995, 34, 1323–1325; Gosztola, D. et al., *J. Am. Chem. Soc.* 1998, 120, 5118–5119), a versatile intermediate in the synthesis of perylene-monoimide dyes (Just, E. M.; Wasielewski, M. R. *Superlatt. Microstr.* 2000, 28, 317–328; Hayes, R. T. et al., *J. Am. Chem. Soc.* 2000, 122, 5563–5567; Lukas, A. S. et al., *J. Phys. Chem. B* 2002, 106, 1299–1306). The former reaction employed extensive extraction followed by column chromatography, while the latter relied on column chromatography to obtain the desired product. We followed the literature procedures for the synthetic reactions for preparing PMI-1 and 36 but modified the workup procedures. Thus, treatment of perylene-3,4:9,10-tetracarboxylic dianhydride with 2,5-di-tert-butylaniline in the presence of $Zn(OAc)_2 \cdot 2H_2O$ in $H_2O$ and imidazole at 190° C. afforded a mixture of the perylene-bis(imide) PDI-1 and the desired perylene-monoimide PMI-1 (Scheme 2). The crude product was precipitated by addition of aqueous acid and collected by filtration, and dried. A solution of the crude material was vacuum filtered through a pad of silica, enabling removal of a smaller amount of perylene formed by exhaustive decarboxylation. The filtrate ($CH_2Cl_2$) contained the bis(imide) PDI-1 and the mono-imide PMI-1. Addition of methanol gave some selectivity in precipitation, affording PMI-1 in 55% yield and 87% purity (13% of PDI-1 also was present). While repeated fractional precipitation could afford a more pure product, the crude material was used directly in the bromination process because the bis(imide) PDI-1 is (1) unreactive toward bromination, and (2) easily removed in the workup of the tribrominated product 36.

The crude sample of PMI-1 was treated with $Br_2$ in $CHCl_3$ under reflux. TLC analysis showed two major products with similar $R_f$ values and unreacted PDI-1 as a minor, more polar component. Vacuum filtration through a pad of silica yielded a filtrate containing the desired 36 in ~90% purity. Evaporation of the filtrate, partial dissolution in $CH_2Cl_2$, and addition of hexanes yielded 36 as a solid in 33% yield that was collected by filtration. It is noteworthy that other well-known bromination conditions such as use of $Br_2$ with $FeBr_3$ or NBS with benzoyl peroxide failed to give the desired product.

Compound 36 was treated with 4-tert-butylphenol and $K_2CO_3$ in anhydrous DMF under reflux. The reaction at lower temperature affords the 1,6-diaryloxy-9-bromo derivative (Quante, H. and Muillen, K. *Angew. Chem. Int. Ed. Engl.* 1995, 34, 1323–1325; Gosztola, D. et al., *J. Am. Chem. Soc.* 1998, 120, 5118–5119). The addition of water followed by filtration removed the DMF, salts, and the excess 4-tert-butylphenol, affording 37 and a major byproduct. Vacuum filtration through a pad of silica gave the filtrate containing the desired 37 in 48% yield. Compound 37 was extremely soluble in common organic solvents, including methanol or hexanes. Therefore, further purification by trituration or precipitation was not attempted, and 37 was used in the next step.

The next step in the synthesis entails the conversion of the imide to the anhydride. This transformation proceeds through a base-mediated hydrolysis of the imide yielding the dicarboxylate followed by acid-mediated dehydration of the dicarboxylate (Feiler, L., et al., *Liebigs Ann.* 1995, 1229–1244). Compound 37 was refluxed in the presence of KOH in 2-methyl-2-propanol followed by treatment with acetic acid. The addition of water yielded the anhydride as the dominant product and small amounts of a non-polar byproduct (unknown) and a very polar byproduct (presumably the diacid). The crude material was dissolved and vacuum filtered through a pad of silica, yielding a filtrate containing the anhydride 38 and a trace amount of the polar byproduct. Evaporation to dryness, trituration with a small amount of methanol, and filtration afforded 38 in 81% yield. Removal of both impurities at this stage is essential for being able to purify the product of the next synthetic step.

Compound 38 was condensed with 4-ethynylaniline in the presence of $Zn(OAc)_2.2H_2O$ in anhydrous DMF. The addition of water yielded a precipitate consisting of the desired ethynyl-perylene as the dominant product, a small amount of perylene starting material, and an unknown byproduct. TLC analysis showed the three components to have similar polarities. The precipitate was collected and washed with aqueous methanol to remove unreacted 4-ethynylaniline. The precipitate was dissolved and vacuum filtered through a pad of silica, affording a filtrate containing relatively pure ethynyl-perylene. The filtrate was evaporated and triturated with methanol to afford the desired ethynyl-perylene 39 in 50% yield.

In summary, the synthesis of the ethynyl-perylene 39 was achieved in a time-efficient manner and without laborious separation procedures. The use of vacuum filtration, precipitation, and trituration proved to be a viable substitute for chromatography and extraction procedures. Furthermore, compound 38 is a versatile intermediate for condensation with a variety of amino components.

N-(2,5-Di-tert-butylphenyl)perylene-3,4-dicarboxylic imide (PMI-1). Following the procedure of Langhals (Feiler, L., et al., *Liebigs Ann.* 1995, 1229–1244), samples of perylene-3,4:9,10-tetracarboxylic dianhydride (11.0 g, 28.0 mmol), 2,5-di-tert-butylaniline (3.15 g, 15.3 mmol), $Zn(OAc)_2.2H_2O$ (1.32 g, 6.01 mmol), imidazole (56.1 g), and $H_2O$ (24 mL) were placed in a heavy-walled flask with a screw cap. The mixture was stirred at 190° C. After 20 h, the reaction mixture was cooled to room temperature. A second batch on the same scale was treated in the same manner. A solution of 2 N aqueous HCl/methanol [300 mL, (1/1)] was added to each reaction mixture. The resulting mixtures were vacuum-filtered one after the other over a single fritted glass filter. The filtered solid obtained was washed with $H_2O$/methanol (1:1) and dried in an oven at 130° C. TLC analysis (silica, $CH_2Cl_2$) showed the presence of the title compound (Rf=0.52, red) and PDI-1 (Rf=0.21, orange). The crude solid was dissolved in $CH_2Cl_2$ (200 mL) and vacuum-filtered through a pad of silica (6.0×6.0 cm, swelled with $CH_2Cl_2$) in a fritted glass filter with $CH_2Cl_2$ (500 mL). A less polar yellowish byproduct (perylene itself) eluted first and was not collected. Subsequent elution with $CH_2Cl_2$ (800 mL) afforded the title compound. The filtrate was concentrated to a volume of ~200 mL. Then methanol (200 mL) was added. A red solid which precipitated upon standing at 0° C. was collected by filtration (8.51 g, 55%). The purity of the title compound obtained was estimated to be 87% [PDI-1 accounts for the remaining 13%] by $^1H$ NMR spectroscopy. This material was used without further purification in the next step. 1,6,9-Tribromo-N-(2,5-di-tert-butylphenyl)perylene-3,4-dicarboxylic imide (36). Following the approach outlined by Muillen (Quante, H. and M üllen, K. *Angew. Chem. Int. Ed. Engl.* 1995, 34, 1323–1325) and the procedure described in detail by Wasielewski (Gosztola, D., et al., *J. Am. Chem. Soc.* 1998, 120, 5118–5119), a mixture containing crude PMI-1 (9.28 g, 18.2 mmol) and $Br_2$ (14.9 mL, 291 mmol) in $CHCl_3$ (280 mL) was refluxed for 19 h. The reaction mixture was concentrated to dryness. TLC analysis (silica, $CH_2Cl_2$) showed the presence of the title compound ($R_f$=0.83, red), a major byproduct ($R_f$=0.73, orange), and residual PDI-1 ($R_f$=0.20, orange). The crude solid was dissolved in toluene/hexanes [400 mL (1:1)] and vacuum-filtered through a pad of silica [6.0×6.0 cm, swelled with toluene/hexanes (1:1)] in a fritted glass filter. Elution with toluene/hexanes [1.0 L (1:1)] removed a yellowish material; then elution with toluene/hexanes [1.5 L (1:1)] afforded the title compound. The residual PDI-1 in the starting sample of remained at the top of the silica pad. The filtrate, now containing the title compound in ~90% purity and an unknown compound constituting the remaining ~10%, was concentrated to dryness. Addition of $CH_2Cl_2$ (100 mL) yielded a slurry, to which hexanes (200 mL) was added. The resulting red solid was collected by filtration (4.52 g, 33%). Analytical data were identical to those reported previously (Gosztola, D., et al., *J. Am. Chem. Soc.* 1998, 120, 5118–5119).

1,6,9-Tris(4-tert-butylphenoxy)-N-(2,5-di-tert-butylphenyl)perylene-3,4-dicarboxylic imide (37). Following a procedure described for diaryloxylation (Gosztola, D., et al., *J. Am. Chem. Soc.* 1998, 120, 5118–5119) but at higher temperature and with excess 4-tert-butylphenol to achieve triaryloxylation, a mixture of 36 (5.19 g, 6.95 mmol), 4-tert-butylphenol (12.5 g, 83.4 mmol), and $K_2CO_3$ (13.8 g, 100 mmol) in anhydrous DMF (300 mL) was refluxed for 1 h. The reaction mixture was cooled to room temperature. TLC analysis [silica, $CH_2Cl_2$/hexanes (1:2)] showed the presence of the title compound ($R_f$=0.37, magenta) and a major byproduct ($R_f$=0.23, purple). Water (300 mL) was added to the reaction mixture. The resulting solid was collected by vacuum filtration in a fritted glass filter, washed with $H_2O$/methanol [300 mL (1:1)] while on the filter, and then dried in an oven at 130° C. The crude solid consisted of the title compound and a major byproduct. The crude solid was dissolved in $CH_2Cl_2$/hexanes [100 mL (1:4)] and vacuum filtered through a pad of silica [6.0×6.0 cm, swelled with $CH_2Cl_2$/hexanes (1:4)] on a fritted glass filter using $CH_2Cl_2$/hexanes [2.0 L (1:4)]. The byproduct remained on the silica pad. The filtrate was concentrated to give a magenta solid (3.22 g, 48%): mp 203–205° C.; $^1$H NMR δ1.25 (s, 9H), 1.28 (s, 9H), 1.31 (s, 9H), 1.34 (s, 9H), 1.35 (s, 9H), 6.89–6.93 (m, 2H), 7.02 (d, J=8.8 Hz, 2H), 7.08 (d, J=8.8 Hz, 2H), 7.09 (d, J=8.8 Hz, 2H), 7.37 (d, J=8.8 Hz, 2H), 7.40–7.44 (m, 5H), 7.53 (d, J=8.8 Hz, 1H), 7.62–7.67 (m, 1H), 8.28 (s, 1H), 8.31 (s, 1H), 8.48 (d, J=8.1 Hz, 1H), 9.26 (d, J=8.8 Hz, 1H), 9.46 (d, J=8.1 Hz, 1H); MALDI-MS (dithranol) obsd 805.4 [(M−4-tert-butylphenol)$^+$], 897.5 [(M-tert-butyl)$^+$], 953.5 [M$^+$], 1101.4 [(M+148)$^+$]; FAB-MS obsd 953.4987, calcd 953.5019 ($C_{66}H_{67}NO_5$); $\lambda_{abs}$=415, 531 nm; $\lambda_{em}(\lambda_{ex}$=500 nm) 571 nm.

1,6,9-Tris(4-tert-butylphenoxy)-N-(2,5-di-tert-butylphenyl)perylene-3,4-dicarboxylic anhydride (38). Following a standard procedure (Gosztola, D., et al., *J. Am. Chem. Soc.* 1998, 120, 5118–5119; Feiler, L. et al., *Liebigs Ann.* 1995, 1229–1244), a mixture of 37 (3.15 g, 3.30 mmol) and KOH (9.51 g, 169 mmol) in 2-methyl-2-propanol (200 mL) was refluxed for 2 h. The hot reaction mixture was poured into acetic acid (400 mL) and the mixture was vigorously stirred for 5 min at room temperature. To this mixture was added $H_2O$ (600 mL). The resulting precipitate was removed by vacuum filtration. The precipitate was washed with $H_2O$, washed with a minimum volume of methanol (~30 mL) to remove any residual reagents, and dried in vacuo. TLC analysis [silica, $CH_2Cl_2$/hexanes (1:1)] showed the presence of a small amount of a byproduct ($R_f$=0.92, magenta) and the title compound ($R_f$=0.57, magenta). The crude solid was dissolved in $CH_2Cl_2$/hexanes [150 mL (1:3)] and vacuum filtered through a pad of silica (6.0×6.0 cm, swelled with hexanes) on a fritted glass filter. Elution with $CH_2Cl_2$/hexanes [2.0 L (2:3)] removed a less polar byproduct, then $CH_2Cl_2$/hexanes [700 mL (2:1)] eluted the title compound. The filtrate was concentrated to dryness. The solid was triturated with a small volume of methanol then filtered, affording a deep-purple solid (2.04 g, 81%): mp 152–154° C.; $^1$H NMR δ1.34 (s, 9H), 1.35 (s, 9H), 1.36 (s, 9H), 6.89 (d, J=8.8 Hz, 1H), 7.00 (d, J=8.8 Hz, 2H), 7.06 (d, J=8.8 Hz, 2H), 7.10 (d, J=8.1 Hz, 2H), 7.39 (d, J=8.8 Hz, 2H), 7.43 (d, J=8.8 Hz, 2H), 7.44 (d, J=8.8 Hz, 2H), 7.63–7.68 (m, 1H), 8.18 (m, 1H), 8.20–8.21 (m, 1H), 8.53 (d, J=8.1 Hz, 1H), 9.26 (d, J=8.8 Hz, 1H), 9.46 (d, J=8.1 Hz, 1H); MALDI-MS (dithranol) obsd 765.2 [M$^+$]; FAB-MS obsd 766.3318, calcd 766.3294 ($C_{52}H_{46}O_6$); $\lambda_{abs}$=410, 533 nm; $\lambda_{em}(\lambda_{ex}$=500 nm) 578 nm.

1,6,9-Tris(4-tert-butylphenoxy)-N-(4-ethynylphenyl) perylene-3,4-dicarboxylic imide (39). Following a procedure modified from that of Langhals (Feiler, L. et al., *Liebigs Ann.* 1995, 1229–1244) and Wasielewski (Gosztola, D., et al., *J. Am. Chem. Soc.* 1998, 120, 5118–5119), a mixture of 38 (3.25 g, 4.24 mmol), 4-ethynylaniline (1.49 g, 12.7 mmol), and $Zn(OAc)_2 \cdot 2H_2O$ (850 mg, 3.87 mmol) in anhydrous DMF (100 mL) was stirred at 130° C. for 17 h. TLC analysis [silica, $CH_2Cl_2$/hexanes (1:1)] showed the presence of the title compound ($R_f$=0.63, magenta), a small amount of 38 ($R_f$=0.58, magenta), and a small amount of a byproduct ($R_f$=0.50, magenta). The reaction mixture was cooled to room temperature and $H_2O$ (200 mL) was added. The resulting solid was collected by vacuum filtration on a fritted glass filter and washed with $H_2O$/methanol [300 mL (1:1)] to remove 4-ethynylaniline. The damp solid was dissolved in $CH_2Cl_2$ (300 mL). The solution was dried ($Na_2SO_4$), filtered, and the filtrate was concentrated to dryness. The crude solid was dissolved in toluene/hexanes [400 mL (1:1)] and vacuum-filtered through a pad of silica [6.0×6.0 cm, swelled with toluene/hexanes (1:1)] on a fritted glass filter. Elution with toluene/hexanes [1.0 L (1:1)] removed a less polar byproduct, then toluene/hexanes [2.5 L (3:2)] eluted the title compound. The filtrate was concentrated to dryness. The solid was triturated with methanol then filtered, affording a magenta solid (1.84 g, 50%): mp>230° C.; $^1$H NMR δ1.31 (s, 9H), 1.33 (s, 9H), 1.34 (s, 9H), 3.12 (s, 1H), 6.91 (d, J=8.8 Hz, 1H), 7.01 (d, J=8.8 Hz, 2H), 7.07 (d, J=8.1 Hz, 2H), 7.09 (d, J=8.8 Hz, 2H), 7.23–7.26 (m, 2H overlapped with solvent peak), 7.36 (d, J=8.8 Hz, 2H), 7.41 (d, J=8.8 Hz, 2H), 7.42 (d, J=8.1 Hz, 2H), 7.60–7.68 (m, 3H), 8.24 (s, 1H), 8.27 (s, 1H), 8.49 (d, J=8.1 Hz, 1H), 9.28 (d, J=8.8 Hz, 1H), 9.48 (d, J=8.1 Hz, 1H); MALDI-MS (dithranol) obsd 865.4 [M$^+$], 1013.5 [(M+148)$^+$]; FAB-MS obsd 865.3783, calcd 865.3767 ($C_{60}H_{51}NO_5$); $\lambda_{abs}$=412, 532 nm; $\lambda_{em}(\lambda_{ex}$=500 nm) 574 nm.

Conclusion

We have prepared five new perylene-porphyrin building blocks bearing ethynylphenyl, iodophenyl, or bromo substituents at the 5,15 positions of the porphyrin macrocycle. These building blocks serve as monomers in the Glaser, Sonogashira, and Suzuki reactions. We have found that the Glaser polymerization reaction is generally rapid, affording sizeable polyporphyrin arrays at room temperature in a few minutes. The Sonogashira polymerization also produced polyporphyrin arrays, but required much longer reaction times (24 h) at room temperature. The Suzuki polymerization was found to require elevated temperatures and long reaction times (2 days) and still little polymer was formed.

Experimental Section

General. $^1$H (300 or 400 MHz) and $^{13}$C (75 MHz) NMR spectra were recorded in $CDCl_3$ unless noted otherwise. Mass spectra of perylenes, porphyrins, and perylene-porphyrin arrays were obtained by high-resolution fast atom bombardment (FAB-MS), laser desorption mass spectrometry (LD-MS) (Fenyo, D. et al., *J. Porphyrins Phthalocyanines* 1997, 1, 93–99; Srinivasan, N. et al., *J. Porphyrins Phthalocyanines* 1999, 3, 283–291), or MALDI-MS using dithranol as matrix. Absorption and emission spectra were collected in toluene at room temperature unless noted otherwise. Elemental analyses were performed by Atlantic Microlab, Inc. Melting points are uncorrected. Silica gel (Baker 40 μm average particle size) and alumina (Fisher, 80–200 mesh) were used for column chromatography. Preparative SEC was performed using BioRad Bio-Beads SX-1 (200–400 mesh). Analytical SEC was performed using an HP 1090 Liquid Chromatograph (column size =1000 Å; flow rate=0.800 mL/min; solvent=THF; quantitation typically at 424 and 512 nm; reference at 475 or 670 nm; oven temperature 25 or 40° C.) (del Rosario Benites, M. et al., *J. Mater. Chem.* 2002, 12, 65–80). Toluene and triethylamine were freshly distilled from $CaH_2$ and sparged of oxygen prior to use. Chloroform contained 0.8% ethanol as a stabilizer.

Sonogashira coupling reactions. The reactions were performed using a Schlenk line. The conditions for reactions with porphyrins use tris(dibenzylideneacetone)dipalladium (0) (Pd$_2$(dba)$_3$) and the ligand P(o-tol)$_3$ in the absence of any copper reagents (Wagner, R. W. et al., *Chem. Mater.* 1999, 11, 2974–2983). Reactions were typically performed at 2.5 mM reactants in toluene/TEA (5:1 or 10:1). The bromo+ ethyne reactions were carried out at 60° C. to facilitate coupling (Loewe, R. S. et al., *J. Mater. Chem.* 2002, 12, 1530). Palladium insertion and transmetalation have not been observed with these conditions.

All Glaser coupling reactions were performed in air using Pd(PPh$_3$)$_2$Cl$_2$, CuI, and I$_2$ unless noted otherwise (Liu, Q. and Burton, D. J. *Tetrahedron Lett.* 1997, 38, 4371–4374). For both reactions, the concentration of the building blocks was 2.5 mM.

Solubility Experiments. The polymers were assessed for solubility in a given solvent at room temperature. A known quantity of a dry powder (e.g., 2.0 mg) was weighed into a vial. A known volume of solvent (e.g., 200 µL) was added to achieve a target concentration per porphyrin of 2.5 mM. After one minute with occasional manual swirling, the mixture was assessed visually for homogeneity. In this manner, operational solubility at a workable concentration could be established.

Polymerization experiments. Polymerization of the porphyrins was achieved by Pd-mediated coupling under Glaser, Sonogashira, or Suzuki conditions. Sonogashira and Suzuki reactions were carried out on a Schlenk line. Reactions were carried out using 4–7 µmol of porphyrin monomer. For cases where less than 2.0 mg of a coupling reagent was needed, stock solutions were prepared to deliver accurate amounts to the reaction. For example, CuI was dissolved in DIEA to make a 3.8 mM stock solution, I$_2$ was dissolved in toluene to make a 44.9 mM stock solution, and Pd(PPh$_3$)$_2$Cl$_2$ was dissolved in toluene to make a 7.1 mM stock solution. All reactions were monitored by analytical SEC.

Molecular modeling. Intramolecular distances were calculated using PC Model for Windows 7.50.00 (Serena Software, Inc.). Förster calculations were performed using PhotochemCAD (Du, H. et al., *Photochem. Photobiol.* 1998, 68, 141–142).

Fluorescence spectroscopy. Fluorescence quantum yields were determined by ratioing the integrated corrected emission spectrum of the sample to that of ZnTPP. Measurements were performed at room temperature in toluene or benzonitrile.

Non-commercial compounds. Perylenes PMI-1 and PMI-2 (Quante, H. and Müllen, K. *Angew. Chem.* 1995, 107, 1487–1489), PMI-4 (Yang, S. I. et al., *J. Mater. Chem.*, 2001, 11, 2420–2430), PMI-5 (Gosztola, D. et al., *J. Am. Chem. Soc.* 1998, 120, 5118–5119), PMI-6 (Boehm, A. and Helfer, W. U.S. Pat. No. 5,808,073), and PDI-1 (Langhals, H. *Chem. Ber.* 1985, 118, 4641–4645); aldehydes 2-ethynylbenzaldehyde (Wang, X. and Silverman, R. B. *J. Org. Chem.* 1998, 63, 7357–7363), 16 (Li, F. et al., *J. Am. Chem. Soc.* 1998, 120, 10001–10017), and 30 (Austin, W. B. et al., *J. Org. Chem.* 1981, 46, 2280–2286); dipyrromethanes 19 (Rao, P. D. et al., *J. Org. Chem.* 2000, 65, 7323–7344), 26' (Rao, P. D. et al., *J. Org. Chem.* 2000, 65, 7323–7344), and 32 (Littler, B. J. et al., *J. Org. Chem.* 1999, 64, 1391–1396; Wang, Q. M. and Bruce, D. W. *SYNLETT* 1995, 1267–1268) were prepared as described in the literature. Diacyl dipyrromethanes 21 and 28 were prepared following standard methods (Rao, P. D. et al., *J. Org. Chem.* 2000, 65, 7323–7344).

N-(2,6-Diisopropyl-4-bromophenyl)-3,4-perylenedicarboximide (PMI-7). Following the procedure described by Langhals et al., (Feiler, L. et al., *Liebigs Ann.* 1995, 1229–1244), samples of 3,4,9,10-perylenetetracarboxylic dianhydride (4.50 g, 11.5 mmol), 2,6-diisopropyl-4-bromoaniline (1.61 g, 6.28 mmol), Zn(OAc)$_2$.2H$_2$O (1.64 g, 7.47 mmol), imidazole (23 g), and distilled water (9.8 mL) were placed into a heavy-walled reaction vessel. The vessel was sealed tightly with a Teflon screw cap and the flask was placed into a 190° C. oil bath and stirred for 18 h. After cooling, the crude material was passed through a plug of alumina column using chloroform. The filtrate was washed with water, dried, and concentrated. Column chromatography (silica, CHCl$_3$, 8×30 cm) afforded a red solid (1.63 g, 46%): mp>300° C.; $^1$H NMR δ1.17 (d, J=6.9 Hz, 12H), 2.73 (m, 2H), 7.45 (s, 2H), 7.67 (t, J=7.8 Hz, 2H), 7.94 (d, J=8.1 Hz, 2H), 8.49 (m, 4H), 8.66 (d, J=8.1Hz, 2H); FAB-MS obsd 559.1133, calcd, 559.1147 (C$_{34}$H$_{26}$BrNO$_2$); $\lambda_{abs}$ 356, 482, 509 nm; $\lambda_{em}$($\lambda_{ex}$=509 nm) 539, 577 nm.

9-Bromo-N-(2,6-diisopropyl-4-bromophenyl)-3,4-perylenedicarboximide (PMI-8). A solution of PMI-7 (246 mg, 438 µmol) in chlorobenzene (50 mL) was treated with anhydrous K$_2$CO$_3$ (252 mg) followed by Br$_2$ (103 µL, 2.02 mmol). The mixture was stirred at 55° C. for 7 h. The solvent and excess bromine were removed under vacuum. The solid was dissolved in chloroform, washed with water, dried (Na$_2$SO$_4$), and concentrated. Column chromatography (silica, 4×25 cm, CHCl$_3$) afforded a red solid (242 mg, 86%): mp>300° C.; $^1$H NMR δ1.16 (d, J=6.9 Hz, 12H), 2.72 (m, 2H), 7.45 (s, 2H) 7.73 (t, J=9.0 Hz, 1H), 7.91 (d, J=8.4 Hz, 1H), 8.25 (d, J=8.1 Hz, 1H), 8.33 (d, J=8.4 Hz, 1H), 8.42 (d, J=8.1 Hz, 1H), 8.46 (d, J=8.1 Hz, 1H), 8.50 (d, J=8.4 Hz, 1H), 8.64 (d, J=7.8 Hz, 1H), 8.66 (d, J=8.1 Hz, 1H); FAB-MS obsd 638.0325, calcd 638.0330 (C$_{34}$H$_{25}$Br$_2$NO$_2$); $\lambda_{abs}$ 358, 484, 512 nm; $\lambda_{em}$($\lambda_{ex}$=512 nm) 534, 575 nm.

9-(4-tert-Butylphenoxy)-N-(2,6-diisopropyl-4-bromophenyl)-3,4-perylenedicarboximide (PMI-9). A mixture of PMI-8 (409 mg, 640 µmol), 4-tert-butylphenol (384 mg, 2.56 mmol), and anhydrous K$_2$CO$_3$ (424 mg) in DMF (20 mL) was heated to reflux and stirred for 1 h. The mixture was cooled and the solvent was removed under vacuum. The crude mixture was dissolved in CHCl$_3$ and washed twice with 2 N NaOH, then with water. Column chromatography [silica, CHCl$_3$, 4×25 cm, then silica, THF/hexanes (3:2), 3×12 cm] afforded a magenta solid (367 mg, 81%): mp>300° C.; $^1$H NMR δ1.16 (d, J=6.9 Hz, 12H), 1.38 (s, 9H), 2.73 (m, 2H), 6.96 (d, J=8.4 Hz, 1H), 7.13 (d, J=8.7 Hz, 2H), 7.44 (s, 2H), 7.48 (d, J=8.7 Hz, 2H), 7.70 (t, J=8.1 Hz, 1H), 8.30 (d, J=6.6 Hz, 1H), 8.35 (d, J=8.4 Hz, 1H), 8.46 (d, J=8.4 Hz, 2H), 8.55 (d, J=7.5 Hz, 1H), 8.61 (d, J=7.8 Hz, 1H), 8.65 (d, J=8.4 Hz, 1H); FAB-MS obsd 707.2059, calcd 707.2035 (C$_{44}$H$_{38}$BrNO$_3$); $\lambda_{abs}$ 511 nm; $\lambda_{em}$ ($\lambda_{ex}$=511 nm) 569,613 nm.

9-(4-tert-Butylphenoxy)-N-[2,6-diisopropyl-4-(2-(trimethylsilyl)ethynyl)phenyl]-3,4-perylenedicarboximide (PMI-10). A mixture of PMI-9 (300 mg, 423 µmol), Pd$_2$(dba)$_3$ (38.7 mg, 42.3 µmol), P(o-tol)$_3$ (77.3 mg, 254 µmol) in toluene/triethylamine [24 mL (5:1)] was placed in an oil bath at 60° C. A sample of (trimethylsilyl)acetylene (120 µL, 0.846 mmol) was added. After 4 h, another identical batch of catalyst and (trimethylsilyl)acetylene were added. After 18 h, the mixture was cooled and passed through a silica column (CHCl$_3$). A second column [silica, toluene/hexanes (9:1)] was performed to recover a purple solid (233 mg, 76%): mp 205–208° C.; $^1$H NMR δ0.29 (s, 9H), 1.16 (d, J=6.6 Hz, 12H), 1.38 (s, 9H), 2.74 (m, 2H), 6.97 (d, J=8.4 Hz, 1H), 7.12 (d, J=9.0 Hz, 2H), 7.43 (s, 2H), 7.47 (d, J=9.0 Hz, 2H), 7.69 (t, J=8.1 Hz, 1H), 8.29 (d, J=8.4 Hz, 1H), 8.34

(d, J=8.4 Hz, 1H), 8.45 (d, J=8.4 Hz, 2H), 8.54 (d, J=7.5 Hz, 1H), 8.60 (d, J=8.1 Hz, 1H), 8.64 (d, J=8.4 Hz, 1H); $^{13}$C NMR δ0.0, 23.8, 29.1, 31.5, 34.5, 93.7, 105.6, 111.8, 119.0, 119.6, 119.7, 119.8, 120.6, 123.3, 124.0, 124.5, 124.7, 124.9, 126.4, 126.5, 126.6, 127.0, 127.9, 128.8, 128.9, 130.5, 131.8, 131.9, 132.0, 137.5, 137.6, 146.1, 147.9, 153.2, 156.9, 163.8; FAB-MS obsd 726.3389, calcd 726.3403 ($C_{49}H_{47}NO_3Si$); $\lambda_{max}$ 510 nm; $\lambda_{em}(\lambda_{ex}=510$ nm) 569, 613 nm.

9-(4-tert-Butylphenoxy)-N-(2,6-diisopropyl-4-ethynylphenyl)-3,4-perylenedicarboximide (PMI-10'). To a sample of PMI-10 (220 mg, 303 μmol) in $CH_2Cl_2$/MeOH [20 mL, (2:1)] was added a sample of $K_2CO_3$ (42 mg, 303 μmol). The mixture was stirred at room temperature for 2 h. Chloroform was added and the organic layer was washed with water. Column chromatography (silica, $CHCl_3$, 4×20 cm) afforded a magenta solid (185 mg, 93%): mp 274° C. (dec.); $^1$H NMR δ1.17 (d, J=6.9 Hz, 12H), 1.38 (s, 9H), 2.75 (m, 2H), 3.11 (s, 1H), 6.98 (d, J=8.4 Hz, 1H), 7.13 (d, J=8.4 Hz, 2H), 7.47 (s, 2H), 7.48 (d, J=8.7 Hz, 2H), 7.71 (t, J=8.1 Hz, 1H), 8.32 (d, J=8.1 Hz, 1H), 8.36 (d, J=8.7 Hz, 1H), 8.48 (dd, $J^1$=8.4 Hz, $J^2$=1.8 Hz, 2H), 8.57 (d, J=7.5 Hz, 1H), 8.62 (d, J=8.1 Hz, 1H), 8.65 (d, J=8.4 Hz, 1H); FAB-MS obsd 654.3033, calcd 654.3008 ($C_{46}H_{39}NO_3$); $\lambda_{max}$ 511 nm; $\lambda_{em}$ ($\lambda_{ex}$=511 nm) 569,613 nm.

1,6,9-Tribromo-N-(2,6-diisopropyl-4-bromophenyl)-3,4-perylenedicarboximide (PMI-11). A solution of PMI-7 (1.23 g, 2.20 mmol) in $CHCl_3$ (100 mL) was treated with $Br_2$ (2.25 mL, 44.0 mmol). The system was heated to reflux. After 3 and 5 h, identical amounts of $Br_2$ were added. After a total reaction time of 7 h, the reaction mixture was concentrated and the residue was purified by column chromatography [silica, $CHCl_3$/hexanes (3:1)], affording a red solid (1.03 g, 59%): mp>270° C.; $^1$H NMR δ1.15 (s, 6H), 1.17 (s, 6H), 2.62–2.71 (m, 2H), 7.45 (m, 2H), 7.79–7.84 (m, 1H), 8.00 (d, J=8.1 Hz, 1H), 8.46 (d, J=8.1 Hz, 1H), 8.92–8.93 (m, 2H), 9.12 (d, J=8.8 Hz, 1H), 9.33 (d, J=8.1 Hz, 1H); LD-MS (dithranol) obsd 797.74, calcd 797.17; FAB-MS obsd 796.8456, calcd 796.8426 ($C_{34}H_{23}Br_4NO_2$); $\lambda_{abs}$ 491, 517 nm; $\lambda_{em}(\lambda_{ex}$ 520 nm) 557, 598 (sh) mn 1,6,9-Tris-[9-(4-tert-Butylphenoxy)]-N-(2,6-diisopropyl-4-bromophenyl)-3,4-perylenedicarboximide (PMI-12). Samples of PMI-11 (949 mg, 1.19 mmol), 4-t-butylphenol (2.15 g, 14.3 mmol), and $K_2CO_3$ (2.37 g, 17.1 mmol) were dissolved in anhydrous DMF (80 mL) and stirred for 1 h under reflux condition. The reaction mixture was concentrated and the residue was extracted with $CHCl_3$. The organic phase was washed with 2N NaOH and water and dried over $Na_2SO_4$. Chromatography [silica, $CHCl_3$/hexanes (1:1)] afforded a magenta solid (818 mg, 68%): mp>270° C.; $^1$H NMR δ1.10 (s, 6H), 1.13 (s, 6H), 1.31 (s, 9H), 1.34 (m, 18H), 2.65–2.74 (m, 2H), 6.86 (d, J=8.8 Hz, 1H), 7.01 (d, J=8.8 Hz, 2H), 7.066 (d, J=8.8 Hz, 2H), 7.074 (d, J=8.8 Hz, 2H), 7.36 (d, J=9.5 Hz, 2H), 7.39–7.42 (m, 6H), 7.55–7.61 (m, 1H), 8.28 (s, 1H), 8.32 (s, 1H), 8.45 (d, J=8.1 Hz, 1H), 9.21 (d, J=8.8 Hz, 1H), 9.40 (d, J=7.3 Hz, 1H); $^{13}$C NMR δ24.0, 29.3, 29.9, 31.6, 34.6, 111.7, 118.3, 118.4, 120.0, 120.3, 121.3, 122.2, 123.7, 123.9, 124.5, 124.9, 125.1, 125.9, 126.7, 127.1, 127.3, 127.8, 128.0, 128.2, 130.0, 130.1, 130.3, 130.8, 131.7, 147.1, 147.2, 147.8, 148.4, 152.6, 153.4, 153.6, 156.3, 163.3; LD-MS (dithranol) obsd 1006.31 [M$^+$]; FAB-MS obsd 1003.3824, calcd 1003.3811 ($C_{64}H_{62}BrNO_5$); $\lambda_{abs}$ 411, 538 mn; $\lambda_{em}(\lambda_{ex}$=540 nm) 577, 622 (sh) mn.

1,6,9-Tris-[9-(4-tert-Butylphenoxy)]-N-[2,6-diisopropyl-4-ethynyl)phenyl]-3,4-perylenedicarboximide (PMI-12'). Samples of PMI-12 (571 mg, 0.568 mmol), (trimethylsilyl) acetylene (401 μL, 2.84 mmol), $Pd_2(dba)_3$ (52.0 mg, 56.8 μmol), and P(o-tol)$_3$ (104 mg, 341 μmol) were dissolved in toluene/triethylamine [57 mL (5:1)] and stirred at 40° C. under argon. After 3 h, another identical batch of catalyst and (trimethylsilyl)acetylene were added. After 18 h, the mixture was cooled and passed through a silica column [$CH_2Cl_2$/hexanes (3:1)]. The crude product was treated with $K_2CO_3$ in the mixture of $CHCl_3$ (25 mL) and methanol (12.5 mL) at room temperature. After 5 h, the reaction mixture was washed with water and dried over $Na_2SO_4$. Column chromatography [silica, $CH_2Cl_2$/hexanes (1:1)] afforded a magenta solid (432 mg, 80%): $^1$H NMR δ1.12 (s, 6H), 1.14 (s, 6H), 1.31 (s, 9H), 1.33 (m, 18H), 2.66–2.73 (m, 2H), 3.08 (s, 1H), 6.85 (d, J=8.8 Hz, 1H), 7.01 (d, J=8.8 Hz, 2H), 7.069 (d, J=8.8 Hz, 2H), 7.074 (d, J=8.8 Hz, 2H), 7.36 (d, J=8.8 Hz, 2H), 7.39–7.43 (m, 6H), 7.58 (m, 1H), 8.28 (s, 1H), 8.32 (s, 1H), 8.44 (d, J=8.1 Hz, 1H), 9.21 (d, J=8.8 Hz, 1H), 9.40 (d, J=7.3 Hz, 1H); $^{13}$C NMR δ24.0, 29.2, 31.7, 34.6, 84.2, 111.7, 118.3, 118.5, 120.0, 120.4, 121.4, 122.2, 123.2, 123.7, 124.5, 124.9, 125.1, 126.0, 126.7, 127.1, 127.3, 127.8, 127.9, 128.2, 130.0, 130.1, 130.8, 131.7, 132.0, 146.4, 147.1, 147.3, 147.8, 152.7, 153.5, 153.6, 156.3, 163.3; LD-MS obsd 950.17 [M$^+$]; FAB-MS obsd 949.4698, calcd 949.4706 ($C_{66}H_{63}NO_5$); $\lambda_{abs}$ 413, 536 nm; $\lambda_{em}$ ($\lambda_{ex}$=540 nm) 577, 623 (sh) nm.

9-(4-tert-Butylphenoxy)-N-(2,6-diisopropylphenyl)-3,4-perylenedicarboximide (PMI-13). A mixture of PMI-6 (151 mg, 269 μmol), 4-tert-butylphenol (161 mg, 1.07 mmol), and anhydrous $K_2CO_3$ (173 mg) in DMF (15 mL) was heated to reflux and stirred for 1 h. The mixture was cooled and the solvent was removed under vacuum. The crude mixture was dissolved in $CHCl_3$ and washed twice with 2 N NaOH, then with water. Column chromatography (silica, $CHCl_3$) afforded a magenta solid (145 mg, 86%): mp>300° C.; $^1$H NMR δ1.18 (dd, $J^1$=6.4 Hz, $J^2$=1.6 Hz, 12H), 1.38 (s, 9H), 2.78 (m, 2H), 6.95 (d, J=8.8 Hz, 1H), 7.14 (d, J=6.4 Hz, 2H), 7.34 (d, J=7.6 Hz, 2H), 7.46–7.50 (m, 3H), 7.66 (t, J=8.0 Hz, 1H), 8.26 (d, J=8.0Hz, 1H), 8.31 (d, J=8.4Hz, 1H), 8.42 (d, J=8.0 Hz, 2H), 8.50 (d, J=7.6 Hz, 1H), 8.60 (d, J=8.0 Hz, 1H), 8.64 (d, J=8.0 Hz, 1H); FAB-MS obsd 629.2937, calcd 629.2930 ($C_{44}H_{39}NO_3$); $\lambda_{abs}$ (log ϵ) 507 (4.6), 532(sh) (4.5) nm; $\lambda_{em}$ ($\lambda_{ex}$=508 nm) 567, 611 nm.

4-Bromo-2,5-di-tert-butylaniline. Bromine (271 μL, 5.29 mmol) was added dropwise via syringe to a solution of 2,5-di-tert-butylaniline (1.09 g, 5.29 mmol) in methanol (80 mL). The solution was stirred at room temperature for 10 min. Chloroform and 0.1 N NaOH were added and the organic layer was dried ($Na_2SO_4$), filtered and concentrated to a pale yellow solid (1.46 g, 97%): mp 89–90° C.; $^1$H NMR δ1.38 (s, 9H), 1.45 (s, 9H), 3.77 (brs, 2H), 6.68 (s, 1H), 7.35 (s, 1H); $^{13}$C NMR δ29.4, 29.7, 33.7, 35.8, 111.0, 117.4, 133.1, 133.8, 143.3, 145.9; FAB-MS obsd 283.0936; calcd 283.0937; Anal calcd for $C_{14}H_{22}BrN$: C, 59.16; H, 7.80; Br, 28.11; Found, C, 59.33; H, 7.78; Br, 27.86.

4-Bromo-2,6-diisopropylaniline (6). A solution of 2,6-diisopropylaniline (2.0 mL, 11 mmol) in methanol (80 mL) was treated dropwise with bromine (543 μL, 10.6 mmol). The solution was stirred at room temperature for 15 min. Chloroform and 0.1 N NaOH were added and the organic layer was dried ($Na_2SO_4$), filtered and concentrated to an orange liquid. Kugelrohr distillation (110° C. @ 0.06 Torr) afforded a colorless liquid (2.22 g 79%): $^1$H NMR (400 MHz) δ1.25 (d, J=6.4 Hz, 12H), 2.88 (m, 2H), 3.70 (brs, 2H), 7.11 (s, 2H); $^{13}$C NMR δ22.1, 27.9, 111.0, 125.6, 134.5, 139.3; Anal calcd for $C_{12}H_{19}BrN$: C, 56.26; H, 7.08; Br, 31.19; Found, C, 56.24; H, 7.07; Br, 30.98.

Zn(II)-5-[2,6-Bis[2-[4-[9-(4-tert-butylphenoxy)perylene-3,4-dicarboximido]-3,5-diisopropylphenyl]ethynyl]phenyl]-

10,15,20-trimesitylporphyrin (7). A mixture of 13' (7.0 mg, 8.2 μmol), PMI-9 (14.5 mg, 20.5 μmol), Pd$_2$(dba)$_3$ (1.9 mg, 2.1 μmol), and P(o-tol)$_3$ (3.7 mg, 12 μmol), dissolved in toluene/triethylamine [2.0 mL (10:1)] was stirred at 60° C. under argon. After 2.5 h, another identical batch of catalyst was added. After 18 h, the mixture was cooled and passed through a silica column (CHCl$_3$). Preparative SEC (toluene) followed by column chromatography [silica, CHCl$_3$/hexanes (4:1)] and trituration with hexanes afforded a red solid (4.6 mg, 27%): $^1$H NMR δ−0.16 (d, J=6.6 Hz, 24H), 1.35 (s, 18H), 1.79–1.88 (m, 22H), 2.56, 2.60 (m, 9H), 6.61 (s, 4H), 6.88 (d, J=8.1 Hz, 2H), 7.06 (d, J=8.8 Hz, 4H), 7.18 (brs, 2H), 7.23 (brs, 4H), 7.42 (d, J=8.8 Hz, 4H), 7.58–7.63 (m, 2H), 7.80–7.85 (m, 1H), 7.99 (d, J=8.1 Hz, 2H), 8.09 (d, J=8.1 Hz, 2H), 8.19–8.30 (m, 8H), 8.37 (d, J=8.1 Hz, 2H), 8.41 (d, J=8.1 Hz, 2H), 8.60 (d, J=4.4 Hz, 2H), 8.63 (d, J=4.4 Hz, 2H), 8.78 (d, J=5.1 Hz, 2H), 8.87 (d, J=4.4 Hz, 2H); LD-MS obsd 2110.42 [M$^+$] calcd avg mass 2107.93 (C$_{145}$H$_{120}$N$_6$O$_6$Zn); t$_r$ 9.70 min; λ$_{abs}$ 423, 509, 541 nm; λ$_{em}$ (λ$_{ex}$ 510 nm) 568, 600, 642 nm.

Zn(II)-5-[3,5-Bis[2-[4-[9-(4-tert-butylphenoxy)perylene-3,4-dicarboximido]-3,5-diisopropylphenyl]ethynyl]phenyl]-10,15,20-trimesitylporphyrin (8). A mixture of 17 (40.0 mg, 46.9 μmol), PMI-9 (73.0 mg, 103 μmol), Pd$_2$(dba)$_3$ (9.4 mg, 10 μmol), and P(o-tol)$_3$ (18.8 mg, 61.8 μmol) in toluene/triethylamine [5.0 mL (10:1)] was stirred at 60° C. under argon. After 3.5 h, another identical batch of catalyst was added. After 15.5 h, the mixture was cooled and passed through a silica column (CHCl$_3$). Preparative SEC (THF) and two column chromatography procedures [silica, CHCl$_3$/hexanes (9:1) and CHCl$_3$] followed by trituration with hexanes afforded a red solid (12.8 mg, 13%): $^1$H NMR δ1.18 (d, J=6.6 Hz, 24H), 1.37 (s, 18H), 1.87 (m, 18H), 2.63–2.64 (m, 9H), 2.71–2.80 (m, 4H), 6.97 (d, J=8.8 Hz, 2H), 7.12 (d, J=8.8 Hz, 4H), 7.28 (m, 2H), 7.29 (m, 4H), 7.47 (d, J=8.8 Hz, 4H), 7.53–7.58 (m, 4H), 7.67–7.72 (m, 2H), 8.24 (m, 1H), 8.30 (d, J=8.1 Hz, 2H), 8.43 (d, J=8.8 Hz, 2H), 8.42 (m, 2H), 8.456 (d, J=8.1 Hz, 2H), 8.464 (d, J=8.8 Hz, 2H), 8.55 (d, J=7.3 Hz, 2H), 8.61 (d, J=8.1 Hz, 2H), 8.65 (d, J=8.1 Hz, 2H), 8.70–8.72 (m, 4H), 8.82 (d, J=4.4 Hz, 2H), 8.95 (d, J=5.1 Hz, 2H); LD-MS (dithranol) obsd 2108.87 [M$^+$], calcd 2107.93 (C$_{145}$H$_{120}$N$_6$O$_6$Zn); λ$_{abs}$ 424, 511, 544 nm; λ$_{em}$ (λ$_{ex}$ 510 nm) 593, 644 nm.

Zn(II)-5-[3,5-Bis[2-[4-[1,6,9-tris(4-tert-butylphenoxy)perylene-3,4-dicarboximido]-3,5-diisopropylphenyl]ethynyl]phenyl]-10,15,20-trimesitylporphyrin (9). Samples of 18 (100 mg, 49.9 μmol), mesitaldehyde (22.2 mg, 150 μmol), and pyrrole (14 μL, 200 μmol) were condensed in CHCl$_3$ (2.8 mL) in the presence of BF$_3$.O(Et)$_2$ (6.2 μL, 49 μmol) at room temperature for 1.5 h. Then DDQ (34 mg, 150 μmol) was added. After 1 h, TEA was added and the crude mixture was passed through a silica column [CH$_2$Cl$_2$/hexanes (2:1)], affording a porphyrin mixture. The resulting porphyrin was treated with Zn(OAc)$_2$.2H$_2$O (55 mg, 250 μmol) in CH$_2$Cl$_2$ (10 mL) and methanol (3.0 mL) at room temperature for 12 h. The organic phase was washed with water and dried over Na$_2$SO$_4$. Preparative SEC (THF) and column chromatography [silica, CH$_2$Cl$_2$/hexanes (1:1)] afforded a red solid (24.3 mg, 18%): $^1$H NMR δ1.13 (d, J=6.6 Hz, 24H), 1.31 (s, 18H), 1.33 (s, 18H), 1.34 (s, 18H), 1.85–1.86 (m, 18H), 2.63–2.71 (m, 13H), 6.89 (d, J=8.8 Hz, 2H), 7.01 (d, J=8.8 Hz, 4H), 7.06 (d, J=8.8 Hz, 4H), 7.09 (d, J=8.8 Hz, 4H), 7.28 (m, 6H), 7.35 (d, J=8.8 Hz, 4H), 7.40 (d, J=8.1 Hz, 4H), 7.43 (d, J=8.8 Hz, 4H), 7.50 (m, 4H), 7.61–7.66 (m, 2H), 8.20 (m, 1H), 8.29 (s, 2H), 8.32 (s, 2H), 8.39 (m, 2H), 8.48 (d, J=8.1 Hz, 2H), 8.71 (d, J=4.4 Hz, 2H), 8.79 (d, J=5.1 Hz, 2H), 8.91 (d, J=4.4 Hz, 2H), 9.24 (d, J=9.5 Hz, 2H), 9.44 (d, J=8.1 Hz, 2H); LD-MS (dithranol) obsd 2694.31 [M$^+$], calcd 2700.74 (C$_{185}$H$_{168}$N$_6$O$_{10}$Zn); λ$_{abs}$ 424, 543 nm; λ$_{em}$ (λ$_{ex}$ 540 nm) 593, 644 nm.

Zn(II)-5,15-Bis[3,5-bis[2-[4-[1,6,9-tris(4-tert-butylphenoxy)perylene-3,4-dicarboximido]-3,5-diisopropylphenyl]ethynyl]phenyl]-10,20-dimesitylporphyrin (10). Samples of 16 (50.0 mg, 25.0 μmol) and 5-mesityldipyrromethane (19) (6.6 mg, 25 μmol) were condensed in CH$_2$Cl$_2$ (2.5 mL) in the presence of TFA (3.5 μL, 45 μmol) at room temperature for 30 min. Then DDQ (8.6 mg, 38 μmol) was added. After 1 h, TEA was added and the crude mixture was passed through a silica column [CH$_2$Cl$_2$/hexanes (3:1)]. The resulting porphyrin was treated with Zn(OAc)$_2$.2H$_2$O (14 mg, 63 μmol) in CH$_2$Cl$_2$ (8.0 mL) and methanol (2.0 mL) at room temperature for 12 h. The organic phase was washed with water and dried over Na$_2$SO$_4$. Column chromatography [silica, CHCl$_3$/hexanes (3:1)] followed by trituration with methanol afforded a red solid (16.1 mg, 28%): $^1$H NMR δ1.12 (d, J=6.6 Hz, 48H), 1.30 (s, 36H), 1.33 (s, 36H), 1.34 (s, 36H), 1.85 (s, 12H), 2.64–2.71 (m, 14H), 6.89 (d, J=8.8 Hz, 4H), 7.00 (d, J=8.8 Hz, 8H), 7.06 (d, J=6.6 Hz, 8H), 7.09 (d, J=6.6 Hz, 8H), 7.29 (m, 4H), 7.35 (d, J=8.8 Hz, 8H), 7.39 (d, J=6.6 Hz, 8H), 7.42 (d, J=6.6 Hz, 8H), 7.49 (m, 8H), 7.61–7.66 (m, 4H), 8.20 (m, 2H), 8.28 (s, 4H), 8.32 (s, 4H), 8.40–8.41 (m, 4H), 8.47 (d, J=8.8 Hz, 4H), 8.83 (d, J=4.4 Hz, 4H), 8.95 (d, J=5.1 Hz, 4H), 9.24 (d, J=8.8 Hz, 4H), 9.44 (d, J=8.1 Hz, 4H); LD-MS obsd [M+]; MALDI-MS (dithranol) obsd 4552.50 [M$^+$], 4402.44 [(M−4-t-Bu-Ph-O)$^+$], calcd avg mass 4555.07 (C$_{314}$H$_{284}$N$_8$O$_{20}$Zn); λ$_{abs}$ 426, 538 nm; λ$_{em}$(λ$_{ex}$ 540 nm) 596, 645 nm.

Zn(II)-meso-Tetrakis[3,5-bis[2-[4-[1,6,9-tris(4-tert-butylphenoxy)perylene-3,4-dicarboximido]-3,5-diisopropylphenyl]ethynyl]phenyl]porphyrin (11). Samples of 18 (48.0 mg, 24.0 μmol) and pyrrole (1.7 μL, 24 μmol) were condensed in CH$_2$Cl$_2$ (2.4 mL) in the presence of BF$_3$.O(Et)$_2$ [3.0 μL of a 0.81 mM stock solution of BF$_3$.O(Et)$_2$ in CH$_2$Cl$_2$ ,2.4 μmol] and NaCl (35 mg, 600 μmol) at room temperature for 1 h. Then DDQ (4.1 mg, 18 μmol) was added. After 1 h, TEA was added and the crude mixture was passed through a silica column [CHCl$_3$/acetone (49:1)] followed by preparative SEC (THF). The resulting porphyrin was treated with Zn(OAc)$_2$.2H$_2$O (6.6 mg, 30.0 μmol) in CHCl$_3$ (5.0 mL) and methanol (1.0 mL) at room temperature for 12 h. The organic phase was washed with water and dried over Na$_2$SO$_4$. Column chromatography [silica, CHCl$_3$/hexanes (4:1)] followed by trituration with methanol afforded a red solid (15.4 mg, 31%): $^1$H NMR δ; 1.11 (d, J=6.6 Hz, 96H), 1.27 (s, 72H), 1.29 (s, 72H), 1.36 (s, 72H), 2.62–2.71 (m, 16H), 6.87 (d, J=9.5 Hz, 8H), 6.98 (d, J=8.8 Hz, 16H), 7.04 (d, J=8.8 Hz, 16H), 7.07 (d, J=8.1 Hz, 16H), 7.32 (d, J=8.8 Hz, 16H), 7.36 (d, J=8.8 Hz, 16H), 7.41 (d, J=8.8 Hz, 16H), 7.51 (m, 16H), 7.58–7.63 (m, 8H), 8.23 (m, 4H), 8.27 (s, 8H), 8.30 (s, 8H), 8.43–8.46 (m, 16H), 9.11 (m, 8H), 9.22 (d, J=8.8 Hz, 8H), 9.41 (d, J=7.3 Hz, 8H); MALDI-MS (dithranol) obsd 8252.92 [M$^+$], 8104.44 [[M−(4-t-Bu-Ph-O)]$^+$], 7961.46 [[M−2×(4-t-Bu-Ph-O)]$^+$], 7483.56 [[M−5×(4-t-Bu-Ph-O)]$^+$], 7334.92 [[M−6×(4-t-Bu-Ph-O)]$^+$], calcd avg mass 8263.66 (C$_{572}$H$_{516}$N$_{12}$O$_{40}$Zn); λ$_{abs}$ 431, 505, 533 nm; λ$_{em}$ (λ$_{ex}$ 530 nm) 564(sh), 598, 648 nm.

2,6-Bis[2-(trimethylsilyl)ethynyl]benzaldehyde (12). Following the method described by Buchwald and Fu (Hundertmark, T. et al., Org. Lett. 2000, 12, 1729–1731), samples of 2,6-dichlorobenzaldehyde (3.56 g, 20.4 mmol), Pd(PhCN)$_2$Cl$_2$ (468 mg, 1.22 mmol), and CuI (155 mg, 814 μmol) were placed in a Schlenk flask. Diisopropylamine (6.7 mL), dioxane (30 mL), and P(t-Bu)$_3$ (494 mg, 2.44 mmol) were placed in a Schlenk flask and sparged of oxygen for 10 min, then added to the Schlenk flask. The flask was placed in an oil bath heated to 70° C. After 5 min, (trimethylsilyl)acetylene (7.19 mL, 50.9 mmol) was added and the mixture was stirred at 70° C. for 4 h. Removal of an aliquot and analysis by GC showed mono and di-coupled products in a nearly 1:1 ratio. An additional equivalent of (trimethylsilyl)acetylene (2.9 mL, 20.4 mmol) was added. After 24 h at 70° C., GC analysis showed no mono-coupled product. The mixture was cooled to room temperature, then filtered through a pad of silica. Kugelrohr distillation (110° C., 0.1 Torr) followed by column chromatography (silica, toluene) afforded a yellow oil (2.22 g, 37%): $^1$H NMR δ0.27 (s, 18H), 7.40–7.43 (m, 1H), 7.51 (d, J=8.0Hz, 2H), 10.63 (s, 1H); $^{13}$C NMR δ–0.0, 101.5, 102.5, 125.2, 132.3, 134.4, 137.2, 190.6; FAB-MS obsd 299.1267, calcd 299.1287; Anal Calcd. for $C_{17}H_{22}OSi_2$: C, 68.40; H, 7.43; Found: C, 67.94; H, 7.36.

Zn(II)-5-[2,6-Bis[2-(trimethylsilyl)ethynyl]phenyl]-10,15,20-trimesitylporphyrin (13). Samples of 12 (299 mg, 1.00 mmol), mesitaldehyde (445 mg, 3.00 mmol), and pyrrole (280 μL, 4.00 mmol) were condensed in CHCl$_3$ (56 mL) in the presence of BF$_3$.O(Et)$_2$ (129 μL, 1.02 mol) at room temperature for 1.5 h. Then DDQ (680 mg, 3.00 mmol) was added. After 1 h, TEA was added and the crude mixture was passed through a silica column [CHCl$_3$/hexanes (1:1)], affording a mixture of porphyrins. The resulting porphyrin mixture was treated with Zn(OAc)$_2$.2H$_2$O (550 mg, 2.50 mmol) in DMF (20 mL) overnight at 100° C. Water was added to the reaction mixture and the resulting solid was filtered. Column chromatography [silica, CH$_2$Cl$_2$/hexanes (1:1)] afforded a purple solid (10.7 mg, 1.1%): $^1$H NMR δ–1.28 (s, 18H), 1.84–1.88 (m, 18H), 2.62 (m, 9H), 7.26 (m, 6H), 7.62–7.68 (m, 1H), 7.81–7.84 (m, 2H), 8.67–8.74 (m, 8H); LD-MS obsd 996.33 [M$^+$]; FAB-MS obsd 994.3788, calcd 994.3805 ($C_{63}H_{62}N_4Si_2Zn$); $\lambda_{abs}$ 421, 548 nm; $\lambda_{em}$ ($\lambda_{ex}$ 550 nm) 593, 642 nm.

Zn(II)-5-(2,6-Diethynylphenyl)-10,15,20-trimesitylporphyrin (13'). A sample of 13 (10.0 mg, 10.0 μmol) in CHCl$_3$/THF [5.0 mL, (1:1)] was treated with TBAF on silica gel (22.0 mg, 1.0–1.5mmol/g) for 5 h at room temperature. The reaction mixture was washed with 10% NaHCO$_3$, water, and dried over Na$_2$SO$_4$. Column chromatography [silica, CHCl$_3$/hexanes (1:1)] afforded a purple solid (7.0 mg, 82%): $^1$H NMR δ1.84 (m, 18H), 2.08 (s, 2H), 2.62 (m, 9H), 7.25–7.26 (m, 6H), 7.69–7.74 (m, 1H), 7.90–7.93 (m, 2H), 8.67–8.74 (m, 8H); MALDI-MS (dithranol) obsd 852.71 [M$^+$]; FAB-MS obsd 850.3042, calcd 850.3014 ($C_{57}H_{46}N_4Zn$); $\lambda_{abs}$ 423, 550 nm; $\lambda_{em}$ ($\lambda_{ex}$ 550 nm) 595, 644 nm.

3,5-Bis[2-[4-[9-(4-tert-butylphenoxy)perylene-3,4-dicarboximido1-3,5-diisopropylphenyl]ethynyl]phenyl]benzaldehyde (15). A mixture of PMI-10' (232 mg, 355 μmol), 3,5-dibromobenzaldehyde (14) (39.0 mg, 148 μmol), Pd$_2$(dba)$_3$ (27.0 mg, 29.7 μmol), and P(o-tol)$_3$ (54.0 mg, 178 μmol) in toluene/triethylamine [25 mL (10:1)] was stirred at 60° C. under argon. After 3 h, another identical batch of catalyst was added. After 18 h, the mixture was cooled and passed through a silica column [CHCl$_3$/ethyl acetate (9:1)]. Two column chromatography procedures [silica, CHCl$_3$/ethyl acetate (95:5) and (98:2)] afforded a red solid (74.0 mg, 35%): mp>230° C.; $^1$H NMR δ1.22 (d, J=6.6 Hz, 24H), 1.38 (s, 18H), 2.74–2.81 (m, 4H), 6.99 (d, J=8.8 Hz, 2H), 7.14 (d, J=8.8 Hz, 4H), 7.48 (d, J=8.8 Hz, 4H), 7.54 (m, 4H), 7.71–7.76 (m, 8H), 8.05 (m, 3H), 8.35 (d, J=8.1 Hz, 2H), 8.39 (d, J=8.8 Hz, 2H), 8.49 (d, J=8.1 Hz, 2H), 8.51 (d, J=7.3 Hz, 2H), 8.60 (d, J=7.3 Hz, 2H), 8.65 (d, J=8.1 Hz, 2H), 8.69 (d, J=8.1 Hz, 2H), 10.07 (s, 1H); LD-MS (dithranol) obsd 1409.4 [M$^+$], calcd avg mass 1409.7 ($C_{99}H_{80}N_2O_7$); $\lambda_{abs}$ 510 nm; $\lambda_{em}$ ($\lambda_{ex}$ 510 nm) 570, 614, 671(sh) nm.

Zn(II)-5-(3,5-Diethynylphenyl)-10,15,20-trimesitylporphyrin (17). Samples of 3,5-diethynylbenzaldehyde (16) (100 mg, 0.649 mmol), mesitaldehyde (289 mg, 1.95 mmol), and pyrrole (182 μL, 2.60 mmol) were condensed in CHCl$_3$ (36 mL) in the presence of BF$_3$.O(Et)$_2$ (80 μL, 0.633 mmol) at room temperature for 1.5 h. Then DDQ (441 mg, 1.95 mmol) was added. After 1 h, TEA was added and the crude mixture was passed through a silica column [CHCl$_3$/hexanes (1:1)], affording a mixture of porphyrins. The resulting porphyrin mixture was treated with Zn(OAc)$_2$.2H$_2$O (712 mg, 3.25 mmol) in CHCl$_3$ (40 mL) and methanol (10 mL) overnight at room temperature. The organic phase was washed with water and dried over Na$_2$SO$_4$. Two column chromatography procedures [silica, CH$_2$Cl$_2$/hexanes (1:1) and (2:3)] afforded a purple solid (78.6 mg, 14%): $^1$H NMR δ1.84 (s, 12H), 1.85 (s, 6H), 2.64 (m, 9H), 3.16 (s, 2H), 7.28 (m, 6H), 8.02 (m, 1H), 8.32–8.33 (m, 2H), 8.70–8.73 (m, 4H), 8.77 (d, J=5.1 Hz, 2H), 8.80 (d, J=5.1 Hz, 2H); LD-MS obsd 852.49 [M$^+$]; FAB-MS obsd 850.3041, calcd 850.3014 ($C_{57}H_{46}N_4Zn$); $\lambda_{abs}$ 423, 549 nm; $\lambda_{em}$ ($\lambda_{ex}$ 550 nm) 593, 644 nm.

3,5-Bis[2-[4-[1,6,9-tris(4-tert-butylphenoxy)perylene-3,4-dicarboximido]-3,5-diisopropylphenyl]ethynyl]benzaldehyde, Method A (18). A mixture of PMI-12 (281 mg, 280 μmol), 3,5-diethynylbenzaldehyde (16) (22.0 mg, 140 μmol), Pd$_2$(dba)$_3$ (43.0 mg, 46.8 μmol), and P(o-tol)$_3$ (86.0 mg, 281 μmol) in toluene/triethylamine [28 mL (5:1)] was stirred at 60° C. under argon. After 3 h, another identical batch of catalyst was added. After 2 h, the mixture was cooled and passed through a silica column (CHCl$_3$). Preparative SEC (THF) and a column chromatography (silica, CHCl$_3$) afforded a magenta solid (25.0 mg, 8.9%): $^1$H NMR δ1.17 (d, J=6.6 Hz, 24H), 1.32 (s, 18H), 1.34 (s, 18H), 1.35 (s, 18H), 2.68–2.75 (m, 4H), 6.90 (d, J=8.8 Hz, 2H), 7.02 (d, J=8.8 Hz, 4H), 7.08 (d, J=8.8 Hz, 4H), 7.09 (d, J=8.1 Hz, 4H), 7.37 (d, J=8.8 Hz, 4H), 7.41 (d, J=8.8 Hz, 4H), 7.42 (d, J=8.8 Hz, 4H), 7.48 (m, 4H), 7.62–7.67 (m, 2H), 8.00 (m, 3H), 8.31 (s, 2H), 8.34 (s, 2H), 8.49 (d, J=8.8 Hz, 2H), 9.25 (d, J=8.8 Hz, 2H), 9.45 (d, J=8.1 Hz, 2H), 10.03 (s, 1H); $^{13}$C NMR δ24.1, 29.3, 29.9, 31.7, 34.6, 87.3, 92.1, 111.8, 118.4, 118.5, 120.0, 120.4, 121.4, 122.3, 123.6, 123.8, 124.5, 124.9, 125.1, 125.2, 126.0, 126.7, 127.1, 127.3, 127.4, 127.86, 127.93, 128.2, 130.0, 130.2, 130.9, 131.8, 132.06, 132.13, 136.8, 139.9, 146.6, 147.2, 147.3, 147.8, 152.7, 153.5, 153.6, 156.3, 163.4, 191.1; MALDI-MS (dithranol) obsd 2005.14, calcd avg mass 2002.51 ($C_{139}H_{128}N_2O_{11}$); $\lambda_{abs}$ 415, 537 nm; $\lambda_{em}$ ($\lambda_{ex}$ 540 nm) 579, 624(sh) nm.

3,5-Bis[2-[4-[1,6,9-tris(4-tert-butylphenoxy)perylene-3,4-dicarboximido]-3,5-diisopropylphenyl]ethynyl]benzaldehyde, Method B (18). A mixture of PMI-12' (412 mg, 434 μmol), 3,5-dibromobenzaldehyde (14) (48.0 mg, 181 μmol), Pd$_2$(dba)$_3$ (17.0 mg, 18.1 μmol), PPh$_3$ (29.0 mg, 109 μmol), and CuI (8.0 mg, 43 μmol) in toluene/triethylamine [36 mL (5:1)] was stirred at 50° C. under argon. After 3 h, another identical batch of catalyst was added. After 20 h, the mixture was cooled and passed through a silica column [CHCl$_3$/hexanes (4:1)]. Preparative SEC (THF) and a column chromatography [silica, CHCl$_3$/hexanes (9:1)] afforded a magenta solid (240 mg, 66%): Analytical data were identical to those as described above.

5-(2-Ethynylphenyl)dipyrromethane (20). Following a general procedure (Littler, B. J. et al., *J. Org. Chem.* 1999, 64, 1391–1396), a mixture of pyrrole (43 mL, 0.62 mol) and 2-ethynylbenzaldehyde (2.00 g, 15.4 mmol) was treated with TFA (0.119 mL, 1.54 mmol). The mixture was stirred at room temperature for 10 min. A solution of 0.1 M aqueous NaOH (40 mL) and ethyl acetate (40 mL) were added. The layers were separated. The aqueous layer was washed with additional ethyl acetate (50 mL). The organic layers were collected, dried ($Na_2SO_4$), and concentrated. Column chromatography [silica, $CH_2Cl_2$ followed by silica, $CH_2Cl_2$/hexanes, (3:2)] afforded a light brown solid (1.51 g, 40%): mp 95–97° C.; $^1$H NMR (400 MHz) δ3.27 (s, 1H), 5.92 (m, 2H), 6.03 (s, 1H), 6.16 (m, 2H), 6.70 (m, 2H), 7.18–7.32 (m, 3H), 7.52 (d, J=7.6 Hz, 1H), 8.03 (brs, 2H); $^{13}$C NMR δ41.6, 81.8, 81.9, 107.2, 108.4, 117.1, 121.4, 126.7, 128.2, 129.3, 131.9, 133.1, 144.8; FAB-MS obsd 246.1153, calcd 246.1157; Anal. Calcd for ($C_{17}H_{14}N_2$): C, 82.90; H, 5.73 N, 11.37. Found: C, 82.84; H, 5.75; N, 11.18.

5-(2-Ethynylphenyl)-15-mesityl-10,20-bis[4-[2-(triisopropylsilyl)ethynyl]phenyl]porphyrin (22'). Following a general procedure (Rao, P. D. et al., *J. Org. Chem.* 2000, 65, 7323–7344), a solution of diacyl dipyrromethane 21 (715 mg, 0.858 mmol) in THF/methanol [33 mL (10:1)] was reduced by portion-wise addition of $NaBH_4$ (650 mg, 17.2 mmol). After standard workup, the dipyrromethane-dicarbinol and 20 (211 mg, 0.858 mmol) were dissolved in acetonitrile/$CH_2Cl_2$ [383 mL (9:1)]. The concentration of each reactant was 2.2 mM. A sample of TFA (794 μL, 10.3 mmol, 27 mM) was added dropwise over a 30 s period. After 3 min, DDQ (584 mg, 2.57 mmol) was added. After 1 h, TEA (1 mL) was added and the entire reaction mixture was filtered through a pad of alumina using $CH_2Cl_2$ as eluent. The porphyrin-containing fractions were concentrated. Column chromatography (silica, $CH_2Cl_2$) afforded a purple solid (195 mg, 23%): $^1$H NMR (400 MHz) δ−2.70 (brs, 2H), 1.26 (s, 42H), 1.84 (m, 6H), 2.15 (s, 1H), 2.64 (s, 3H), 7.29 (s, 2H), 7.70–7.74 (m, 1H), 7.76–7.80 (m, 1H), 7.87 (d, J=7.6 Hz, 4H), 7.95 (d, J=7.2 Hz, 1H), 8.09 (d, J=7.6 Hz, 1H), 8.14 (d, J=7.2 Hz, 2H), 8.19 (d, J=7.6 Hz, 2H), 8.71 (d, J=4.4 Hz, 2H), 8.72 (d, J=5.2 Hz, 2H), 8.79 (d, J=5.2 Hz, 2H), 8.82 (d, J=4.8 Hz, 2H); LD-MS obsd 1041.0; FAB-MS obsd 1041.57, calcd 1041.57 ($C_{71}H_{76}N_4Si_2$); $λ_{abs}$ 422, 480, 515, 550, 592, 648 nm.

Zn(II)-5-(2-Ethynylphenyl)-15-mesityl-10,20-bis[4-[2-(triisopropylsilyl)ethynyl]phenyl]porphyrin (23'). To a solution of porphyrin 22' (190 mg, 182 μmol) in $CHCl_3$ (75 mL) was added a solution of $Zn(OAc)_2.2H_2O$ (400 mg, 1.82 mmol) in methanol (10 mL). After 2 h, the reaction mixture was concentrated. Column chromatography (silica, $CHCl_3$) afforded a purple solid (197 mg, 98%): $^1$H NMR δ1.26 (s, 42H), 1.79 (s, 3H), 1.88 (s, 3H), 2.10 (s, 1H), 2.64 (s, 3H), 7.28 (s, 1H), 7.30 (s, 1H), 7.71–7.79 (m, 2H), 7.86–7.89 (m, 4H), 7.94–7.96 (m, 1H), 8.13–8.17 (m, 3H), 8.21–8.24 (m, 2H), 8.80 (d, J=4.8 Hz, 2H), 8.82 (d, J=4.8 Hz, 2H), 8.89 (d, J=4.8 Hz, 2H), 8.93 (d, J=4.4 Hz, 2H); LD-MS obsd 1105.2; FAB-MS obsd 1102.47, calcd 1102.47 ($C_{71}H_{74}N_4Si_2Zn$); $λ_{abs}$ 426, 551, 590 nm; $λ_{em}$ ($λ_{ex}$ 551 nm) 598, 647 nm.

Zn(II)-5-[2-[2-[4-[9-(4-tert-Butylphenoxy)perylene-3,4-dicarboximido]-3,5-diisopropylphenyl]ethynyl]phenyl]-15-mesityl-10,20-bis[4-[2-(triisopropylsilyl)ethynyl]phenyl]porphyrin (24). A mixture of 23' (100 mg, 90.5 μmol), PMI-9 (70.0 mg, 98.8 μmol), $Pd_2(dba)_3$ (12.4 mg, 13.6 μmol), and P(o-tol)$_3$ (33.0 mg, 109 μmol) in toluene/triethylamine [36 mL (5:1)] was stirred at 60° C. for 21 h. The reaction mixture was then concentrated and passed over a silica column ($CHCl_3$). Preparative SEC (THF) followed by column chromatography [silica, $CH_2Cl_2$/hexanes (1:1)] afforded a purple solid (103 mg, 66%): $^1$H NMR δ−0.39 (d, J=6.9 Hz, 12H), 1.26 (s, 42H), 1.36 (s, 9H), 1.71 (m, 2H), 1.75 (s, 3H), 1.82 (s, 3H), 2.60 (s, 3H), 5.11 (s, 2H), 6.88 (d, J=8.1 Hz, 1H), 7.07 (d, J=8.7 Hz, 2H), 7.21 (s, 1H), 7.26 (s, 1H), 7.43 (d, J=9.0 Hz, 2H), 7.62 (t, J=7.8 Hz, 1H), 7.74–7.86 (m, 6H), 7.96 (d, J=6.6 Hz, 1H), 8.09 (d, J=8.4 Hz, 1H), 8.15–8.29 (m, 9H), 8.38–8.44 (m, 2H), 8.73 (d, J=5.1 Hz, 2H), 8.84 (d, J=4.8 Hz, 2H), 8.91 (d, J=4.8 Hz, 2H), 8.95 (d, J=4.5 Hz, 2H); LD-MS obsd 1731.0, calcd avg mass 1732.70 ($C_{115}H_{111}N_5O_3Si_2Zn$); $λ_{abs}$ 426, 510, 547, 591 nm; $λ_{em}$ ($λ_{ex}$ 510 nm) 599, 647 nm.

Zn(II)-5-[2-[2-[4-[9-(4-tert-Butylphenoxy)perylene-3,4-dicarboximido]-3,5-diisopropylphenyl]ethynyl]phenyl]-15-mesityl-10,20-bis(4-ethynylphenyl)porphyrin (24'). A sample of 24 (100 mg, 57.7 μmol) in THF (15 mL) was treated with TBAF (127 μL, 127 μmol, 1.0 M in THF) for 2 h at room temperature. The reaction mixture was concentrated and then passed through a silica column ($CHCl_3$) to afford a purple solid (49 mg, 60%): $^1$H NMR δ−0.38 (d, J=6.9 Hz, 12H), 1.35 (s, 9H), 1.72 (m, 2H), 1.75 (s, 3H), 1.80 (s, 3H), 2.59 (s, 3H), 3.29 (s, 2H), 5.15 (s, 2H), 6.88 (d, J=8.4 Hz, 1H), 7.05 (d, J=8.4 Hz, 2H), 7.20 (s, 1H), 7.26 (s, 1H), 7.42 (d, J=8.4 Hz, 2H), 7.60 (t, J=8.1 Hz, 1H), 7.72–7.87 (m, 6H), 7.96 (d, J=7.2 Hz, 1H), 8.08 (d, J=8.4 Hz, 1H), 8.16–8.27 (m, 9H), 8.36–8.42 (m, 2H), 8.37 (d, J=4.8 Hz, 2H), 8.81 (d, J=4.5 Hz, 2H), 8.90–8.94 (m, 4H); LD-MS obsd 1421.0, calcd avg mass 1420.02 ($C_{97}H_{71}N_5O_3Zn$); $λ_{abs}$ 426, 511, 546, 589 nm; $λ_{em}$ ($λ_{ex}$ 511 mn) 598, 647 nm.

5-[3,5-Bis[2-[4-[1,6,9-tris(4-tert-butylphenoxy)perylene-3,4-dicarboximido]-3,5-diisopropylphenyl]ethynyl]phenyl] dipyrromethane (25). A solution of perylene-aldehyde 18 (623 mg, 311 μmol) in pyrrole (9.0 mL, 0.13 mol) and $CH_2Cl_2$ (3.0 mL) was treated with TFA (2.4 μL, 31 μmol). The mixture was stirred at room temperature for 10 min. TEA and $CH_2Cl_2$ were added and the mixture was washed with brine. The organic layer was dried ($Na_2SO_4$) and chromatographed [silica, $CHCl_3$ $CHCl_3$/ethyl acetate (99.5:0.5)] affording a magenta solid (614 mg, 93%): $^1$H NMR δ1.15 (d, J=6.6 Hz, 24H), 1.32 (s, 18H), 1.34 (m, 36H), 2.67–2.76 (m, 4H), 5.49 (s, 1H), 5.98 (m, 2H), 6.18–6.20 (m, 2H), 6.73 (m, 2H), 6.88 (d, J=8.8 Hz, 2H), 7.02 (d, J=8.8 Hz, 4H), 7.08 (d, J=8.8 Hz, 4H), 7.09 (d, J=8.8 Hz, 4H), 7.37 (d, J=8.8 Hz, 4H), 7.40–7.45 (m, 14H), 7.59–7.64 (m, 2H), 7.70 (s, 1H), 8.01 (brs, 2H), 8.31 (s, 2H), 8.34 (s, 2H), 8.47 (d, J=8.8 Hz, 2H), 9.23 (d, J=8.8 Hz, 2H), 9.43 (d, J=8.1 Hz, 2H); $^{13}$C NMR δ24.1, 29.3, 29.9, 31.7, 34.6, 43.9, 88.5, 90.8, 107.8, 108.8, 111.8, 117.8, 118.3, 118.5, 120.0, 120.5, 121.4, 122.3, 123.7, 124.0, 124.2, 124.5, 124.8, 125.1, 126.0, 126.8, 127.1, 127.3, 127.4, 127.7, 127.9, 128.2, 130.0, 130.1, 130.9, 131.5, 131.6, 131.8, 133.7, 142.9, 146.4, 147.1, 147.3, 147.8, 152.7, 153.5, 153.6, 156.2, 163.4; MALDI-MS (dithranol) 2122.09 [M$^+$], 2056.96 [M−(pyrrole)$^+$], 1974.11 [M−(4-t-bu-Ph-O)$^+$], calcd 2118.67 ($C_{147}H_{136}N_4O_{10}$); $λ_{abs}$ 536 nm; $λ_{em}$ ($λ_{ex}$ 540 nm) 575, 623(sh) nm.

Zn(II)-5-[3,5-Bis[2-[4-[1,6,9-tris(4-tert-butylphenoxy) perylene-3,4-dicarboximido]-3,5-diisopropylphenyl] ethynyl]phenyl]-15-mesityl-10,20-bis(4-ethynylphenyl) porphyrin (27'). Following a standard procedure with improved acid catalysis conditions (Geier, G. R. III et al., *J. Porphyrins Phthalocyanines* 2001, 5, 810–823), a sample of diacyl dipyrromethane 26' (46.0 mg, 99.1 μmol) was reduced with $NaBH_4$ (74.0 mg, 1.98 mmol) in THF/methanol [5.0 mL (10:1)]. The resulting dipyrromethane-dicarbinol was condensed with perylene-dipyrromethane 25 (210 mg, 99.1 μmol) in $CH_2Cl_2$ (40 mL) containing $Yb(OTf)_3$ (79.0 mg, 128 μmol, 3.2 mM) for 15 min. DDQ (68.0 mg, 300 μmol) was added and the mixture was stirred at room temperature for 1 h. The mixture was neutralized with TEA then filtered through a silica column [$CH_2Cl_2$/hexanes (2:1)]. The residue was treated with Zn(OAc)$_2$·2H$_2$O (110 mg, 500 μmol) in CHCl$_3$ (20 mL) and methanol (5.0 mL) at room temperature for 2 h. The mixture was washed with water. The organic phase was dried (Na$_2$SO$_4$) and chromatographed [silica, $CH_2Cl_2$/hexanes (2:1)]. The product was concentrated, then triturated with hexanes affording a red solid (95.5 mg, 36%): $^1$H NMR δ1.13 (d, J=6.6 Hz, 24H), 1.30 (s, 18H), 1.33 (s, 18H), 1.34 (s, 18H), 1.84 (s, 6H), 2.64–2.74 (m, 7H), 3.31 (s, 2H), 6.89 (d, J=8.8 Hz, 2H), 7.01 (d, J=8.8 Hz, 4H), 7.06 (d, J=8.8 Hz, 4H), 7.08 (d, J=8.8 Hz, 4H), 7.29 (m, 2H), 7.35 (d, J=8.8 Hz, 4H), 7.40 (d, J=8.8 Hz, 4H), 7.42 (d, J=8.8 Hz, 4H), 7.50 (m, 4H), 7.61–7.66 (m, 2H), 7.89 (d, J=8.1 Hz, 4H), 8.19–8.22 (m, 5H), 8.29 (s, 2H), 8.32 (s, 2H), 8.39 (m, 2H), 8.48 (d, J=8.1 Hz, 2H), 8.82 (d, J=4.4 Hz, 2H), 8.89 (d, J=5.1 Hz, 2H), 8.96 (d, J=5.1 Hz, 2H), 9.03 (d, J=5.1 Hz, 2H), 9.24 (d, J=8.8 Hz, 2H), 9.44 (d, J=8.1 Hz, 2H); MALDI-MS (dithranol) 2664.25 [M$^+$], 2517.33 [M–(4-t-bu-Ph-O)$^+$], 1900.24 [M–(perylene)$^+$], calcd 2664.62 ($C_{183}H_{156}N_6O_{10}Zn$); λ$_{abs}$ 427, 541 nm; λ$_{em}$ (λ$_{ex}$ 540 nm) 599, 647 nm.

1-(4-Ethynylbenzoyl)-9-(4-iodobenzoyl)-5-mesityldipyrromethane (28'). A sample of 28 (300 mg, 0.432 mmol) in CHCl$_3$ (10 mL) was treated with TBAF on silica (648 mg, 1.0–1.5 mmol F$^-$/g resin) at room temperature for 1 h. The mixture was washed with 10% NaHCO$_3$. The organic phase was washed with water, dried (Na$_2$SO4), and concentrated. Column chromatography [silica, $CH_2Cl_2$/ethyl acetate (95:5)] afforded a brown solid (262 mg, 97%): mp>106–108° C.; $^1$H NMR δ2.24 (s, 6H), 2.32 (s, 3H), 3.18 (s, 1H), 5.95 (m, 2H), 6.21 (s, 1H), 6.56–6.60 (m, 2H), 6.93 (s, 2H), 7.40 (d, J=8.1 Hz, 2H), 7.48 (d, J=8.1 Hz, 2H), 7.64 (d, J=8.1 Hz, 2H), 7.72 (d, J=8.1 Hz, 2H), 11.40 (m, 2H); $^{13}$C NMR δ21.0, 39.4, 79.7, 83.2, 99.1, 110.9, 121.3, 121.4, 125.5, 129.4, 130.2, 130.3, 130.5, 131.0, 131.9, 133.1, 137.3, 137.4, 137.6, 138.3, 140.6, 140.7, 182.9; HRMS (FAB) obsd 623.1186, calcd 623.1196 ($C_{34}H_{27}IN_{22}$).

Zn(II)-5-[3,5-Bis[2-[4-[1,6,9-tris(4-tert-butylphenoxy)perylene-3,4-dicarboximido]-3,5-diisopropylphenyl]ethynyl]phenyl]-10-(4-iodophenyl)-15-mesityl-20-(4-ethynylphenyl)porphyrin (29'). Following a known procedure with improved acid catalysis conditions (Geier, G. R. III et al., *J. Porphyrins Phthalocyanines* 2001, 5, 810–823), a sample of diacyl dipyrromethane 28 (26 mg, 41 μmol) was reduced with NaBH$_4$ (30 mg, 0.82 mmol) in THF/methanol [5.0 mL, (10:1)]. The resulting dipyrromethane-dicarbinol was condensed with perylene-dipyrromethane 25 (86 mg, 41 μmol) in $CH_2Cl_2$ (16 mL) containing Yb(OTf)$_3$ (32 mg, 51 μmol, 3.2 mM) for 20 min. DDQ (28 mg, 120 μmol) was added and the mixture was stirred at room temperature for 1 h. The mixture was neutralized with TEA then filtered through a silica column [$CH_2Cl_2$/hexanes (2:1)]. The residue was treated with Zn(OAc)$_2$·2H$_2$O (46 mg, 210 μmol) in $CH_2Cl_2$ (10 mL) and methanol (3.0 mL) at room temperature for 15 h. The mixture was passed through a silica gel column [$CH_2Cl_2$/hexanes (2:1)] followed by trituration with methanol to afford a red solid (33.5 mg, 30%): $^1$H NMR δ1.13 (d, J=6.6 Hz, 24H), 1.30 (s, 18H), 1.33 (s, 18H), 1.34 (s, 18H), 1.83 (s, 6H), 2.64–2.72 (m, 7H), 3.31 (s, 1H), 6.89 (d, J=8.8 Hz, 2H), 7.01 (d, J=8.8 Hz, 4H), 7.06 (d, J=8.8 Hz, 4H), 7.08 (d, J=8.8 Hz, 4H), 7.29 (m, 2H), 7.35 (d, J=8.8 Hz, 4H), 7.40 (d, J=8.1 Hz, 4H), 7.41 (d, J=8.1 Hz, 4H), 7.50 (m, 4H), 7.60–7.66 (m, 2H), 7.89 (d, J=8.1 Hz, 2H), 7.97 (d, J=8.1 Hz, 2H), 8.10 (d, J=8.8 Hz, 2H), 8.19–8.23 (m, 3H), 8.29 (s, 2H), 8.32 (s, 2H), 8.39 (m, 2H), 8.47 (d, J=8.1 Hz, 2H), 8.81 (d, J=4.4 Hz, 2H), 8.88–8.90 (m, 2H), 8.96 (d, J=5.1 Hz, 2H), 9.03 (d, J=5.1 Hz, 2H), 9.24 (d, J=8.8 Hz, 2H), 9.44 (d, J=8.1 Hz, 2H); MALDI-MS (dithranol) 2760.44 [M$^+$], 2634.37 [M–(I)$^+$], calcd 2766.50 ($C_{181}H_{155}IN_6O_{10}Zn$); λ$_{abs}$ 427, 542 nm; λ$_{em}$ (λ$_{ex}$ 540 nm) 598, 647 nm.

Zn(II)-5,15-Bis[3,5-bis[2-[4-[1,6,9-tris(4-tert-butylphenoxy)perylene-3,4-dicarboximido]-3,5-diisopropylphenyl]ethynyl]phenyl]-10,20-bis(4-ethynylphenyl)porphyrin (31'). Following a known procedure (Littler, B. J. et al., *J. Org. Chem.* 1999, 64, 2864–2872), samples of 4-ethynylbenzaldehyde, 30 (6.1 mg, 47 μmol) and perylene-dipyrromethane 25 (100 mg, 47 μmol) were condensed in $CH_2Cl_2$ (4.7 mL) containing TFA (6.5 μL, 84 μmol) at room temperature for 1 h. Then DDQ (16 mg, 71 μmol) was added. After 1 h, TEA was added and the crude mixture was passed through a silica column [$CH_2Cl_2$/hexanes (2:1)], followed by preparative SEC (THF). The residue was treated with Zn(OAc)$_2$·2H$_2$O (53 mg, 240 μmol) in $CH_2Cl_2$ (8.0 mL) and methanol (2.0 mL) at room temperature for 15 h. The organic phase was washed with water, dried over Na$_2$SO$_4$, and concentrated. The mixture was washed with water and dried (Na$_2$SO$_4$). Column chromatography [silica, $CH_2Cl_2$/hexanes (2:1)] followed by trituration with methanol afforded a red solid (24.1 mg, 23%): $^1$H NMR δ1.13 (d, J=6.6 Hz, 48H), 1.30 (s, 36H), 1.33 (s, 36H), 1.34 (s, 36H), 2.65–2.74 (m, 8H), 3.32 (s, 2H), 6.88 (d, J=8.8 Hz, 4H), 7.01 (d, J=8.8 Hz, 8H), 7.07 (d, J=8.1 Hz, 8H), 7.08 (d, J=8.8 Hz, 8H), 7.35 (d, J=8.8 Hz, 8H), 7.40 (d, J=8.8 Hz, 8H), 7.42 (d, J=8.8 Hz, 8H), 7.50 (m, 8H), 7.60–7.66 (m, 4H), 7.91 (d, J=8.1 Hz, 4H), 8.20–8.23 (m, 6H), 8.29 (s, 4H), 8.32 (s, 4H), 8.40–8.41 (m, 4H), 8.47 (d, J=8.8 Hz, 4H), 9.00 (d, J=4.4 Hz, 4H), 9.06 (d, J=4.4 Hz, 4H), 9.24 (d, J=8.8 Hz, 4H), 9.44 (d, J=7.3 Hz, 4H); MALDI-MS (dithranol) obsd 4515.17 [M$^+$], 4390.09 [M–(4-t-Bu-Ph-O)$^+$], 3756.60 [M–(perylene)$^+$], calcd 4518.93 ($C_{312}H_{272}N_8O_{20}Zn$); λ$_{abs}$ 429, 539 nm; λ$_{em}$ (λ$_{ex}$ 540 nm) 600, 649 nm.

Zn(II)-5,15-Bis[3,5-bis[2-[4-[1,6,9-tris(4-tert-butylphenoxy)perylene-3,4-dicarboximido]-3,5-diisopropylphenyl]ethynyl]phenyl]porphyrin (33). Following a general procedure (Littler, B. J. et al., *J. Org. Chem.* 1999, 64, 2864–2872), samples of dipyrromethane 32 (14.6 mg, 99.9 μmol) and perylene-aldehyde 18 (200 mg, 99.9 μmol) in $CH_2Cl_2$ (10 mL) were condensed in the presence of TFA (13.7 μL, 178 μmol) at room temperature for 30 min. DDQ (34.0 mg, 150 μmol) was then added. After 1 h, the reaction mixture was passed through a silica column [$CH_2Cl_2$/hexanes (4:1)]. The crude free base porphyrin was dissolved in CHCl$_3$ and treated with Zn(OAc)$_2$·2H$_2$O (54.8 mg, 250 μmol) in MeOH (2 mL) at room temperature for 12 h. The reaction mixture was passed through a silica column (CHCl$_3$) to afford a magenta solid (93.6 mg, 43%): $^1$H NMR δ1.14 (d, J=6.4 Hz, 48H), 1.30 (s, 36H), 1.33 (s, 36H), 1.34 (s, 36H), 2.70 (m, 8H), 6.88 (d, J=9.2 Hz, 4H), 7.00 (d, J=8.4 Hz, 8H), 7.05–7.10 (m, 16H), 7.35 (d, J=8.4 Hz, 8H), 7.38–7.42 (m, 16H), 7.52 (s, 8H), 7.63 (t, J=8.4 Hz, 4H), 8.26–8.32 (m, 10H), 8.46–8.48 (m, 8H), 9.23 (d, J=4.8 Hz, 4H), 9.25 (s, 4H), 9.43 (d, J=7.6 Hz, 4H), 9.54 (d, J=4.4 Hz, 4H), 10.41 (s, 2H), LD-MS obsd 4308.53, calcd avg mass 4318.70 ($C_{296}H_{264}N_8O_{20}Zn$); λ$_{abs}$ 418, 539 nm.

Zn(II)-5,15-Bis[3,5-bis[2-[4-[1,6,9-tris(4-tert-butylphenoxy)perylene-3,4-dicarboximido]-3,5-diisopropylphenyl]ethynyl]phenyl]-10,20-dibromoporphyrin (34). Following a standard procedure, a sample of porphyrin 33 (93.0 mg, 21.6 μmol) was dissolved CHCl$_3$ (5.5 mL) and cooled to 0° C. Pyridine (12 μL) was added followed by NBS (7.7 mg, 43.2 μmol, recrystallized from H$_2$O). The reaction mixture was stirred at 0° C. for 30 min, warmed to room temperature, then passed through a silica column [$CH_2Cl_2$/hexanes (4:1)]. The resulting magenta solid was triturated with methanol, then hexanes to recover a magenta solid (69.4 mg, 72%): $^1$H NMR δ1.14 (d, J=6.4 Hz, 48H), 1.31 (s, 36H), 1.33 (s, 36H), 1.34 (s, 36H), 2.71 (m, 8H), 6.88 (d, J=9.2 Hz, 4H), 7.00 (d, J=8.4 Hz, 8H), 7.06–7.10 (m, 16H), 7.36 (d, J=8.4 Hz, 8H), 7.39–7.43 (m, 16H), 7.52 (s, 8H), 7.63 (t, J=8.4 Hz, 4H), 8.25–8.35 (m, 10H), 8.46–8.48 (d, J=8.0 Hz, 8H), 9.05 (d, J=4.8 Hz, 4H), 9.24 (s, 4H), 9.43 (d, J=7.6 Hz, 4H), 9.81 (d, J=4.4 Hz, 4H); LD-MS obsd 4467.11, calcd avg mass 4476.49 ($C_{296}H_{262}Br_2N_8O_{20}Zn$); $\lambda_{abs}$ 435, 537, 598 nm.

1,4-Bis(4,4,5,5-tetramethyl-1,3,2-dioxaborolan-2-yl)benzene (35). Following a standard procedure (Nicolas, M. et al., *Eur. J. Org. Chem.* 2000, 1703–1710; Ishiyama, T. et al., *Tetrahedron Lett.* 1997, 38, 3447–3450; Yu, L. and Lindsey, J. S. *Tetrahedron* 2001, 57, 9285–9298) for forming dioxaborolanes but with use of DMF instead of ether to achieve solubility of the bis(boronic acid), samples of 1,4-bis(dihydroxyboryl)benzene (5.158 g, 31.1 mmol) and pinacol (8.83 g, 74.7 mmol) were dissolved in anhydrous DMF (100 mL). The reaction mixture was stirred for 12 h at room temperature, affording a white solid. Water (100 mL) was added and the reaction mixture was filtered. The resulting white solid was dried (9.23 g, 93%). Physical data for this compound are identical to the literature (Shultz, D. A. et al., *J. Org. Chem.* 1999, 64, 9124–9136).

Synthesis of Polymers.

Poly-24'. Samples of 24' (8.0 mg, 5.6 μmol), Pd(PPh$_3$)$_2$Cl$_2$ (0.50 mg, 0.75 μmol), CuI (70 μg, 0.361mol), and I$_2$ (1.4 mg, 5.6 μmol) were dissolved in toluene/DIEA [2.2 mL, (5:1)]. The reaction mixture was stirred under an air atmosphere at room temperature overnight. Analysis by SEC showed very little starting monomer with most of the material exhibiting significantly higher molecular weight. The solvent was removed yielding a film that was intractable; therefore, further analysis was not attempted.

Poly-27'. A solution of 27' (20 mg, 7.5 μmol) in toluene/DIEA [3.0 mL, (5:1)] was treated with Pd(PPh$_3$)$_2$Cl$_2$ (1.0 mg, 1.5 μmol), CuI (0.3 mg, 2 μmol) and I$_2$ (1.9 mg, 7.5 μmol). The mixture was stirred at room temperature for 2 h. THF was added (8 mL) and the mixture was passed over a preparative SEC column (THF). The leading band was collected and concentrated. The resulting material was passed over a silica column (CHCl$_3$). The major band was concentrated and the resulting solid was washed with methanol and then hexanes. The sample was dried yielding a magenta film (11.1 mg, 56%): $^1$H NMR δ1.29 (s, 18H), 1.32 (s, 18H), 1.34 (s, 18H), 1.78 (m, 6H), 2.62–2.75 (m, 7H), 6.9 (d, 2H), 7.00–7.09 (m, 12H), 7.34–7.43 (m 14H), 7.62 (t, 2H), 8.0 (brs, 4H), 8.23–8.33 (m, 9H), 8.44–8.49 (m, 4H), 8.86 (brs, 2H), 8.88 (brs, 2H), 9.04 (brs, 2H), 9.08 (brs, 2H), 9.24 (d, 2H), 9.45 (d, 2H); $\lambda_{abs}$ 430, 438, 547, 598 nm; $\lambda_{em}$ ($\lambda_{ex}$ =500 nm) 609, 654 nm.

Poly-29'. A mixture of 29' (20 mg, 7.2 μmol), Pd$_2$(dba)$_3$ (1.0 mg, 1.1 μmol), and Ph$_3$As (2.7 mg, 8.7 μmol) in toluene/TEA [3.0 mL, (5:1)] was stirred under Ar at room temperature. Aliquots were removed and analyzed by SEC after 2 h, 5 h, and 22 h. The reaction was stopped after 23 h. The reaction mixture was concentrated to near dryness. THF was added and the reaction mixture was passed through a preparative SEC column (THF). The leading band was collected and concentrated. The resulting solid was triturated with methanol, then hexanes yielding a magenta solid (16.8 mg, 88%).

Poly-31'. Samples of 31' (25 mg, 5.5 μmol), Pd(PPh$_3$)$_2$Cl$_2$ (0.77 mg, 1.1 μmol), CuI (0.21 mg, 1.1 μmol) were dissolved in toluene/DIEA [2.2 mL, (9:1)]. The mixture was stirred under an air atmosphere at room temperature for 30 min. The reaction mixture was not homogeneous. However, addition of THF caused most of the precipitate to redissolve. The crude mixture was passed through a preparative SEC column (THF). The leading band was collected, concentrated, then triturated with methanol followed by hexanes to yield a magenta solid (21.8 mg, 88%).

Poly-34. Samples of 34 (40 mg, 4.5 μmol), compound 35, (2.9 mg, 4.5 μmol), Pd(PPh$_3$)$_4$ (3.1 mg, 1.3 μmol), K$_2$CO$_3$ (9.8 mg, 36 μmol) were dissolved in toluene/DMF [900 μL, (2:1)]. The reaction mixture was placed into an oil bath heated to 90° C. and stirred under Ar. Aliquots were removed at 2, 6, 22, and 36 h for analysis by analytical SEC. Oligomers of length 2–5 were obtained but at no timepoint were longer oligomers observed.

TABLE 1

Conditions for Sonogashira Reaction Yielding Bis(perylene)aldehyde 18.[a]

| Entry | Copper source | Ligand | Temp. | Reactants (mM) | | Yield |
|---|---|---|---|---|---|---|
| 1 | None | P(o-tol)$_3$ | 60° C. | PMI-12 (10) | 16 (5) | 8.9% |
| 2 | CuI | PPh$_3$ | 50° C. | PMI-12 (10) | 16 (5) | 0% |
| 3 | CuI | PPh$_3$ | 50° C. | PMI-12' (10) | 14 (5) | 31% |
| 4 | CuI | PPh$_3$ | 50° C. | PMI-12' (12) | 14 (5) | 66–83% |

[a]Toluene/TEA (5:1) as solvent; Pd$_2$(dba)$_3$ as palladium source for all entries.

TABLE 2

Absorption and Fluorescence Properties of Perylene Benchmark Dyes.

| Compound | $\lambda_{abs}$ (log ε) | fwhm (nm) | $\lambda_{em}$ (nm) | $\Phi_f$ | τ (ns) |
|---|---|---|---|---|---|
| PMI-2 | 479 (4.5), 506 (4.5)[a] | 75 | 529, 569, 614(sh) | 0.91[b] | 5.0[c] |
| PMI-13 | 507 (4.6) | 82 | 567, 611 | 0.82 | 4.8 |
| PMI-12' | 536 (4.6) | 71 | 577, 623(sh) | 0.86 | 5.0 |

[a]Value from literature (Boehm, A.; Helfer, W. U.S. Pat. No. 5,808,073) = 484 (4.5), 506 (4.5).
[b]Value from literature (Hofkens, J. et al., Chem. Phys. Lett. 1999, 304, 1–9) = 0.90.
[c]Value from literature (Hofkens, J. et al., Chem. Phys. Lett. 1999, 304, 1–9) = 4.6 ns.

TABLE 3

Absorption and Fluorescence Properties of Perylene-Porphyrin Arrays.

| Compd | Number of perylene pigments | $\lambda_{max}$ (nm) | $\epsilon_{perylene}/\epsilon_{Soret}$ (%)[a] | $\Phi_f$[b] toluene | benzonitrile |
|---|---|---|---|---|---|
| 7 | 2 | 423, 509, 541 | 16 | 0.028 | 0.013 |
| 8 | 2 | 424, 511, 544 | 15 | 0.036 | 0.045 |
| 9 | 2 | 424, 543 | 16 | 0.036 | 0.047 |
| 10 | 4 | 426, 538 | 40 | 0.044 | 0.070 |
| 11 | 8 | 431, 533 | 73 | 0.050 | 0.050 |

[a]$\epsilon_{perylene} = \epsilon_{max}$ from 509 to 538 nm.
[b]Fluorescence emission yields were determined upon excitation (423 nm) of solutions in toluene at room temperature. Yields were determined by ratioing to that of ZnTPP ($\Phi_f$ = 0.033) in toluene.

TABLE 4

Förster Energy-Transfer Parameters.

| Donor | Model Cmpd(s) | Site of Attachment | Actual Distance (Å)[a] | J (cm⁶/mmol)[b] | $R_o$ (Å) | Calculated Efficiency (%) |
|---|---|---|---|---|---|---|
| PMI-13 | 7 | o- | 11.1 | 5.1 × 10⁻¹⁴ | 44.2 | 99.98 |
| PMI-13 | 8 | m- | 17.5 | 4.5 × 10⁻¹⁴ | 43.6 | 99.6 |
| PMI-12' | 9–11 | m- | 17.5 | 4.5 × 10⁻¹⁴ | 43.6 | 99.6 |

[a]Determined by molecular modeling.
[b]Based on the emission spectrum of the donor and the absorption spectrum of ZnTPP.

TABLE 5

Characteristics of polymers produced from perylene-porphyrin building blocks.

| Entry | Number of Perylenes | No. of ArO— Groups | Site of Attachment | Monomer | Polymerization Type | Linker |
|---|---|---|---|---|---|---|
| 1 | 1 | 1 | 2- | 24' | Glaser | 4,4' diphenyl-butadiyne |
| 2 | 2 | 3 | 3,5- | 27' | Glaser | 4,4' diphenyl-butadiyne |
| 3 | 2 | 3 | 3,5 | 29' | Sonogashira | 4,4' diphenyl-ethyne |
| 4 | 4 | 3 | 3,5 | 31' | Glaser | 4,4' diphenyl-butadiyne |
| 5 | 4 | 3 | 3,5 | 34 | Suzuki | 1,4-phenylene |

TABLE 6

Solubility of polymers produced from perylene-porphyrin building blocks.

| | Polymer Solubility at 2.5 mM[a] | | | |
|---|---|---|---|---|
| Solvent | Poly-24' | Poly-27' | Poly-29' | Poly-31' |
| toluene | — | + | ± | |
| THF | — | + | ± | + |
| CHCl₃ | — | + | ± | + |
| benzonitrile | — | ± | ± | |

[a]A known volume of solvent was added to a known mass of polymer. Full dissolution of the polymer resulted in a 2.5 mM concentration. "+" = soluble at 2.5 mM; "+" = partially soluble (less than 2.5 mM); "−" = not soluble.

The foregoing is illustrative of the present invention, and is not to be construed as limiting thereof. The invention is defined by the following claims, with equivalents of the claims to be included therein.

That which is claimed is:

1. A light harvesting array, comprising:
    (a) a first substrate comprising a first electrode; and
    (b) a layer of light harvesting rods electrically coupled to said first electrode, each of said light harvesting rods comprising a polymer of Formula I:

(I)

wherein:
   m is at least 1;
   $X^1$ is a charge separation group having an excited-state of energy equal to or lower than that of $X^2$;
   $X^2$ through $X^{m+1}$ are chomophores; and
   at least one of $X^2$ through $X^{m+1}$ has at least one perylene group coupled thereto, and wherein said perylene group is a perylene (bis)imide group.

2. A light harvesting array according to claim 1, wherein m is from 2 to 49.

3. A light harvesting array according to claim 1, wherein at least one of $X^2$ through $X^{m+1}$ has at least two perylene groups coupled thereto.

4. A light harvesting array according to claim 1, wherein at least one of $X^2$ through $X^{m+1}$ further has at least one of a perylene group coupled thereto at a perylene N-imide position.

5. A light harvesting array according to claim 1, wherein at least one of $X^2$ through $X^{m+1}$ further has at least one of a perylene group coupled thereto at a perylene 1, 6, 9, or 11 position.

6. A light harvesting array according to claim 1, wherein:
    m is from 2 to 49;
    at least one of $X^2$ through $X^{m+1}$ further has at least two perylene groups coupled thereto;
    said perylene groups are perylene mono-imides; and
    said perylene groups are coupled thereto at the perylene 1, 6, 9, 11, or N-imide positions.

7. A light harvesting array according to claim 1, wherein at least one of $X^1$ through $X^{m+1}$ is selected from the group consisting of chlorins, bacteriochlorins, and isobacteriochlorins.

8. A light harvesting array according to claim 1, wherein $X^1$ through $X^{m+1}$ are selected so that, upon injection of either an electron or hole from $X^1$ into said first electrode, the corresponding hole or electron from $X^1$ is transferred to at least $X^2$.

9. A light harvesting array according to claim 1, wherein $X^1$ comprises a porphyrinic macrocycle.

10. A light harvesting array according to claim 1, wherein $X^1$ comprises a double-decker sandwich coordination compound.

11. A light harvesting array according to claim 1, wherein $X^2$ through $X^{m+1}$ comprise porphyrinic macrocycles.

12. A light-harvesting array according to claim 1, wherein $X^1$ through $X^{m+1}$ comprise porphyrinic macrocycles.

13. A light harvesting array according to claim 1, wherein at least one of $X^2$ through $X^{m+1}$ comprises a meso-linked porphyrinic macrocycle.

14. A light harvesting array according to claim 1, wherein at least one of $X^2$ through $X^{m+1}$ comprises a trans meso-linked porphyrinic macrocycle.

15. A light harvesting array according to claim 1, wherein $X^2$ through $X^{m+1}$ consist of meso-linked porphyrinic macrocycles.

16. A light harvesting array according to claim 1, wherein $X^2$ through $X^{m+1}$ consist of trans meso-linked porphyrinic macrocycles.

17. A light harvesting array according to claim 1, wherein at least one of $X^2$ through $X^{m+1}$ comprises a β-linked porphyrinic macrocycle.

18. A light harvesting array according to claim 1, wherein at least one of $X^2$ through $X^{m+1}$ comprises a trans β-linked porphyrinic macrocycle.

19. A light harvesting array according to claim 1, wherein $X^2$ through $X^{m+1}$ consist of β-linked porphyrinic macrocycles.

20. A light harvesting array according to claim 1, wherein $X^2$ through $X^{m+1}$ consist of trans β-linked porphyrinic macrocycles.

21. A light harvesting array according to claim 1, wherein said light harvesting rods are oriented substantially perpendicularly to said first electrode.

22. A light harvesting array according to claim 1, wherein said substrate is rigid.

23. A light harvesting array according to claim 1, wherein said substrate is flexible.

24. A light harvesting array according to claim 1, wherein said substrate is transparent.

25. A light harvesting array according to claim 1, wherein said substrate is opaque.

26. A light harvesting array according to claim 1, wherein said substrate is reflective.

27. A light harvesting array according to claim 1, wherein said substrate is substantially planar in shape.

28. A light harvesting array according to claim 1, wherein said electrode comprises a metallic conductor.

29. A light harvesting array according to claim 1, wherein said electrode comprises a nonmetallic conductor.

30. A light harvesting array according to claim 1, wherein said light-harvesting rods are intrinsic rectifiers of excited-state energy.

31. A light harvesting array according to claim 1, wherein said light harvesting rods are intrinsic rectifiers of holes.

32. A light harvesting array according to claim 1, wherein said light harvesting rods are not greater than 500 nanometers in length.

33. A solar cell, comprising:
(a) a light harvesting array according to claim 1;
(b) a second substrate comprising a second electrode, with said first and second substrate being positioned to form a space therebetween, and with at least one of (i) said first substrate and said first electrode and (ii) said second substrate and said second electrode being transparent; and
(c) an electrolyte in said space between said first and second substrates.

34. A solar cell according to claim 33, further comprising a mobile charge carrier in said electrolyte.

35. A solar cell according to claim 33, wherein said electrolyte comprises an aqueous electrolyte.

36. A solar cell according to claim 33, wherein said electrolyte comprises a non-aqueous electrolyte.

37. A solar cell according to claim 33, wherein said electrolyte comprises a polymer electrolyte.

38. A solar cell according to claim 33, wherein said electrolyte comprises a solid.

39. A solar cell according to claim 33, wherein said solar cell is devoid of liquid in said space between said first and second substrates.

40. A solar cell according to claim 33, wherein $X^1$ is electrically coupled to said first electrode.

41. A solar cell according to claim 33, wherein $X^{m+1}$ is electrically coupled to said second electrode.

42. An electrical device, comprising:
(a) a solar cell according to claim 33; and
(b) a circuit electrically coupled to said solar cell.

43. An electrical device according to 42, claim wherein said circuit comprises a resistive load.

44. A composition useful for the manufacture of a light harvesting array, comprising:
(a) a non-polar organic solvent; and
(b) from 2 microMolar to 100 milliMolar of light harvesting rods solubilized in said organic solvent, said light harvesting rods comprising a polymer of Formula I:

$$X^1\text{-}(X^{m+1})_m \qquad (I)$$

wherein:
m is at least 1;
$X^1$ is a charge separation group having an excited-state of energy equal to or lower than that of $X^2$;
$X^2$ through $X^{m+1}$ are chromophores; and
at least one of $X^2$ through $X^{m+1}$ has at least one perylene group coupled thereto;
wherein said perylene group is a compound of formula IV:

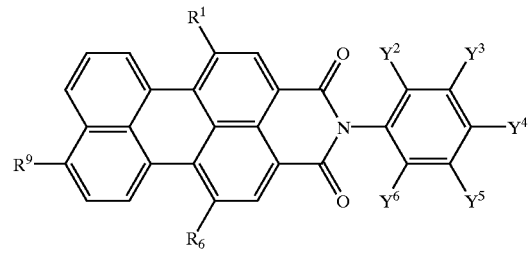

formula IV wherein:
$R^9$ is a link to one of said chromophores;
$R^1$ and $R^6$ are independently selected from the group consisting of H, alkyl, aryl, alkoxy, aryloxy, alkylthio, arylthio, halo, ethynylalkyl, ethynylaryl, dialkylboronate and trialkyltin;
$Y^2$ through $Y^6$ are independently selected from the group consisting of H, alkyl, aryl, alkoxy, aryloxy, alkylthio, arylthio, halo, ethynylalkyl, ethynylaryl, dialkylboronate, and trialkyltin; and
wherein either (i) $Y^4$ is halo, ethynyl, dialkylboronate, or trialkyltin, or (ii) $Y^3$ is halo, ethynyl, dialkylboronate, or trialkyltin.

45. A composition according to claim 44, wherein said solvent is selected from the group consisting of tetrahydrofuran, toluene, chloroform, chlorobenzene, xylene, dichloromethane, mesitylene, 1,1,1-trichloroethane, 2-chloronaphthalene, 1,2-dichlorobenzene, 1,1,2,2-tetrachloroethane, and mixtures thereof.

46. A composition according to claim 44, wherein m is from 2 to 49.

47. A composition according to claim 44, wherein at least one of $X^2$ through $X^{m+1}$ has at least two perylene groups coupled thereto.

48. A composition according to claim 44, wherein at least one of $X^2$ through $X^{m+1}$ further has at least one of a perylene group coupled thereto at a perylene N-imide position.

49. A composition according to claim 44, wherein at least one of $X^2$ through $X^{m+1}$ further has at least one of a perylene group coupled thereto at a perylene 1, 6, 9, or 11 position.

50. A composition according to claim 44, wherein:
m is from 2 to 49;
at least one of $X^2$ through $X^{m+1}$ further has at least two perylene groups coupled thereto;
said perylene groups are perylene mono-imides; and
said perylene groups are coupled thereto at the perylene 1, 6, 9, 11, or N-imide positions.

51. A method of making a composition useful for the manufacture of light harvesting arrays, said composition comprising a non-polar organic solvent and from 2 microMolar to 100 milliMolar of light harvesting rods solubilized in said organic solvent, said light harvesting rods comprising a polymer of Formula I:

$$X^1\text{-}(X^{m+1})_m \qquad (I)$$

wherein:

m is at least 1;

X¹ is a charge separation group having an excited-state of energy equal to or lower than that of X²;

X² through $X^{m+1}$ are chromophores; and at least one of X² through $X^{m+1}$ has at least one perylene group coupled thereto;

wherein said perylene group is a compound of formula IV:

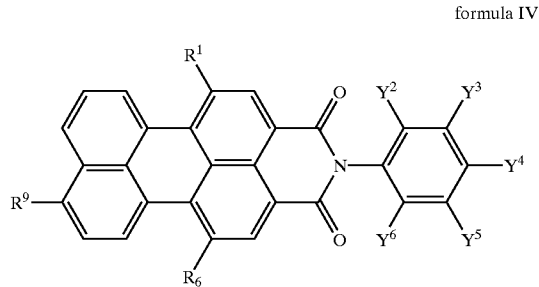

formula IV wherein:

R⁹ is a link to one of said chromophores;

R¹ and R⁶ are independently selected from the group consisting of H, alkyl, aryl, alkoxy, aryloxy, alkylthio, arylthio, halo, ethynylalkyl, ethynylaryl, dialkylboronate and trialkyltin; and Y² through Y⁶ are independently selected from the group consisting of H, alkyl, aryl, alkoxy, aryloxy, alkylthio, arylthio, halo, ethynylalkyl, ethynylaryl, dialkylboronate, and trialkyltin;

wherein either (i) Y⁴ is halo, ethynyl, dialkylboronate, or trialkyltin, or (ii) Y³ is halo, ethynyl, dialkylboronate, or trialkyltin;

said method comprising the steps of:

(a) providing a mixture of X¹ through $X^{m+1}$ as monomers in said organic solvent with an amine and a catalyst;

(b) polymerizing said monomers in said mixture to produce a polymer of Formula I; and then (c) separating amine and catalyst from said mixture to provide said composition having said polymer of Formula I solubilized therein.

52. A method according to claim 51, wherein said polymerizing step is carried out by a Glaser or Sonogashira reaction.

53. A method according to claim 51, wherein said solvent is selected from the group consisting of tetrahydrofuran, toluene, chloroform, chlorobenzene, xylene, dichloromethane, mesitylene, 1,1,1-trichloroethane, 2-chloronaphthalene, 1,2-dichlorobenzene, 1,1,2,2-tetrachloroethane, and mixtures thereof.

54. A method according to claim 51, wherein m is from 2 to 49.

55. A method according to claim 51, wherein at least one of X² through $X^{m+1}$ has at least two perylene groups coupled thereto.

56. A method according to claim 51, wherein at least one of X² through $X^{m+1}$ further has at least one of a perylene group coupled thereto at a perylene N-imide position.

57. A method according to claim 51, wherein at least one of X² through $X^{m+1}$ further has at least one of a perylene group coupled thereto at a perylene 1, 6, 9, or 11 position.

58. A method according to claim 51, wherein:

m is from 2 to 49;

at least one of X² through $X^{m+1}$ further has at least two perylene groups coupled thereto;

said perylene groups are perylene mono-imides; and said perylene groups are coupled at the perylene 1, 6, 9, 11, or N-imide positions.

59. A compound according to Formula II:

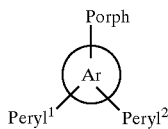

II wherein:

Ar is an aromatic group;

Porph is a porphyrinic macrocycle;

Peryl¹ is a first perylene group; and

Peryl² is a second perylene group.

60. A compound according to claim 59, wherein Ar is selected from the group consisting of benzene, thiophene, furan, pyrrole, pyridine, naphthalene, anthracene, phenanthrene, biphenyl, indene, quinoline, pyridazine, pyrimidine, fluorene, and pyrazine.

61. A compound according to claim 59, wherein Ar is benzene.

62. A compound according to claim 59, wherein said perylene groups are perylene mono-imides.

63. A compound according to claim 59, wherein said perylene groups are perylene (bis)imides.

64. A compound according to claim 59, wherein said perylene groups are coupled to said aromatic group at the perylene N-imide position.

65. A compound according to claim 59, wherein said perylene groups are coupled to said aromatic group at the perylene 1, 6, 9, or 11 position.

66. A compound according to claim 59, wherein said porphyrinic macrocycle comprises a porphyrin group substituted with Ar at the 5-position, X at the 10-position, Y at the 15-position, and Z at the 20-position; wherein Y is an alkyl or aryl group; and wherein X and Z are independently selected substituents selected from the group consisting of iodo, bromo, ethynyl, 2-(trimethylsilyl)ethynyl, 4-ethynylphenyl, 4-[2-(trimethylsilyl)ethynyl]phenyl, 4-iodophenyl, 4-bromophenyl, 4,4,5,5-tetramethyl-1,3,2-dioxaborolan-2-yl, and 4-(4,4,5,5-tetramethyl-1,3,2-dioxaborolan-2-yl)phenyl.

67. A compound according to Formula III:

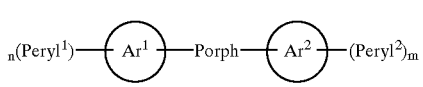

III wherein:

Ar¹ is a first aromatic group;

Ar² is a second aromatic group;

Porph is a porphyrinic macrocycle;

Peryl¹ is a perylene group;

Peryl² is a second perylene group;

m is from 1 to 3; and n is from 1 to 3.

68. A compound according to claim 67, wherein $Ar^1$ and $Ar^2$ are each independently selected from the group consisting of benzene, thiophene, furan, pyrrole, pyridine, naphthalene, anthracene, phenanthrene, biphenyl, indene, quinoline, pyridazine, pyrimidine, fluorene, and pyrazine.

69. A compound according to claim 67, wherein $Ar^1$ and $Ar^2$ are benzene.

70. A compound according to claim 67, wherein said perylene groups are perylene mono-imides.

71. A compound according to claim 67, wherein said perylene groups are perylene (bis)imides.

72. A compound according to claim 67, wherein said perylene groups are coupled to said aromatic groups at the perylene N-imide position.

73. A compound according to claim 67, wherein said perylene groups are coupled to said aromatic groups at the perylene 1, 6, 9, or 11 position.

74. A compound according to claim 67, where said porphyrinic macrocycle comprises a porphyrin substituted with $Ar^1$ at the 5-position, X at the 10-position, $Ar^2$ at the 15-position, and Z at the 20-position; and wherein X and Z are independently selected substituents selected from the group consisting of iodo, bromo, ethynyl, 2-(trimethylsilyl)ethynyl, 4-ethynylphenyl, 4-[2-(trimethylsilyl)ethynyl]phenyl, 4-iodophenyl, 4-bromophenyl, 4,4,5,5-tetramethyl-1,3,2-dioxaborolan-2-yl, and 4-(4,4,5,5-tetramethyl-1,3,2-dioxaborolan-2-yl)phenyl.

75. A compound of formula IV:

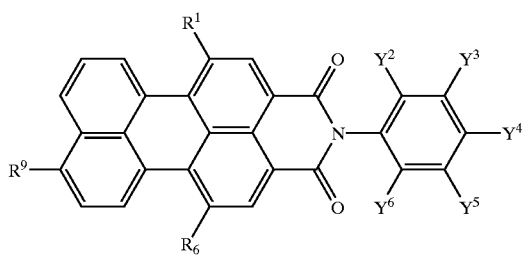

formula IV wherein:
$R^1$, $R^6$, and $R^9$ are independently selected from the group consisting of H, alkyl, aryl, alkoxy, aryloxy, alkylthio, arylthio, halo, ethynylalkyl, ethynylaryl, dialkylboronate and trialkyltin; and $Y^2$ through $Y^6$ are independently selected from the group consisting of H, alkyl, aryl, alkoxy, aryloxy, alkylthio, arylthio, halo, ethynylalkyl, ethynylaryl, dialkylboronate, and trialkyltin;

wherein either (i) $Y^4$ is halo, ethynyl, dialkylboronate, or trialkyltin, or (ii) $Y^3$ is halo, ethynyl, dialkylboronate, or trialkyltin.

76. The compound according to claim 75, wherein:
$Y^2$ and $Y^6$ are H or alkyl;
$Y^4$ is halo, ethynyl, dialkylboronate, or trialkyltin; and
$Y^3$ and $Y^5$ are H.

77. The compound according to claim 75, wherein $Y^2$, $Y^4$ and $Y^5$ are H, $Y^3$ is halo, ethynyl, dialkylboronate, or trialkyltin and $Y^6$ is alkyl.

78. A compound of formula V:

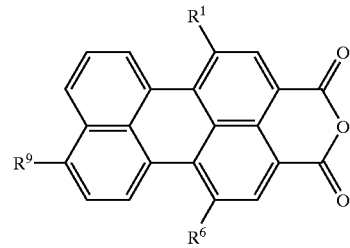

formula V wherein:
$R^1$ and $R^6$ are independently selected from the group consisting of H, alkyl, aryl, alkoxy, aryloxy, alkylthio, arylthio, halo, ethynylalkyl, ethynylaryl, dialkylboronate, and trialkyltin; and $R^9$ is selected from the group consisting of alkyl, aryl, alkoxy, aryloxy, alkylthio, arylthio, ethynylalkyl, ethynylaryl, dialkylboronate, and trialkyltin.

79. A compound of formula VI:

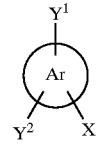

VI wherein
Ar is an aromatic group; and
$Y^1$ and $Y^2$ are independently selected perylene mono-imide groups; and
X is selected from the group consisting of formyl, halo, or 5-dipyrromethane.

80. A compound according to claim 79, wherein Ar is selected from the group consisting of benzene, thiophene, furan, pyrrole, pyridine, naphthalene, anthracene, phenanthrene, biphenyl, indene, quinoline, pyridazine, pyrimidine, fluorene, and pyrazine.

81. A compound according to claim 79, wherein Ar is benzene.

* * * * *